United States Patent [19]

Ledley et al.

[11] Patent Number: 4,474,186
[45] Date of Patent: Oct. 2, 1984

[54] COMPUTERIZED ELECTRO-OCULOGRAPHIC (CEOG) SYSTEM WITH FEEDBACK CONTROL OF STIMULI

[75] Inventors: Robert S. Ledley, Silver Spring; Thomas J. Golab, Beltsville; Michael Buss, Kensington, all of Md.

[73] Assignee: Georgetown University, Washington, D.C.

[21] Appl. No.: 359,682

[22] Filed: Mar. 18, 1982

Related U.S. Application Data

[63] Continuation-in-part of Ser. No. 58,300, Jul. 17, 1979, Pat. No. 4,320,768.

[51] Int. Cl.³ .............................................. A61B 5/04
[52] U.S. Cl. .................................................... 128/733
[58] Field of Search ............................... 128/731–733, 128/745

[56] References Cited

U.S. PATENT DOCUMENTS

| | | | |
|---|---|---|---|
| 2,860,627 | 11/1958 | Harden et al. | 128/731 |
| 3,172,404 | 3/1965 | Copenhaver et al. | 128/731 |
| 3,258,008 | 6/1966 | Willet-Durand | 128/745 |

Primary Examiner—William E. Kamm
Attorney, Agent, or Firm—Oblon, Fisher, Spivak, McClelland & Maier

[57] ABSTRACT

A computerized electro-oculographic (CEOG) system with feedback control of test stimuli comprises an integrated system for automated administration of electro-oculographic tests and visual evoked response tests to a patient, automated processing of the results derived from such tests, and automated feedback control of the test stimuli in accordance with the processed test results. The CEOG system is responsive to operator selection of desired stimuli to be administered, as well as to operator specification of various test stimuli characteristics, for automatically administering to the patient the test stimuli having the desired characteristics. Electrode test data derived therefrom are immediately recorded on-line, and are immediately and automatically analyzed to provide critical information for immediate display in acceptable format and in a very short period of time. The integrated CEOG system is especially noteworthy for its use of the analyzed test data to control and vary the test stimuli administered to the patient in accordance with the analyzed tests data results.

13 Claims, 47 Drawing Figures

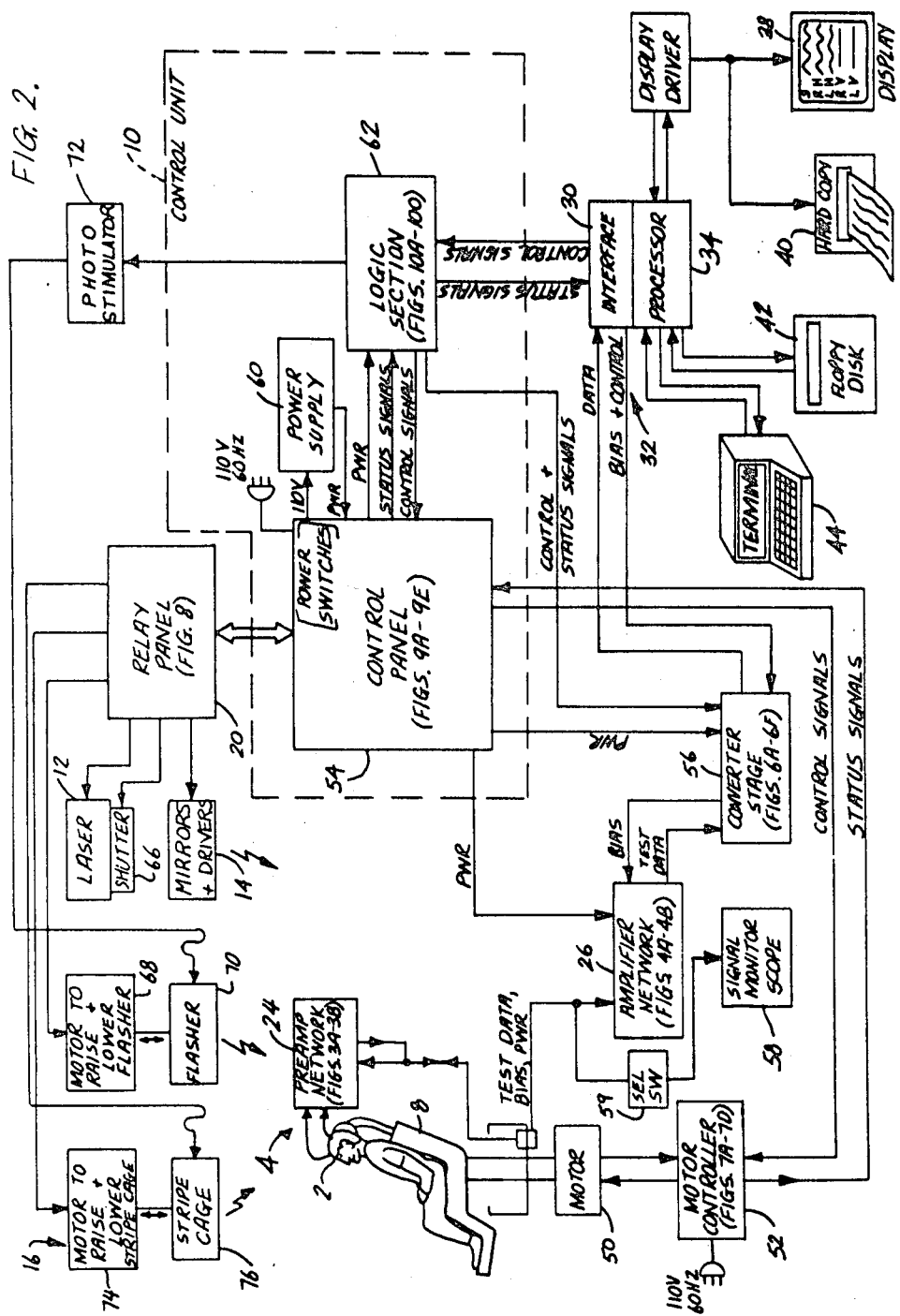

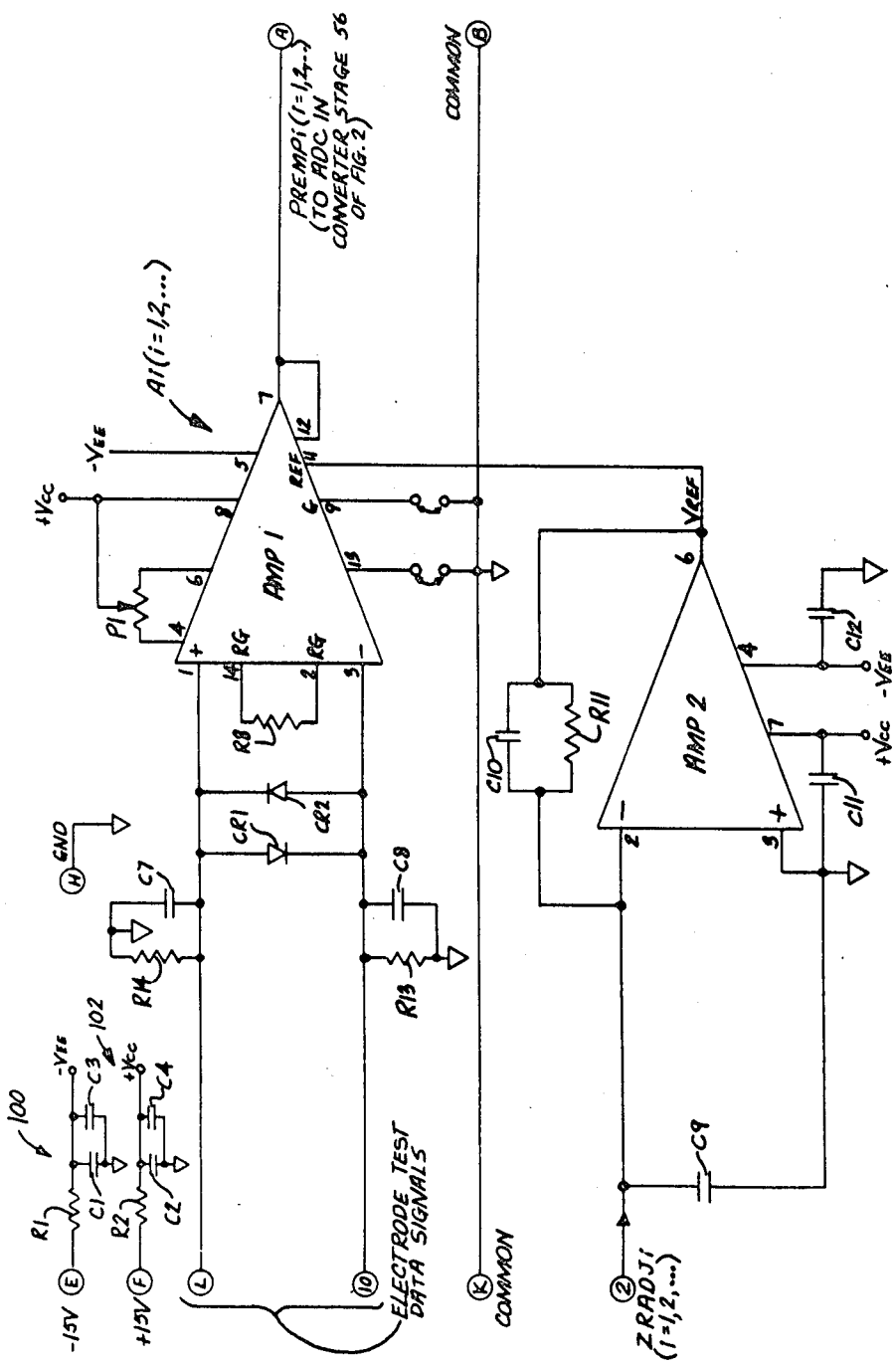

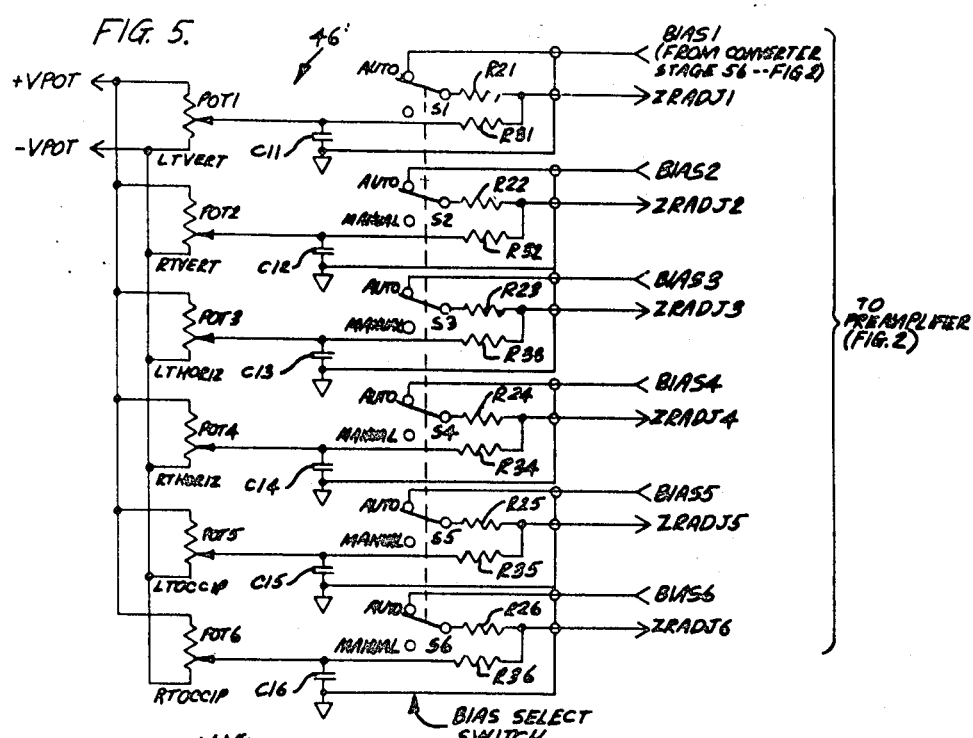
FIG. 5.
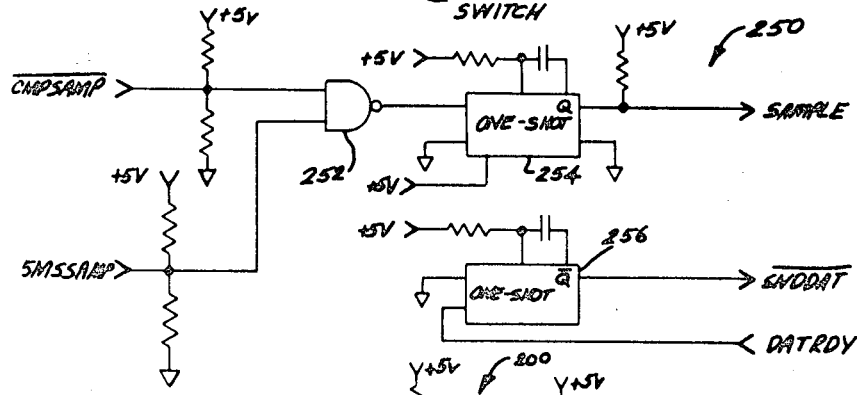
FIG. 6D.
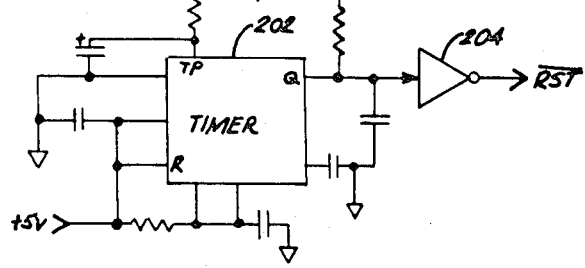

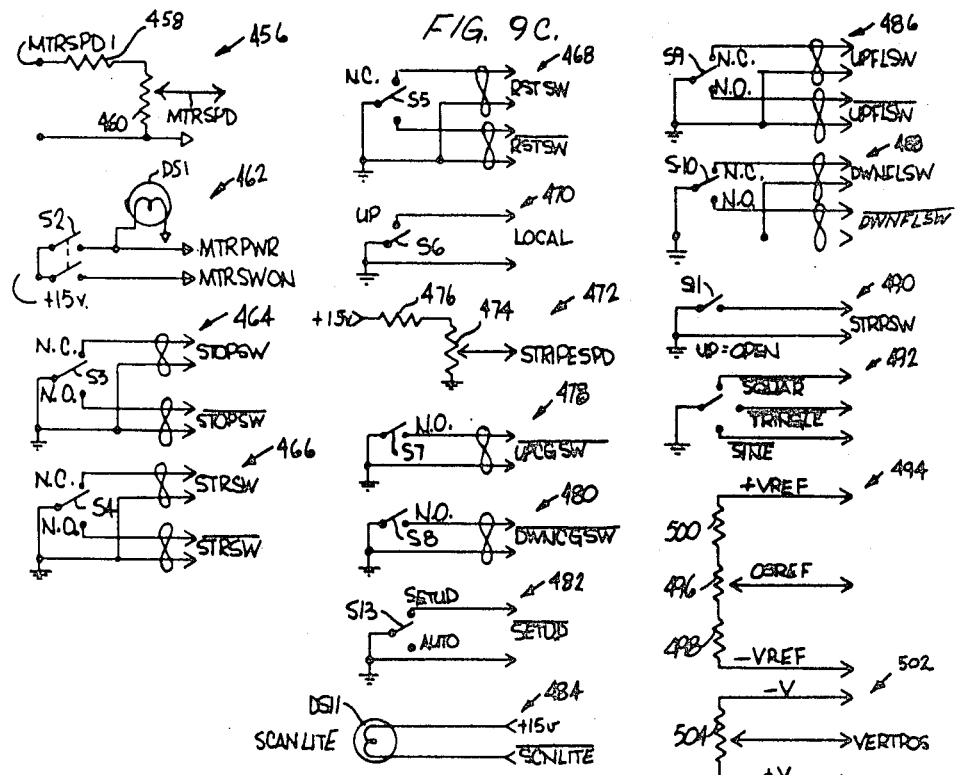

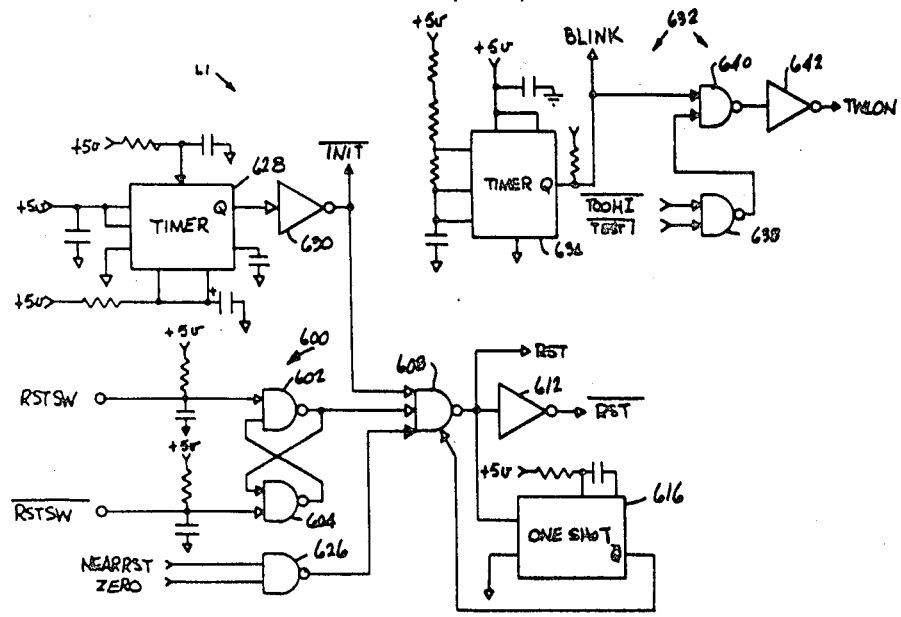
FIG. 10A.
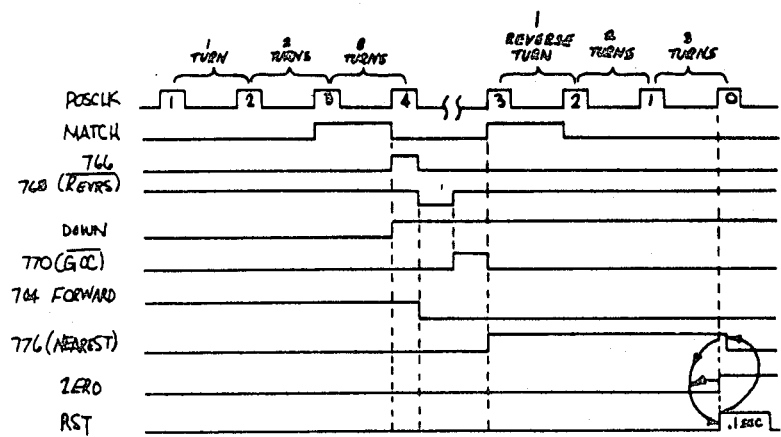
FIG. 10D(2)

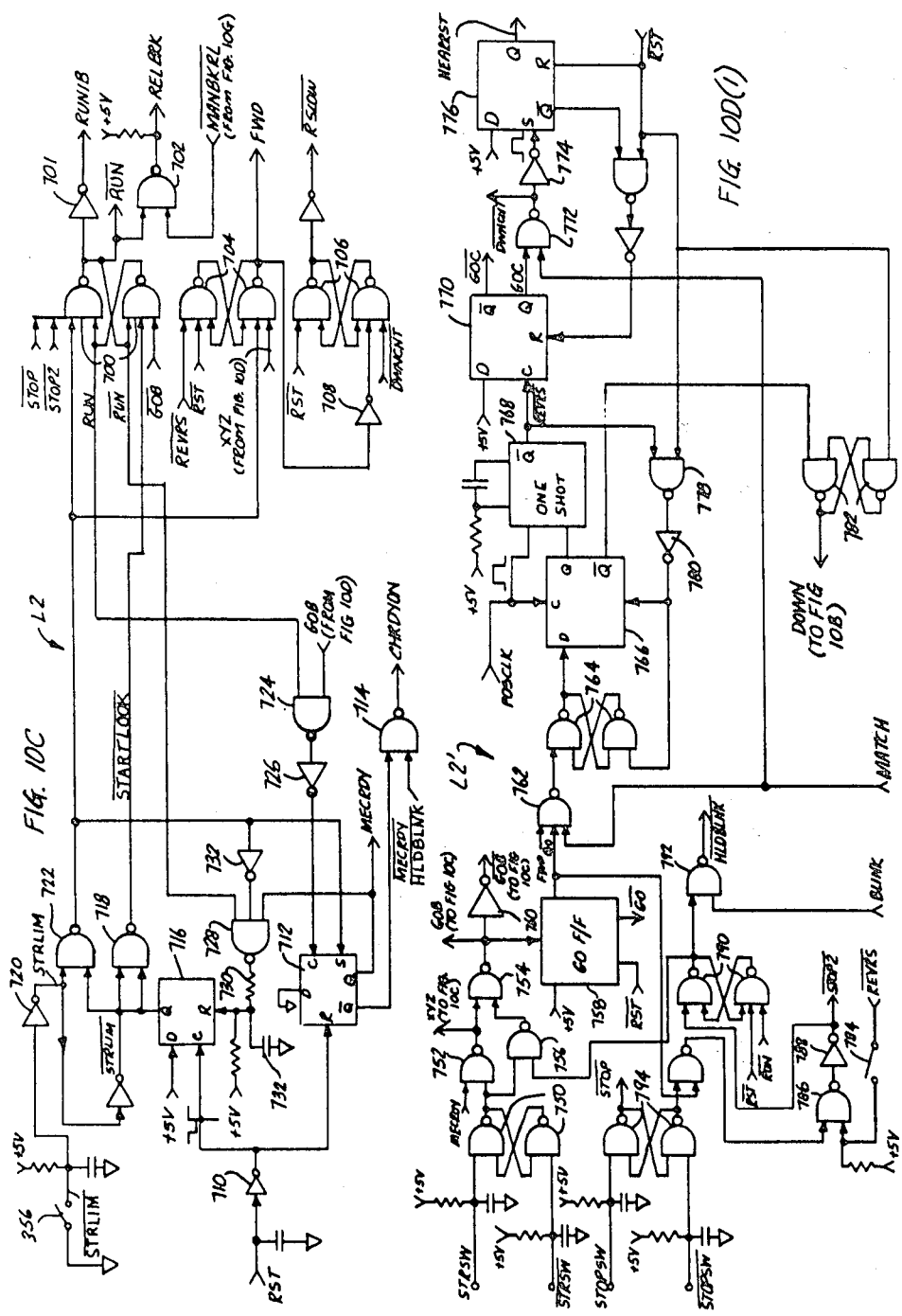

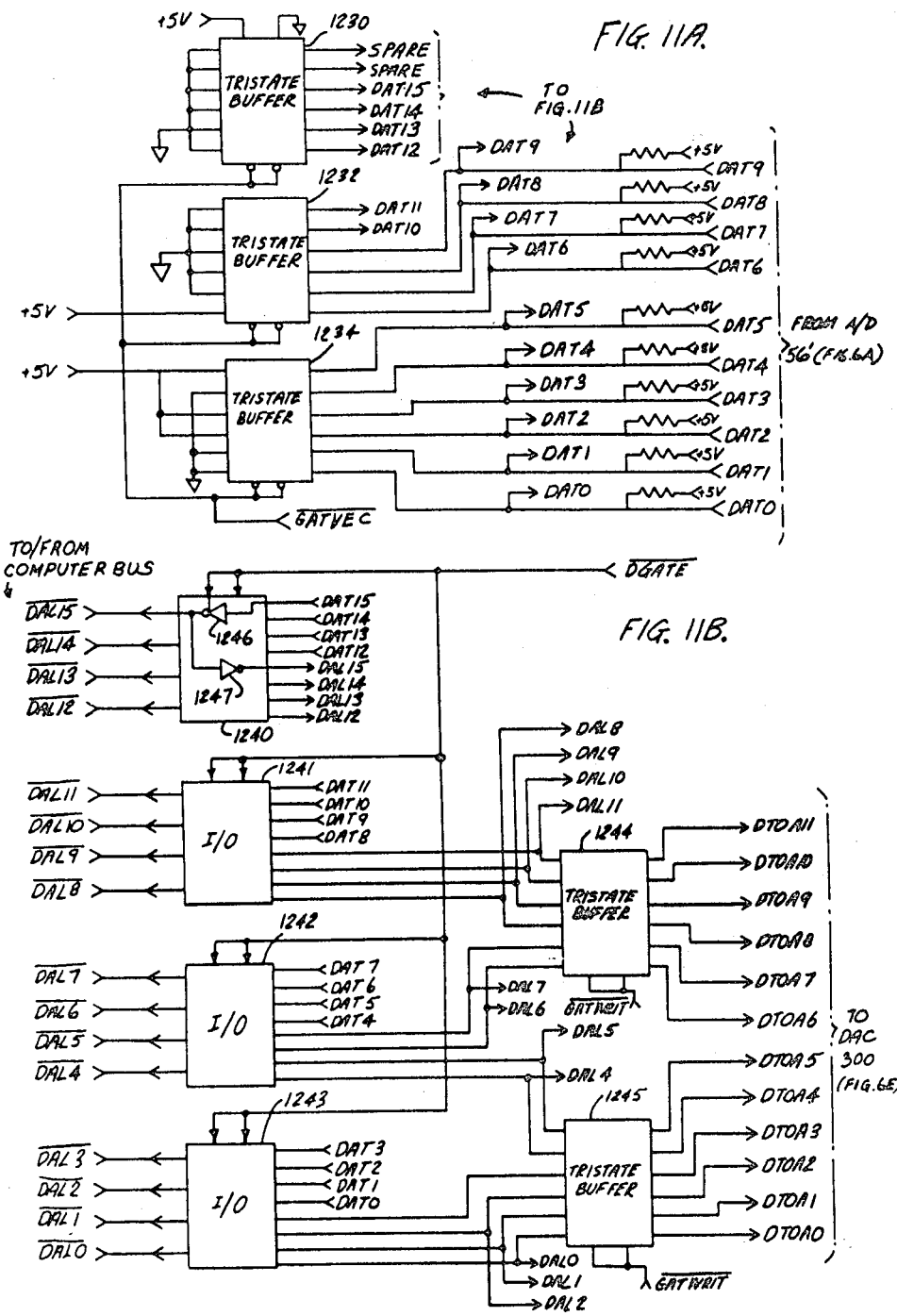

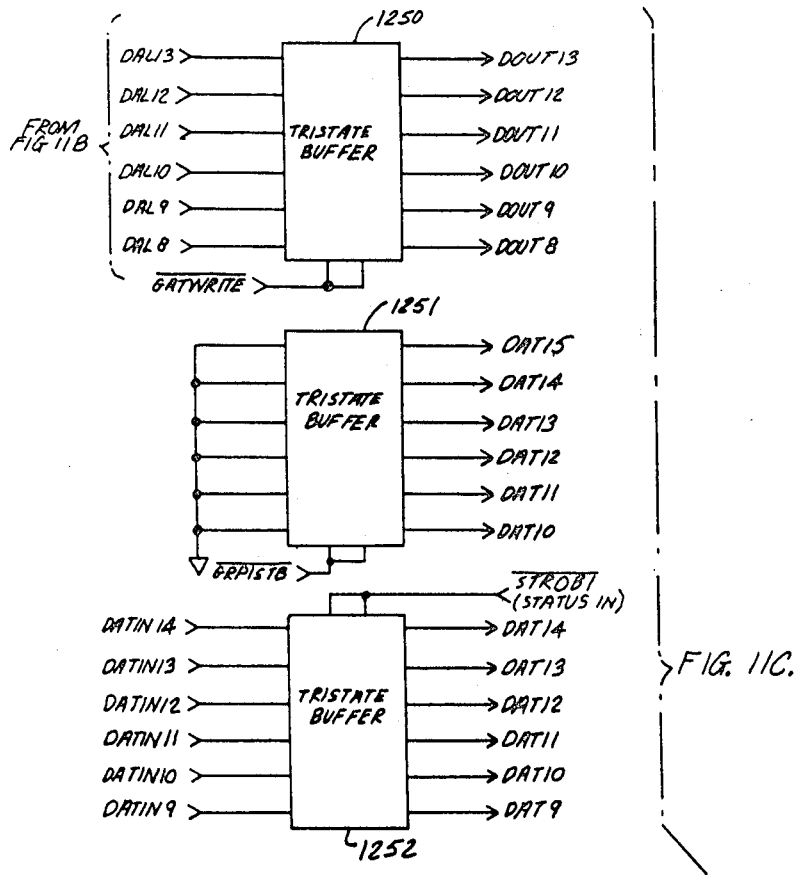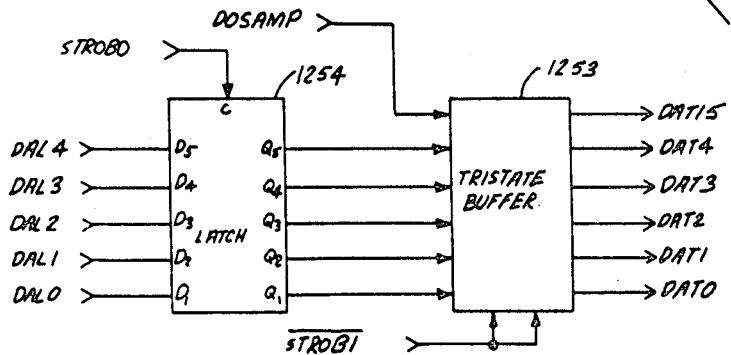
FIG. 11C.

COMPUTERIZED ELECTRO-OCULOGRAPHIC (CEOG) SYSTEM WITH FEEDBACK CONTROL OF STIMULI

REFERENCE TO RELATED APPLICATION

This is a continuation-in-part of U.S. Ser. No. 58,300 filed on July 17, 1979, now U.S. Pat. No. 4,320,768 issued on Mar. 23, 1982.

BACKGROUND OF THE INVENTION

1. Field of the Invention

The present invention relates to a computerized electro-oculographic system and, more particularly, an integrated system for automated administration of electro-oculographic tests and visual evoked response tests to a patient, and automated processing of results derived from such tests, coupled with use of the processed test results for feedback control of the test stimuli. Automated administration of the tests is conducted either under the direct control of the test administrator via an operator control section (console), or under the automated control of a programmed computer with indirect control by the test administrator.

2. Description of the Prior Art

For a number of years, electro-oculographic (or electro-nystagmographic) techniques have been utilized by physicians to gain useful information about a patient with certain complaints—notably, complaints of disturbed equilibrium. Such information has typically been gained by observing the patient's eye movements during certain kinds of visual and vestibular stimulation. At times, such observations provide the only physical findings that support a patient's complaint, and they also assist the physician in defining the anatomic location of the patient's disorder. For example, by observing eye movements, the physician is often able to distinguish between a peripheral vestibular disorder and one located within the central nervous system, and is sometimes able to lateralize a peripheral disorder, or to further localize a central nervous system disorder.

In early times, the physician examined eye movements merely by watching the patient's eyes. However, important signs were often missed because the physician could not prevent the patient from fixating, and visual fixation has a powerful suppressive effect on some types of nystagmus. Moreover, certain types of brain lesions and certain drugs impair or abolish the visual suppression effect; this phenomenon cannot be appreciated unless nystagmus is observed both when visual fixation is allowed and when it is denied.

A number of methods were available to overcome the latter disadvantages, but the one best suited to the needs of physicians has been electro-oculography. Electro-oculography has long been widely used for research purposes in psychology and ophthalmology. It has gradually acquired its more familiar name, electro-nystagmography, because of its extensive application to the study of nystagmus (although it is used to record other types of eye movements as well).

Basically, electro-nystagmography (ENG) owes its existence to the fact that the eye is, in effect, a battery, the cornea being a positive pole, the retina being a negative pole, and the potential difference between the two poles being normally at least one millivolt. This electrical potential creates, in the front of the head, an electrical field that changes its orientation as the eyeballs rotate. These electrical changes can be detected by electrodes placed on the skin of a patient, and, when the changes are amplified and used to drive a writing instrument, a trace of the eye position is obtained.

As stated in the *Manual of Electro-nystagmography* by Barber and Stockwell (St. Louis: The C. V. Mosby Company, 1976), electrodes can be arranged on the skin in a number of ways, but a standard technique for clinical purposes involves placement of two electrodes bitemporally (that is, one on the right temple and the other on the left temple) to monitor horizontal eye position, placement of a second pair of electrodes, one above and the other below one of the eyes, to monitor vertical position of the eyes, and placement of an additional electrode, usually on the forehead, to serve as a ground or reference point. Of course, other arrangements of electrodes can be utilized, as are known in the art (for example, an occipital arrangement).

A significant problem in the prior art, relating to the monitoring of eye movements using such electrode arrangements, results from the necessity, or at least desirability, of maintaining a constant relationship between the center position of the eye and a given value of the measured electrical parameter (for example, zero volts). Typically, sustained use of such electrode arrangements and measuring devices results in the development of an offset voltage. That is, the calibration of the measuring device varies so that a center position of the eye no longer results in a reading of zero volts, but rather results in some finite number of volts (referred to as the offset voltage). This has obvious disadvantages with respect to the accuracy of the eye movement measurements.

Inasmuch as such electrode measurement devices are usually equipped with an amplifying stage (or preamplifiers, as the case may be), prior art techniques for zero-adjusting, or biasing, the amplifier arrangement so as to eliminate the offset voltage have been limited to manual techniques. Whereas such manual techniques have been an improvement, they have two major disadvantages. Firstly, such techniques amount to broad-range (coarse) adjustments, at best, and thus do not achieve the narrow-range (fine) adjustments necessary for maximum accuracy in measurements. Secondly, such manual techniques—even if performed on a regular basis—cannot compare with the additional efficiency achieved by continuous, automatic zero-adjustment to eliminate the offset voltage.

As previously mentioned, the placement of small electrodes on the head of the patient makes it possible to record ocular motility. Specifically, electro-oculograms representing measurement of both horizontal and vertical eye movements—and occipital measurements as well—are recorded with the electrodes fixed to the head of the patient. Thus, eye movements and visual responses from the patient can be recorded as the patient undergoes one or more tests. Typically, a series of six ocular motor, vestibular and response tests are conducted, as follows:

(1) Gaze tests—wherein eye movements are recorded as the patient looks straight ahead, to the right, to the left, up and down, both with the eyes open and closed.

(2) Saccadic tests—wherein eye movements are recorded as the patient follows a jumping light spot.

(3) Tracking tests—wherein eye movements are recorded as the patient follows a uniformly moving light spot.

(4) Optokinetic tests—wherein eye movements are recorded as the patient watches vertical stripes moving at various speeds to the right, and then to the left, the test being performed both with the patient stationary while the image revolves, and with the patient revolving while the image is stationary.

(5) Caloric tests—wherein each ear is irrigated twice, once with air above body temperature and once with air below body temperature, the irrigation affecting the vestibular sensors and producing horizontal nystagmus.

(6) Visual evoked response tests—wherein "vision" is assessed, the integrity of the visual pathways (including the optic nerve, optic chiasm, and posterior visual pathways) being analyzed, and the visual evoked response being recorded between occipital electrodes (positioned contralateral to the eye—i.e., electrodes on the right-/left occipital, and electrodes on the right/left ear lobe), as stimulated by a burst of short, high-intensity light pulses, and a reference (ground) electrode (placed on the forehead of the patient).

Whereas it is known in the art to administer such tests, such tests have typically been performed in a piecemeal manner by one or more physicians or attendants, operating with various separate and non-integrated components. For example, one device might be utilized to perform the saccadic test, followed by a period of time during which a second piece of equipment is actuated in order to perform the tracking test, and so forth for the remaining tests. Moreover, one group of equipment (light flasher or light scanning equipment) might be utilized for administration of the saccadic and tracking tests, and then a second group of equipment (an optokinetic device in combination with a rotating chair) might be utilized to perform the optokinetic test. The lack of availability of an integrated system for performing these various tests, with the various and different types of equipment, has resulted in both time inefficiencies in the administration of such tests, and more importantly inaccuracy in the statistical data obtained.

Moreover, data obtained as a result of the above-mentioned tests typically include artifacts caused by electronic noise, eye blinks, random eye movements, poor electrode contact, and so forth. In the typical system, wherein minute voltage changes (as little as several microvolts per degree of eye displacement) are amplified many thousands of times, distortion of the statistics is a very real problem. For example, the previously mentioned "offset voltage" phenomenon encountered in electrode measuring arrangements of the type employed with such systems is a major contributor to statistical inaccuracy.

Finally, in the typical prior art system, wherein electrode-measured data is—after amplification—recorded directly on a recording device, there is always the possibility of inaccuracies resulting from either the generation of extraneous signals or improper calibration of the recording equipment. As a result, raw data—no matter how accurately measured and obtained—can be distorted by such extraneous signals and/or inherent lack of calibration of the recording equipment, and the actual data—once erroneously recorded—is irretrievable and lost forever.

There has been some attempt in the prior art to overcome the latter disadvantages. In particular, there have evolved systems—such as that disclosed by Robert W. Baloh et al in "Algorithm for Analyses of Saccadic Eye Movements Using a Digital Computer," *Aviation, Space and Environmental Medicine* (May 1976), pp. 523 ff.—wherein measured data corresponding to horizontal and vertical eye movements, and target position, are—after digitization—recorded on magnetic tape. Then, at a later time, such digitized records are read into a computer equipped with a Saccade Analysis Program (SAP) developed to analyze, in an off-line mode of operation, the saccadic eye movements previously recorded. Such systems can be equipped with not only a processor and memory, but also various peripheral units (disk drive, magnetic tape drive, graphics display terminal, and hard copy printer).

Whereas such systems display the raw data for visual inspection and allow the user to study the data for possible errors in recording and/or digitization, it is important to note that such systems are nevertheless "off-line" systems whereby data is recorded in one operation and then processed in a second operation (on different equipment) separated by a time lapse there-between.

Another type of prior art system is that exemplified by the disclosure of a "Method and Apparatus for Brain Waveform Examination" in U.S. Pat. No. 3,893,450—Ertl, issued on July 8, 1975. That patent discloses a method and apparatus for examining the brain waveform of a subject (for example, by electro-encephalographic (EEG) techniques) by providing a stimuli (such as light), and determining a characteristic of a mathematically determinable point in the brain waveforms of the subject (for example, by means of an EEG amplifier, filter, zero-crossing detector and computer). Upon making of such determination, the stimulation of the subject by a single photo-stimulator is controlled or varied via a closed-loop feedback path (between, for example, the computer and the single photo-stimulator). However, systems such as are represented by the latter patent do not provide a solution to most, if not all, of the problems discussed above. Thus, the system of the latter patent—even though it provides for immediate processing of the brain waveform data, and resultant control of the single photo-stimulator in accordance therewith—does not comprise an integrated system capable of automated administration of *various* test stimuli to a patient via employment of an operator control section (console), does not provide for correction of the "offset voltage" phenomenon, does not expressly provide for automated processing of resultant test data so as to provide critical information to the attending physician or test administrator in acceptable format and in a very short period of time, and does not provide for feedback control of *various* test stimuli in accordance with the automated processing of the test data.

In summary, there has been a need in the prior art for an integrated electro-oculographic system which not only provides for automated test administration (including control of test stimuli) to a patient, and is capable of immediate recording and display of the raw data in real time, followed by rapid and accurate analysis of such raw data so as to provide the attendant or physician with critical information in an acceptable form and in a very short period of time, but also is capable of feedback control of various test stimuli in accordance with the automated processing of test data.

SUMMARY OF THE INVENTION

Therefore, according to the present invention, there is provided a computerized electro-oculographic (CEOG) system and, more particularly, an integrated CEOG system having the capabilities of automated administration of various electro-oculographic (EOG) and visual evoked response (VER) tests to a patient in response to operator selection of such tests, immediate on-line recording and display of test results (raw data), rapid and accurate analysis of such raw data in order to provide critical information to the test administrator in an acceptable form and in a very short period of time, continuous/automatic data processing and "editing" to delete artifacts (typically, caused by electronic noise, eye blinks, random eye movements, poor electrode contact, etc.), and feedback control of test stimuli in accordance with the processing of the test data.

The CEOG system of the present invention basically comprises the following components: a patient system, or test unit, including a rotating chair (for use, for example, in the administration of the optokinetic tests), various visual test stimuli devices (such as, for example, an optokinetic device, flasher, and light source), and respective control units for controlling both the rotating chair and the visual test stimuli devices; various input devices (preamplifier, amplifier, and digitizer) for receiving and providing electrode test data to a computer; a computer (including—for example—the usual central processing unit, storage media, display/keyboard and hard-copy printer), and an interface unit between the computer and the aforementioned control units and various input devices for facilitating input of test data and feedback control of test stimuli administration in response to processing of the test results.

The integrated CEOG system of the present invention is capable of automated administration of test stimuli to a patient via the provision of an operator control section (console), by means of which the test administrator can select one of various types of stimuli (in accordance with the particular type of test being administrated), and can as well designate various parameters or characteristics of the desired stimuli. For example, the test administrator can operate the operator control section (console) to cause administration of optokinetic tests. Specifically, the administrator can, in an automated manner, actuate both the rotatable chair (in terms of commanding rotation of the chair and selecting a rotation speed, number of turns for which the chair is to be rotated, etc.) and the optokinetic device (commanding lowering of the optokinetic device into position and designating the speed of rotation of the stripe cage of the optokinetic device, etc.). Similarly, the test administrator can operate the CEOG system of the present invention so as to administer, in an automated manner, the saccadic test or the tracking test (in terms of actuating a flasher device or a light scanner, respectively, and designating the scanning speed, scanning pattern, etc.).

Moreover, in the CEOG system of the present invention, electrode test data derived from electrodes attached to the head of the patient are, after amplification and digitization, stored in the system processor, the system having the capability of immediate display of the raw data via any one of various conventional display devices (graphic display terminal, hard-copy printer, etc.). However, the CEOG system of the present invention is unique in that the adverse effects of the typically encountered offset voltage characterizing such electrode test data (which are initially in the form of input voltage signals) can be compensated for by not only manual techniques, but also automated techniques. Specifically, the CEOG system of the present invention affords the test administrator with an immediate display of the analog test data signals after preamplification, but before amplification, and further provides the test administrator with means for manually adjusting amplifier network reference voltages so as to eliminate the "offset voltage" effect by zero-adjusting the amplifiers to achieve zero-volt readings for non-variation of the patient's eyes from a center position. In addition, the CEOG system of the present invention provides the test administrator with the selectable option of automatic zero-adjustment by means of the system processor.

Finally, the CEOG system of the present invention—by means of the system processor—provides immediate, on-line processing of the input test data so as to permit immediate processing and editing of the input test data to delete artificats typically caused by electronic noise, eye blinks of the patient, random eye movements of the patient, poor electrode contact, etc. In this manner, the inventive CEOG system is able to detect minute voltage changes (of the order, typically, of several microvolts per degree of eye displacement), to amplify them many thousands of times without distortion, and both to record the processed data in memory (for future use) and to display the processed data on a "real time" basis. The inventive CEOG system is, moreover, able to accomplish the above without accepting extraneous signals from the "outside world," and without generating any extraneous signals internally.

Thus, the inventive CEOG system is able to provide rapid and accurate analysis of data so as to afford the physician with critical information in acceptable format and in a very short period of time. Such provided data typically includes: amplitude, frequency and duration of fast and slow components of nystagmus; maximum, minimum and mean velocity and amplitude of saccades (sychronized jumps made by the eye in moving from one visual target to another in a short period of time); comparison of saccadic amplitude with light jump amplitude; and measurements of the delay between light jump and eye jump. The latter data results from statistical analyses performed by the inventive CEOG system, followed by graphic display of the information resulting therefrom.

Additionally, the inventive CEOG system has the capability of utilizing the processed test data to controllably vary the test stimuli administered, in an automated manner, to the patient. Since this is done "on-line" and in an automated manner, immediate reaction of the patient to continual variation of the test stimuli can be obtained.

Therefore, it is an object of the present invention to provide a computerized electro-oculographic (CEOG) system and, in particular, an integrated system for automated administration of various EOG and VER tests to a patient, followed by automated processing of the resultant test data so as to provide critical information to the attending physician in acceptable format and in a very short period of time, and feedback control of the test stimuli in accordance with the processed test data.

It is an additional object of the present invention to provide an integrated system for performing quickly and efficiently, and in an automated manner, various EOG or VER tests selected by the test administrator, utilizing the various test stimuli equipment included in the system, with feedback control of the test stimuli in accordance with processing of the test data.

It is an additional object of the present invention to provide an integrated system which is responsive to operator selection of desired stimuli to be administered to a patient, as well as to operator specification of various test stimuli characteristics, for automatically administering, to the patient, the test stimuli having the desired characteristics, with the added capability of feedback control of the test stimuli.

It is an additional object of the present invention to provide an integrated system for automated administration of test stimuli to a patient, wherein operator selection of the various test stimuli and feedback control thereof is facilitated by utilization of a single operator control section, or console.

It is an additional object of the present invention to provide a system for automated administration of test stimuli, wherein electrode test data is immediately recorded on-line, and is available for immediate display of such "raw data" to the test administrator.

It is a further object of the present invention to provide an integrated test system wherein electrode test data is immediately and automatically analyzed to provide critical information, needed by a physician, in acceptable format and in a very short period of time, and wherein such analyzed data is used for feedback control of the test stimuli.

It is a further object of the present invention to provide an integrated CEOG system wherein the adverse effects of the "offset voltage" phenomenon—typically encountered in the derivation of test data from electrodes connected to a patient—are negated by provision of both manual and automated zero-adjusting capabilities.

With the above and other objects in view that will hereinafter appear, the nature of the invention will be more clearly understood by reference to the following description, the appended claims, and the accompanying drawings.

BRIEF DESCRIPTION OF THE DRAWINGS

FIG. 2 is a more detailed block diagram of the CEOG system of the invention.

FIG. 3B is a detailed schematic of the preamplifiers A1, A2, ..., A6 of the preamplifier network 24 of FIG. 3A.

FIG. 5 is a diagrammatic representation of biasing circuitry 46' contained in the amplifier network 26 of the CEOG system of FIG. 2.

FIG. 6D is a detailed schematic diagram of further ADC logic circuitry 200 and 250 of the converter stage 56 of the CEOG system of FIG. 2.

FIGS. 9B through 9E are detailed schematic diagrams of the control panel 54 of the CEOG system of FIG. 2.

FIGS. 11A through 11D and 11G are detailed logic block diagrams and circuit schematics of the interface 30 of the CEOG system of FIG. 2.

DETAILED DESCRIPTION

Figure 1:
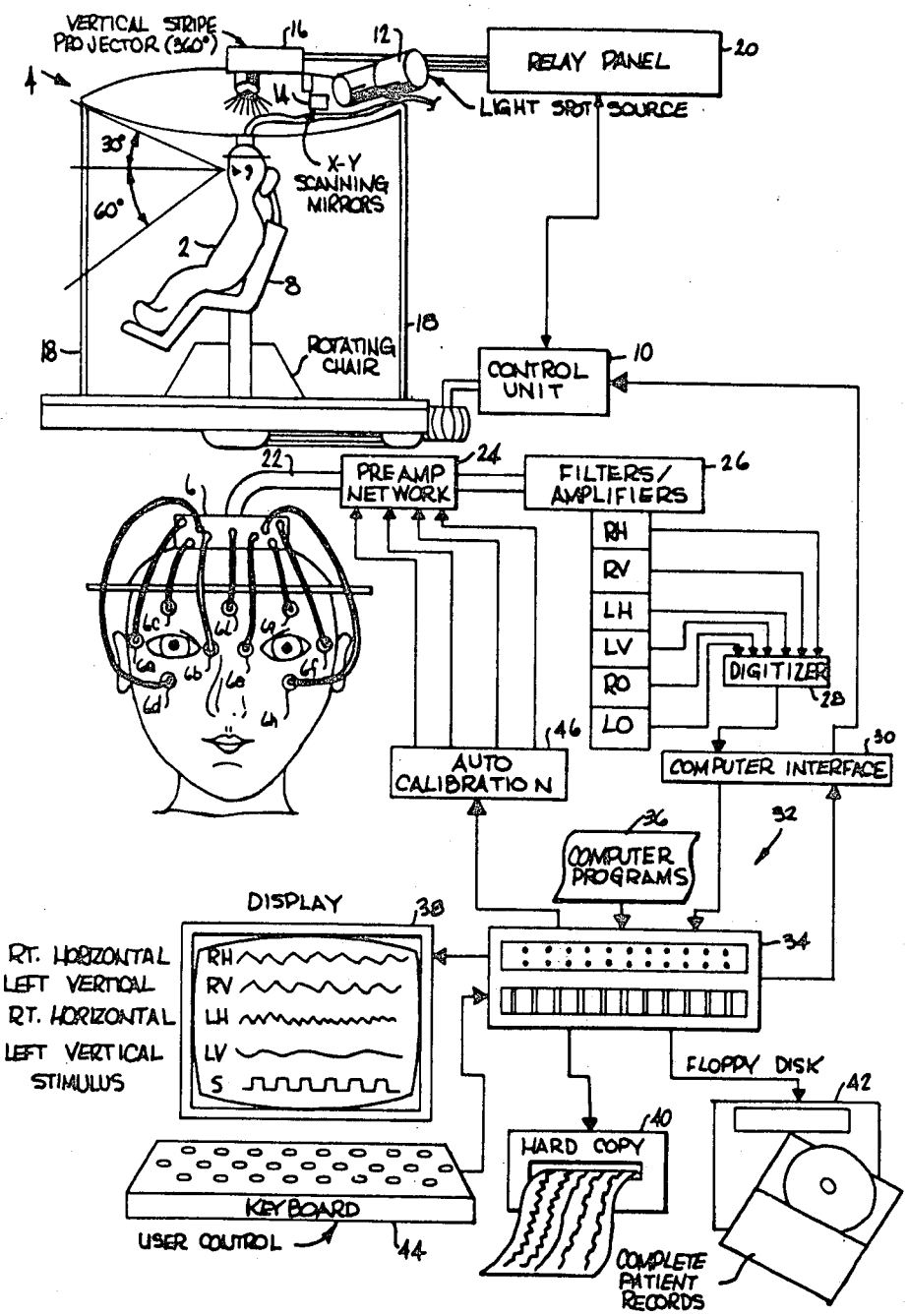
FIG. 1 is a diagram representing a broad overview of the CEOG system of the present invention.

FIG. 1 is a diagram representing a broad overview of the CEOG system of the present invention.

The CEOG system of the present invention is for use in performing electro-oculographic (EOG) tests and visual evoked response (VER) tests on a subject 2, the subject being positioned within a patient system or test station 4. Typically, an electrode junction box 6 is placed on or near the head of the subject 2, and electrodes 6a through 6f connected to junction box 6 are attached to the skin on the head of the subject 2, so as to permit EOG testing; for VER testing, two pairs of electrodes are connected to the right occipital/right ear lobe, respectively, of the head of the patient, while a fifth electrode 6f is connected to the patient's forehead, as a ground (or reference) electrode.

The test station 4, in which the subject is positioned, comprises a rotating chair 8 for rotating the subject 2 (if appropriate for the particular test being administered), the rotation of the chair being controlled by control unit 10. The test station 4 also comprises: a light spot source 12 for generating a light spot; a set of x-y scanning mirrors 14 for receiving and reflecting the light spot so as to cause the light spot to appear on the generally cylindrical walls 18 of the test station 4, the x-y scanning of the mirrors 14 being controllable so as to cause the light spot to move in the x and/or y directions in accordance with a controlled pattern called for by the paticular test; and an optokinetic device or system (a vertical stripe projector) 16 for causing vertical stripe patterns to be projected onto, and to appear on, the cylindrical walls 18 (also as appropriate for the particular test being administered). The light spot source 12, x-y scanning mirrors 14 and optokinetic device 16 are controlled by a relay panel 20, which is itself controlled by control unit 10.

In the particular arrangement shown in FIG. 1, electrodes 6a, 6b and 6e, 6f are connected to detect horizontal eye movement of the right and left eyes, respectively, of the subject 2. Similarly, electrodes 6c, 6d and 6g, 6h are connected to measure vertical eye movement of the right and left eyes, respectively, of the subject 2. Finally, a reference electrode 6i is connected in the area of the temple of the subject 2. It is to be understood that other arrangements of the electrodes 6a through 6i can be used, as called for by the particular test being administered. In fact, whereas electrodes 6a through 6i are connected in an arrangement typically utilized in the administration of EOG tests, it is to be understood that further electrodes (not shown) can be connected to the subject 2 in an "occipital lobe" arrangement for the administration of VER tests.

Electrodes 6a through 6i are connected to preamplifier network 24, the output of the preamplifier network 24 being provided to filters/amplifiers 26. Filters/amplifiers 26 provide analog outputs on respective channels corresponding to respective electrode measurements, and designated as RH (right horizontal), RV (Right vertical), LH (left horizontal), LV (left vertical), RO (right occipital), and LO (left occipital). The analog outputs from the filters/amplifiers 26 are provided to digitizer 28, which converts the analog signals to corresponding digital signals. The digital signals from digitizer 28 are provided, via computer interface circuit 30, to a computer, generally designated by reference numeral 32.

In the preferred embodiment, computer 32 comprises a processor 34, responsive to computer programs 36, for processing the digital input test data (that is, the digital outputs of digitizer 28, provided via computer interface 30), and for providing visual display of the test data on display device 38, hard copy recording of test results on hard copy printing device 40, and permanently recorded test data via a peripheral unit such as floppy disk 42. Computer 32 also comprises a keyboard 44 by which operator control of test administration, processing of test results, output of test results, and feedback control of test stimuli in accordance with processed test results can be achieved.

The CEOG of the present invention also comprises auto-calibration (or biasing) circuitry 46 connected to processor 34, by means of which automatic (processor-controlled) biasing of preamplifier network 24 can be achieved. This is in addition to manual biasing of preamplifier network 24. As will be discussed below in more detail, preamplifier network 24 is manually adjusted, and preferably automatically adjusted as well, for proper preamplifier biasing, so as to compensate for the offset voltages of the electrodes 6a through 6i, thereby maintaining zero adjustment of each electrode when the subject's eyes are directed toward a center position.

It will also be noted that, in a manner to be described below in more detail, processor 34 controls chair rotation via computer interface 30 and control unit 10, and controls the administration of test stimuli to the subject 2 via control unit 10 and relay panel 20.

Referring to the electrode junction box 6, it is to be noted that, in the preferred embodiment, preamplifier network 24 is physically located in the electrode junction box 6.

FIG. 2 is a more detailed block diagram of the CEOG system of the invention. Reference numerals previously employed in FIG. 1 to designate various elements of the CEOG system have been maintained in FIG. 2, where appropriate.

The CEOG system of the present invention generally comprises, with reference to FIG. 2, a patient system or test station 4 including a revolving chair 8, upon which the subject 2 is seated—typically during VER and EOG testing. The chair 8 is rotated by a motor 50, driven by a motor controller 52 connected to a power source (such as 110 volts, 60 Hz.). The motor controller 52 is, in turn, controlled by input control signals received from control panel 54 in control unit 10. In addition, various output status signals (to be discussed below) from motor 50 (pertaining, for example, to chair position and speed) are provided, via motor controller 52, to control panel 54 for distribution to other portions of the CEOG system (as will be discussed below).

Electrode test data derived from electrodes 6a-6i (FIG. 1) attached to the subject 2 (FIG. 2) are provided, via preamplifier network 24 and amplifier network 26, to analog-to-digital converters (ADC) contained in converter stage 56. Digital representations of the electrode test data are derived therein, and are provided as an input DATA to processor 34 via EOG interface 30.

In the preferred embodiment, it is highly useful to provide a signal monitor scope 58 for displaying, to the operator, the electrode test data signals as generated by preamplifier network 24. For example, by viewing the displayed electrode test data on scope 58, the operator of the CEOG system is able to perform manual bias adjustment of preamplifier network 24, by which broad-range biasing of preamplifier network 24 (to compensate for the voltage offset of the electrodes) can be accomplished easily and quickly. Moreover, as can be seen in FIG. 2, a preferred embodiment of the CEOG system includes a selector switch 59, by which the operator can select test data signals from a particular pair of electrodes for display on the scope, thus achieving individual bias adjustment of each respective preamplifier (corresponding to a selected pair of electrodes).

Moreover, processor 34—as a result of processing the received digital test data, DATA—provides an output BIAS (via interface 30, converter stage 56, and amplifier network 26) to preamplifier network 24. In response to the input BIAS, preamplifier network 24 is automatically biased so as to provide continuous/automatic compensation for the offset voltage of the electrodes.

Control panel 54 serves as a power distribution/junction box for distributing power throughout the system. Specifically, control panel 54 is powered by a 110 volts, 60 Hz. power input, and provides this A.C. power to power supply 60 which, in response thereto, provides necessary D.C. voltages (+5 v., +12 v., +15 v., −15 v., etc.) to the various elements of the system, as needed. Control panel 54 also receives the various D.C. power inputs from power supply 60, and distributes such D.C. power inputs throughout the system. Thus, as illustrated in FIG. 2, power outputs PWR are provided by control panel 54 to preamplifier network 24, amplifier network 26, converter stage 56 and logic section 62, among others.

Control panel 54 also serves the function of distributing various logic control signals throughout the system. As previously mentioned, motor controller 52—which controls rotation of the chair—receives control signals from control panel 54, such control signals originating in logic section 62 and processor 34. More specifically, control panel 54 provides control signals which, as will be seen below, command the motor controller 52 to control the motor 50 in such a manner that the chair 8 will commence revolution on command, will revolve at a given (commanded) speed S, will stop after one turn, after a series of turns, or on command, and will automatically restart revolution in the opposite direction.

Control panel 54 also receives and distributes various status signals, such as a chair position indication signal and chair turn information provided by chair 8 via motor 50 motor controller 52. Such status signals are provided to logic section 62 and interface 30. For example, motor 50 and motor controller 52 transmit, to control panel 54, status signals defining tachometer information (relating to the actual speed of the rotating chair 8), position information relating to the position of the chair 8 relative to a starting position, and turn information relating to the detection of completion of each chair rotation, as detected by a position detector circuit (not shown in FIG. 2 but to be discussed further below).

Control panel 54 also operates, in a manner to be described in more detail below, with relay panel 20 so as to control test stimuli, and thus the administration of tests to the subject 2, via control of light spot source 12 and x-y scanning mirrors 14, optokinetic device 16 (stripe cage 76), and flasher 70.

More specifically, relay panel 20 controls the usage of a light spot source 12 (such as a laser) which operates in conjunction with a shutter 66 and x-y scanning mirrors 14 to provide test stimuli comprising a light spot which moves in accordance with a pre-programmed pattern corresponding to desired test stimuli for the particular test being administered (e.g., EOG tracking). Light spot source (or laser) 12 is preferably a Metrologic Laser, Model No. ML-600 or ML-620 (manufactured by Metrologic Instrument, Inc.). The shutter 66—which is a mechanism used to block the laser beam (rather than turning on and turning off the laser beam, which could be detrimental to the laser)—is preferably implemented by a solenoid (Model No. T6x12-C-12v D.C. (manufactured by Guardian, and obtainable from Pfizer Medical Systems of Columbia, Md.)). The solenoid in shutter 66 merely moves a small piece of metal to selectively block and not block the laser beam. Finally, the x-y scanning mirrors 14 are preferably implemented by the following equipment (manufactured by General Scanning, Inc. of Watertown, Mass.): a Series XY-300 Scanning Assembly, two G-330 Galvanometers, an X-7 Mount, and an A-102 Driver Amplifier.

Moreover, relay panel 20 controls a motor 68 which is used to raise and lower a flasher 70, thus placing flasher 70 in position with respect to the subject 2 for the purpose of administering a "flashing light" (VER) test. The flasher 70 is controlled by photostimulator 72 which, in turn, is controlled by the processor 34 via logic section 62 and interface 30. The flasher 70 is preferably implemented by a Photostimulator device, Model PS22 (manufactured by Grass Medical Instruments of Quincy, Mass.).

Finally, the relay panel 20 controls the optokinetic device 16, consisting of a motor 74 which is used to raise and lower a stripe cage 76, such optokinetic device 16 being utilized (for example) in the administration of EOG tests to the subject 2.

Figure 3A:
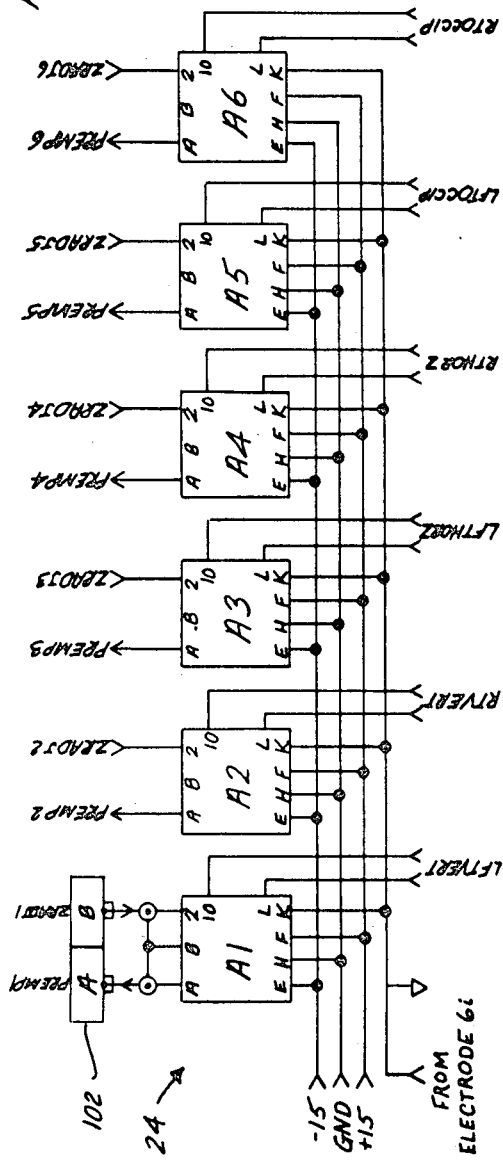
FIG. 3A is a diagrammatic representation of the preamplifier network 24 of the CEOG system of FIG. 2.

FIG. 3A is a diagrammatic representation of the preamplifier network 24 of the CEOG system.

Referring to FIGS. 1, 2 and 3A, the preamplifier network 24—as previously mentioned—is preferably located in the electrode junction box 6 (FIG. 1). Each of the electrodes 6a through 6l is connected to the preamplifier network 24.

More specifically, preamplifier network 24 of FIGS. 1 and 2 basically comprises, with reference to FIG. 3A, amplifiers A1 through A6, each corresponding to a specific pair of electrodes 6a/6b, 6c/6d, . . . connected to the subject 2. Preamplifier network 24 comprises individual preamplifiers A1, A2, . . . , A6 for receiving input test data signals from corresponding pairs of electrodes, and for providing corresponding preamplifier outputs PREMP1, PREMP2, . . . , PREMP6 to the amplifier network 26 (FIG. 2). Preamplifiers A1, A2, . . . , A6 also receive zero-adjustment inputs ZRADJ1, ZRADJ2, . . . , ZRADJ6, resulting from manual bias adjustment by the operator or automatic bias adjustment under the control of the processor 34 (FIG. 2), as will be discussed below relative to FIG. 5.

Thus, electrode test data signals for a particular eye measurement (for example, left vertical eye measurement) are received and provided to the L and 10 terminals of one of the preamplifiers (for example, preamplifier A1). After amplification in preamplifier A1, a preamplifier output is provided (specifically, the preamplifier output of preamplifier A1 is provided as signal PREMP1 via terminal A thereof).

Zero adjustment signals (such as ZRADJ1 corresponding to bias adjustment of preamplifier A1) are received and provided to terminal 2 of the particular preamplifier to be adjusted (in this case, preamplifier A1). ZRADJ1, ZRADJ2, . . . are zero adjustment signals (previously referred to, in FIG. 2, as BIAS signals) received either from amplifier network 26 (in the case of manual bias adjustment) or from processor 34 via the DAC contained in converter stage 56 and the interface 30 (in the case of automatic bias adjustment). This subject will be addressed in further detail below.

Power signals (previously referred to as PWR in FIG. 2)—specifically, +15 volts D.C., −15 volts D.C., and a ground signal GND—are provided to terminals F, E and H, respectively, of the various preamplifiers A1 through A6 as power inputs thereto, terminal K of each preamplifier A1 through A6 being grounded.

Finally, the preferred embodiment includes input-/output connector terminals 102 connected by coaxial cable to respective preamplifiers A1–A6, as shown in FIG. 3A for preamplifier A1 alone. Thus, terminal B of each preamplifier A1–A6 is preferably connected in common to the outer shield of the coaxial cable. This common ground connection arrangement significantly aids common mode rejection, thus eliminating a substantial amount of normally encountered system noise.

FIG. 3B is a detailed schematic of the preamplifiers A1, A2, . . . , A6 of the preamplifier network 24 of FIG. 3A.

Basically, preamplifiers A1, A2, . . . , A6 each comprise an amplifier AMP1, which—in the preferred embodiment—is an AD522 amplifier (manufactured by Analog Devices of Massachusetts). Amplifier AMP1 receives electrode test data signals via terminals L and 10. Such electrode test data signals are applied to terminals 1 and 3, respectively, of amplifier AMP1. Diodes CR1 and CR2 provide amplifier AMP1 with protection from "static discharge."

Capacitors C7 and C8 are provided between terminal L and ground, and terminal 10 and ground, respectively, for the purpose of removing high frequencies occurring in the electrode test data signals. Grounding resistors R13 and R14—provided between terminals L and 10, respectively, and ground—are preferably five megohm resistors which drain off leakage currents from amplifier AMP1 before the electrodes are "plugged in." If this is not done, a voltage (as much as ±15 volts) could accumulate on capacitors C7 and C8, which would cause the patient to receive a shock through the electrodes. Amplifier AMP1 also has an external gain-setting resistor R8 connected between terminals 2 and 14 thereof. Variable resistance P1 is an offset null potential which is adjusted to provide zero volts at terminal 7 of amplifier AMP1 when the inputs (at terminals 1 and 3 thereof) are "shorted." A further supply voltage $-V_{EE}$ is provided to amplifier AMP1 (at terminal 5 thereof). Amplifier AMP1 provides its output PREMPi (i=1, 2, ..., 6) to the amplifier network 26 (FIG. 2).

As mentioned previously with reference to FIG. 3A, each amplifier A1, A2, ..., A6 of preamplifier network 24 may be zero-adjusted by means of respective inputs ZRADJ1, ZRADJ2, ..., ZRADJ6. With reference to FIG. 3B, such signals ZRADJi (i=1, 2, ...) are generated by manual zero-adjustment performed by the operator, and are also automatically generated by processor 34 (via interface 30 and converter stage 56 of FIG. 2).

Such signals ZRADJi (i=1, 2, ...) are applied as inputs (at terminals 2 and 3) to amplifier AMP2, which acts as a current-to-voltage converting amplifier for converting the zero adjustment input current ZARDJi (i=1, 2, ...) to an output voltage $V_{REF}$. Input ZRADJi is derived from circuitry 46' of FIG. 5 (to be discussed below). An input capacitor C9 is provided for the purpose of removing noise from the input signal ZRADJi. Amplifier AMP2 is provided with a feedback RC network, consisting of capacitor C10 (which also removes noise) and resistor R11 connected in parallel between output terminal 6 and input terminal 2 of amplifier AMP2. Supply voltages $+V_{CC}$ and $-V_{EE}$ are supplied to terminals 7 and 4, respectively, of amplifier AMP2, and biasing capacitors C11 and C12 are connected between respective terminals 7 and 4 (of amplifier AMP2) and ground.

Amplifier AMP2—connected as shown and discussed above—converts the zero-adjustment current ZRADJi (i=1, 2, ...) to a voltage output VREF applied to amplifier AMP1 (terminal 11 thereof) for the purpose of bias adjustment.

Supply voltages $+V_{CC}$ and $-V_{EE}$ are provided to amplifier AMP2 by respective circuits 100 and 102 (FIG. 3B). Circuits 100 and 102 consist of RC networks (resistor R1 and capacitors C1 and C3 in the case of circuit 100, and resistor R2 and capacitors C2 and C4 in the case of circuit 102). The latter RC circuits operate on −15 volt and +15 volt inputs, respectively, to derive the supply voltages $-V_{EE}$ and $+V_{CC}$, respectively, while at the same time accomplishing noise decoupling.

Figure 4A:
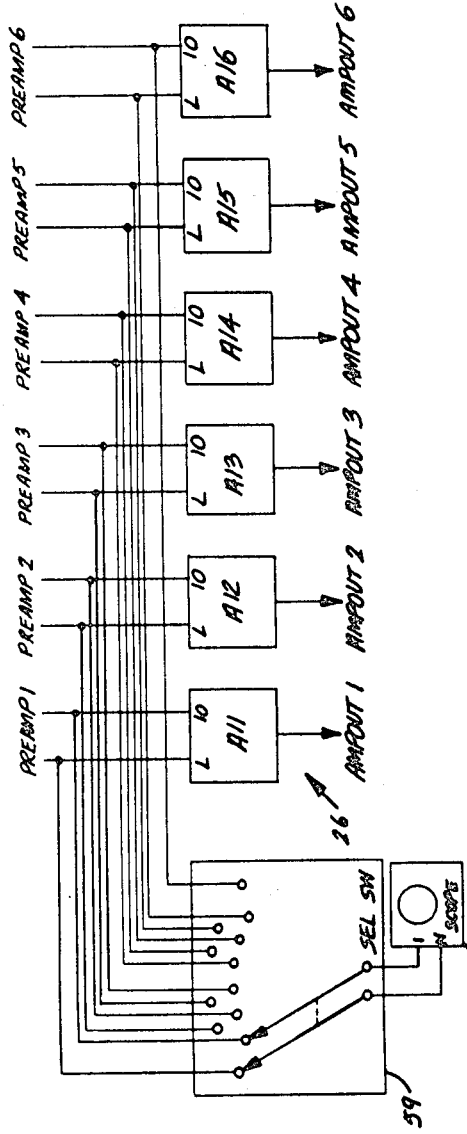
FIG. 4A is a diagrammatic representation of the amplifier network 26 of the CEOG system of FIG. 2.

FIG. 4A is a diagrammatic representation of the amplifier network 26 of the CEOG system.

Amplifier network 26 comprises a plurality of amplifiers A11, A12, ..., A16 for receiving respective preamplifier output signals PREMP1, PREMP2, ..., PREMP6, as shown. Amplifiers A11, ..., A16 amplify the aforementioned respective preamplifier output signals, and provide amplifier output signals AMPOUT1, AMPOUT2, ..., AMPOUT6 corresponding to the electrode test data signals for left vertical eye movement, right vertical eye movement, left horizontal eye movement, right horizontal eye movement, left occipital movement and right occipital movement, respectively. The outputs AMPOUT1, ..., AMPOUT6 are provided to converter stage 56 (FIG. 2).

The inputs PREMP1, PREMP2, ..., PREMP6 are also provided to selector switch 59 which, as shown in FIG. 4A, selects (by operator actuation of the switch) a particular preamplifier output for display on the scope 58. This facilitates broad-range bias adjustment of the preamplifier output signals by affording the operator a visual display of the preamplifier outputs, and thus immediate visual display of the results of the bias adjustment action taken by the operator. Whereas any conventional oscilloscope can be used to implement signal monitor scope 58, scope 58 is preferably a B&K PRECISION Oscilloscope, Model No. 1403A (manufactured by DYNASCAN Corporation of Chicago, Ill.).

Figure 4B:
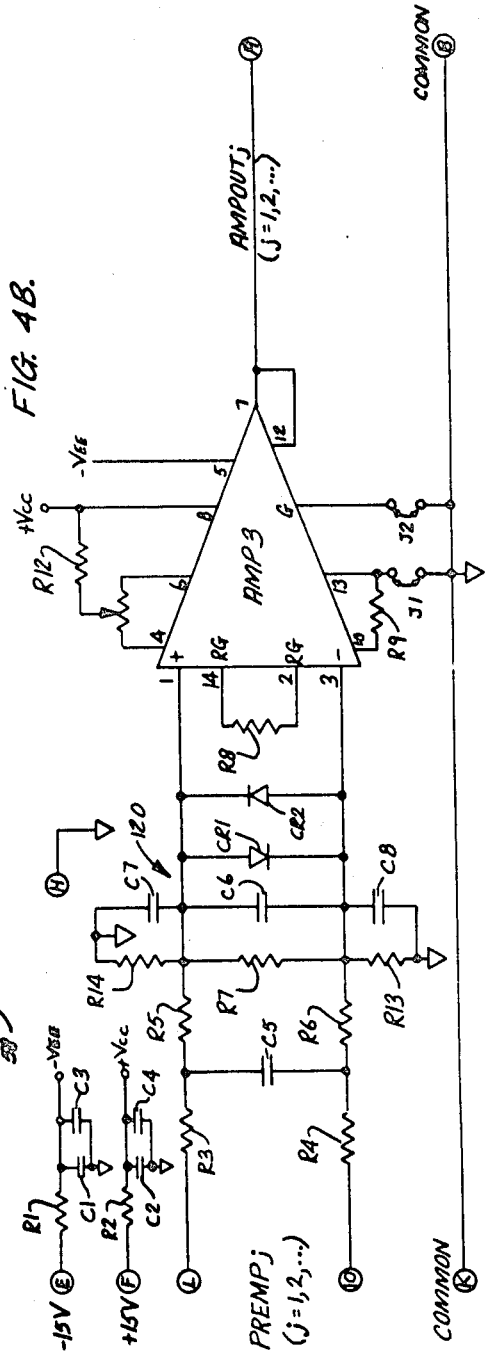
FIG. 4B is a detailed schematic of the amplifiers A11, A12, ..., A16 of the amplifier network 26 of FIG. 4A.

FIG. 4B is a detailed schematic of the amplifiers A11, A12, ..., A16 of the amplifier network 26 of FIG. 4A.

Basically, amplifiers A1j (j=1,2,...) each comprise an amplifier AMP3 which, in the preferred embodiment, is an AD522 amplifier (manufactured by Analog Devices of Massachusetts). It will be noted that the basic amplifier AMP3 constituting the amplifiers A1j in amplifier network 26 (FIG. 4A) is the same as amplifier AMP1 (and AMP2) utilized to constitute the preamplifiers Ai (i=1,2,...) of preamplifier network 24. However, the external connections of amplifier AMP3 (FIG. 4B) differ from those of amplifiers AMP1 and AMP2 (FIG. 3B).

Preamplifier output signals PREMPj (j=1,2,...) are provided via an input network 120 to terminals 1 and 3, respectively, of amplifier AMP3 (FIG. 4B). Specifically, network 120 comprises a series of RC circuits made up of resistor R3 in series with capacitor C5, and resistor R5 in series with capacitor C6, such RC networks being provided for the purpose of filtering the inputs PREMPj. Diodes CR1 and CR2 in input network 120 correspond in function to the similarly designated diodes of the preamplifiers Ai (FIG. 3B). Capacitors C7 and C8 correspond to the similarly designated capacitors in FIG. 3B, and provide the function of high frequency removal during test administration. Resistors R13 and R14 correspond to similarly designated grounding resistors in FIG. 3B.

In the preferred embodiment, differently configured amplifiers can be provided for VER and EOG testing, respectively. For example, where AC coupling is desired, resistors R3 and R4 can be replaced by capacitors.

Amplifier AMP3 receives input PREMPj (j=1,2,...), and amplifies same by a gain factor established by gain-setting resistor R8 (connected at terminals 2 and 14 of amplifier AMP3). As was the case with amplifier AMP1 of FIG. 3B, supply voltages $+V_{CC}$ and $-V_{EE}$ are provided at terminals 8 and 5, respectively, of amplifier AMP3. External adjustment of amplifier AMP3 is provided via variable resistor P1. Amplifier A1j (j=1,2, ...)—specifically, AMP3 thereof—provides the amplifier output AMPOUTj (j=1,2,...) at terminal A, such output AMPj being provided to converter stage 56 (FIG. 2).

FIG. 5 is a diagrammatic representation of biasing circuitry 46' contained in the amplifier network 26 of FIG. 2.

It is to be noted that, whereas FIG. 1 discloses auto-calibration circuitry 46, responsive to the processor 34, for adjusting offsets of individual amplifiers within the preamplifier network 24, in the preferred embodiment of the invention, such auto-calibration functions originate in biasing circuitry in amplifier network 26 (FIG. 2).

Referring to FIG. 5, biasing circuitry 46' basically comprises a plurality of potentiometers POT1, . . . , POT6 for manual adjustment of the bias of individual amplifiers in preamplifier network 24 (FIG. 2), via generation of outputs ZRADJ1, . . . , ZRADJ6. Such manual adjustment of individual amplifiers A1, . . . , A6 of preamplifier network 24 (FIG. 3A) occurs, in the preferred embodiment, when a bias select switch—comprising ganged switches S1, . . . , S6—is in either the AUTO or MANUAL positions. When the bias select switch S1, . . . , S6 is in either position, operator adjustment of POT1-POT6 serves to vary the resistance thereof, which results in variation of the current through resistors R31-R36, thus varying the zero-adjustment current signals ZRADJ1-ZRADJ6.

Automatic adjustment of individual amplifiers in preamplifier network 24 (FIG. 2) is achieved when ganged switch S1, . . . , S6 (FIG. 5) is in the AUTO position. When in the AUTO position, automatic adjustment input signals BIAS1-BIAS6 are received from converter stage 56 (FIG. 2), and such signals BIAS1-BIAS6 contribute, via respective resistors R21-R26, to the generation of zero-adjustment currents ZRADJ1-ZRADJ6.

It is to be noted that, when the bias select switch is in the AUTO position, both automatic and manual adjustment of individual amplifiers in preamplifier network 24 (FIG. 2) can occur, in view of the fact that resistors R21-R26 (relating to automatic adjustment) and resistors R31-R36 (relating to manual adjustment) are connected in parallel under those circumstances. However, when the switch is in the MANUAL position, only manual adjustment of individual amplifiers in preamplifier network 24 (FIG. 2) can occur, in view of the fact that only resistors R31-R36 (relating to manual adjustment) are connected in series with the corresponding potentiometers (POT1-POT6), resistors R21-R26 being maintained in an "open circuit" condition under those circumstances.

By virtue of the above arrangement, the operator of the inventive CEOG system is able to manually adjust the offset voltage of the individual amplifiers in preamplifier network 24 (FIG. 2) via adjustment of particular potentiometers (POT1, POT2, etc.). This enables the operator of the CEOG system to perform broad-range biasing of particular amplifiers—e.g., amplifiers associated with left vertical eye movement, right vertical eye movement, etc.—and thus, to achieve, via such broad-range biasing, elimination of almost all of the D.C. offset voltage associated with the corresponding electrodes attached to the head of the subject. Whereas such manual adjustment can be accomplished as a result of an original or periodic "lineup" of the system, the CEOG system of the present invention also provides automatic, narrow-range biasing of the individual amplifiers in preamplifier network 24 (FIG. 2). Such automatic, narrow-range biasing of the individual amplifiers in the network 24 is achieved by generation, in processor 34 (FIG. 2) of BIAS signals, such BIAS signals being provided—via interface 30 and converter stage 56—to the biasing circuitry 46' (FIG. 5). Such BIAS inputs (BIAS1, BIAS2, . . .) contribute to output adjustment signals ZRADJ1, ZRADJ2, etc., and elimination of the remainder of the D.C. offset voltage associated with the corresponding electrodes is thus automatically achieved.

Figure 6E:
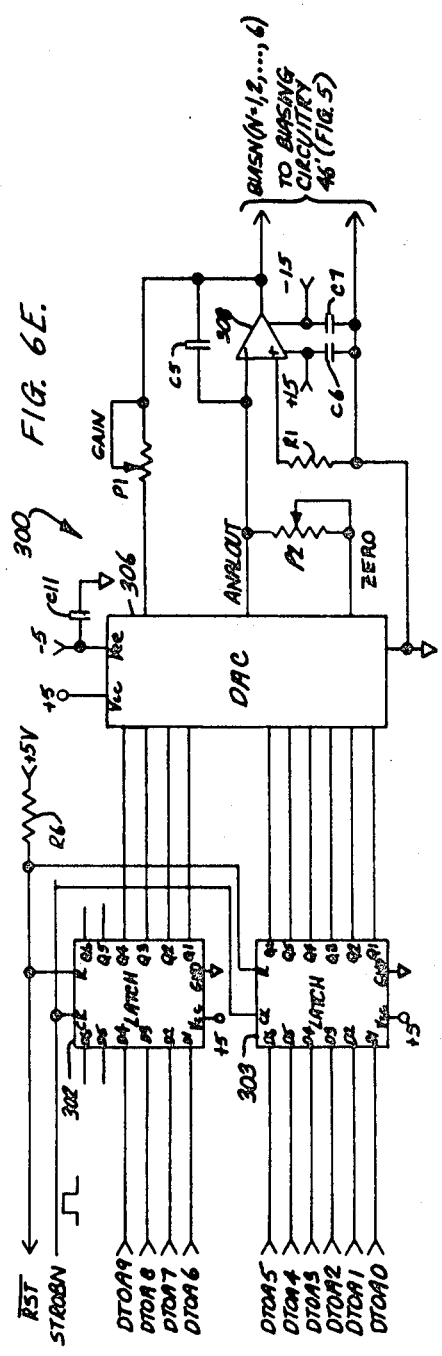
FIG. 6E is a detailed schematic diagram of the DAC portion 300 of the converter stage 56 of the CEOG system of FIG. 2.
Figure 6A:
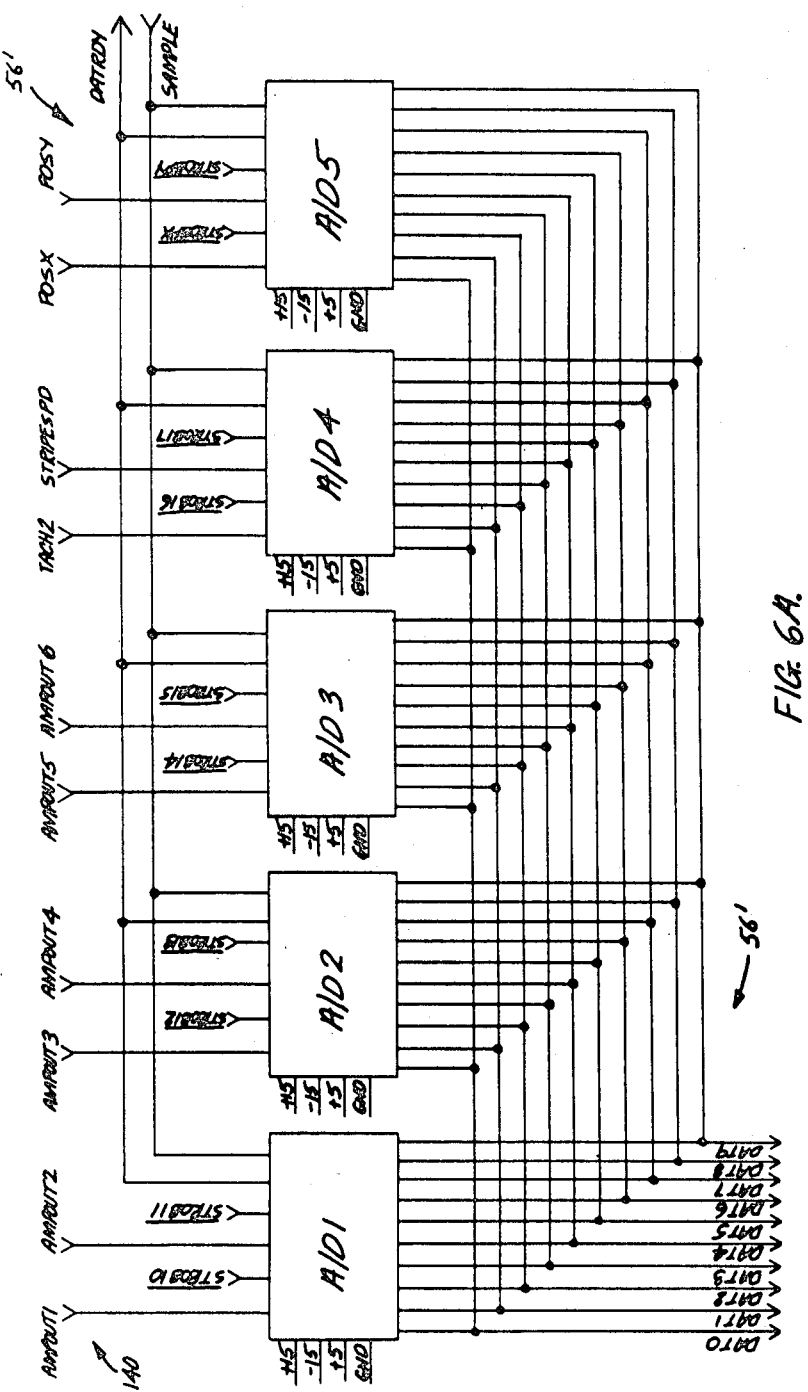
FIG. 6A is a diagrammatic representation of the ADC portion 56' of the converter stage 56 of the CEOG system of FIG. 2.

FIG. 6A is a diagrammatic representation of the ADC portion 56' of the converter stage 56 of FIG. 2. The ADC portion 56' of converter stage 56 (FIG. 2) includes a plurality of ADC's—designated A/D1, A/D2 and A/D3—for receiving pairs of analog electrode test data input signals AMPOUT1/AMPOUT2, AMPOUT3/AMPOUT4 and AMPOUT5/AMPOUT6, respectively, from amplifiers A11, A12, . . . , A16, respectively, of amplifier network 26 (FIG. 4A), and for converting these analog inputs to respective digital outputs DAT0-DAT9. More specifically, converters A/D1-A/D5 are clocked by a timing clock input SAMPLE, and this causes each converter to convert its respective analog input signal (AMPOUT1, AMPOUT2, etc.) to a 10-bit digital word which is stored in an internal buffer in the particular converter A/D1-A/D5. Then, upon generation of inputs $\overline{STROBI0}$-$\overline{STROBI7}$, $\overline{STROBX}$ and $\overline{STROBY}$ by the computer processor 34 (FIG. 2), converters A/D1-A/D5 gate the data from the internal buffer onto the output channel, at the appropriate time, constituting the digital output DAT0-DAT9, Futhermore, the ADC portion 56' includes a further converter A/D4 for receiving and converting, to digital form, analog signals TACH2 (relating to the speed of motor 50 (FIG. 2) which drives the chair 8), and STRIPESPD (relating to the speed of the motor 74 which drives the stripe cage 76 in optokinetic device 16 (FIG. 2)). Finally, the ADC portion 56' of FIG. 6A includes an additional converter A/D5 for receiving and converting, to digital form, analog signals POSX and POSY (relating to the X and Y positions of the mirrors 14 (FIG. 2)). Analog signal TACH2 is provided to converter stage 56 by motor controller 52, via control panel 54 and logic section 62 (FIG. 2); analog signal STRIPESPD is provided by control panel 54 directly to converter stage 56; and analog signals POSX and POSY are provided by relay panel 20 to converter stage 56 via control panel 54 and logic section 62 (FIG. 2).

Finally, as will be seen below, each converter A/D1-A/D5 receives an input SAMPLE which causes the commencement of the conversion of analog data to digital form. When all conversions are complete, output DATRDY is generated as an output. These two control signals will be discussed further below."

Figure 6B:
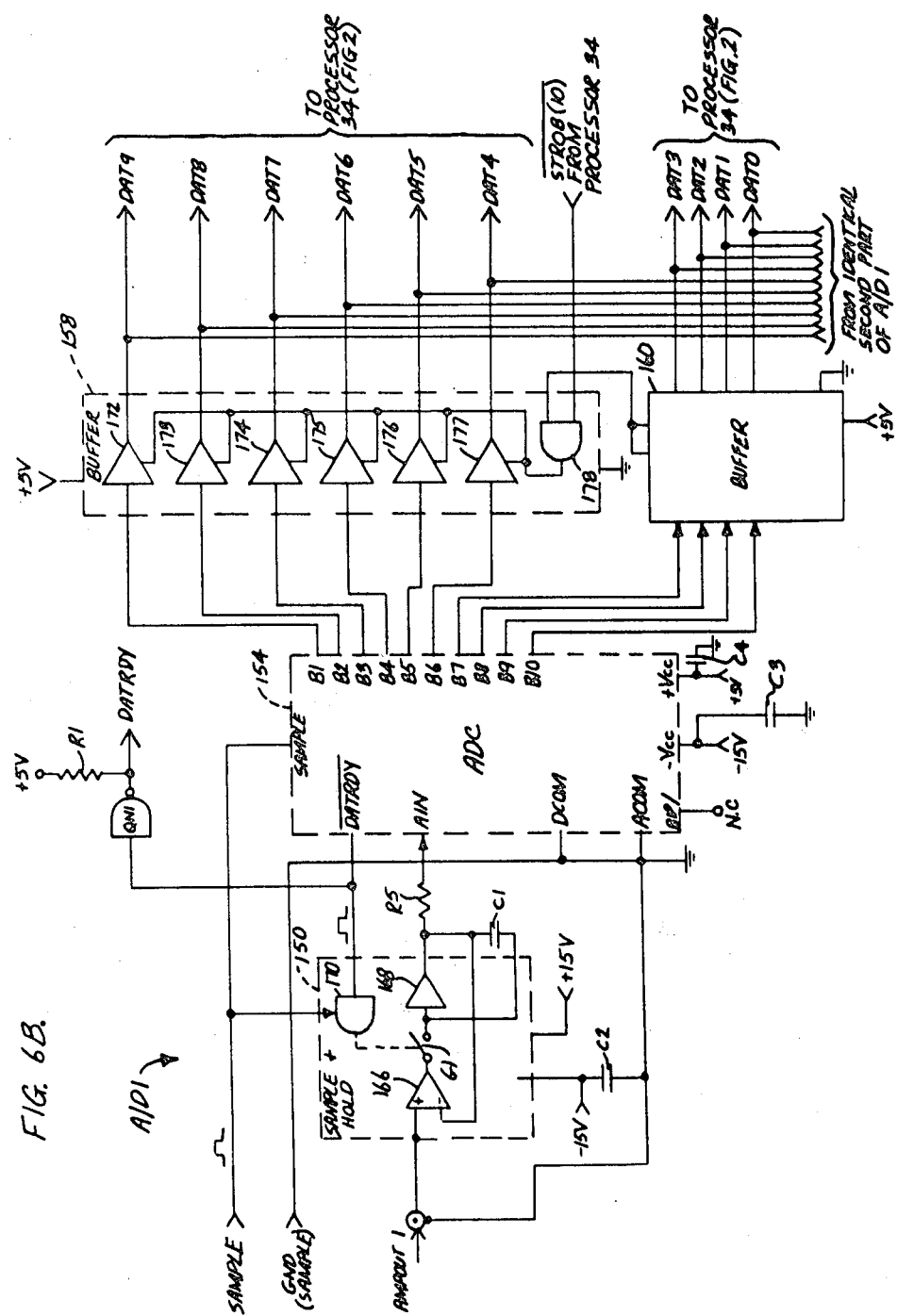
FIG. 6B is a detailed schematic of one-half of the converter A/D1 of FIG. 6A.

FIG. 6B is a detailed schematic of one half of the converter A/D1 of FIG. 6A. It is to be understood that the other half of converter A/D1 is identical in structure to the first half shown in FIG. 6B. Moreover, it is to be further understood that each converter A/D2-A/D5 is identically configured to converter A/D1.

Converter A/D1—that is, each half thereof—basically comprises sample and hold circuit 150, ADC device 154, and buffers 158 and 160. Sample and hold circuit 150 comprises amplifiers 166 and 168, and AND gate 170, configured as shown. Sample and hold circuit 150 is preferably an AD582 device (manufactured by Analog Devices). Moreover, ADC device 154 is a conventional analog-to-digital converting device, but is preferably an AD571 device (manufactured by Analog Devices).

Finally, buffers 158 and 160 include tristate amplifiers 172 through 177 and AND gate 178, configured as shown. That is to say, when the output of gate 178 is "low," the outputs of amplifiers 172 through 177 are open circuits; when the output of gate 178 is "high," the outputs of amplifiers 172, 173, . . . are the same as input signals B1, B2, . . . from ADC154. Preferably, buffers 158 and 160 are hex/tristate buffers, Model Nos. SN74LS365 or SN74365 (manufactured by Texas Instruments).

In operation, output AMPOUT1 is received from amplifier network 26 (FIG. 2) by sample and hold circuit 150. Signal DATRDY is normally "high," and signal SAMPLE is normally "low." When SAMPLE goes "high," signal $\overline{\text{DATRDY}}$ also goes "high," and gate G1 in sample and hole 150 closes, so that the voltage at AMPOUT1 appears at the input to amplifier 168. Single AMPOUT1 then appears at the output of amplifier 168, and thus on both sides of capacitor C1. When SAMPLE goes "low," gate G1 opens (and stays open until both SAMPLE and $\overline{\text{DATRDY}}$ are both "high"), leaving the AMPOUT1 voltage at the output of amplifier 168 even though AMPOUT1 may change during the analog-to-digital conversion in ADC154. Thus, when gate G1 is closed, the signal AMPOUT1 is sampled (acquired), and when gate G1 opens, the sampled (acquired) input signal is held at the AIN terminal of ADC154.

ADC device 154 performs digital conversion of the analog input AMPOUT1 in response to receipt of signal SAMPLE from ADC logic circuitry 200 going "low" (FIG. 6D), to be discussed below. During the digital conversion process, ADC device 154 holds output $\overline{\text{DATRDY}}$ to the "high" condition, thus making $\overline{\text{DATRDY}}$ "low." Once conversion is completed, however, ADC device 154 generates a "low" output $\overline{\text{DATRDY}}$. It is to be noted that, in order for output DATRDY to go "high," each of the two ADC devices 154 in each converter A/D1, . . . , A/D6 must generate a "low" output at terminal $\overline{\text{DATRDY}}$. This will allow the output DATRDY (subsequently provided to ADC logic circuitry 200 (FIG. 6D)) to go "high."

Digital bit outputs B1 through B6 are provided to respective tristate buffers 172 through 177 in hex buffer 158, while digital bit outputs B7 through B10 are provided to corresponding buffers (not shown) in buffer 160. In addition, buffers 172 through 177 of buffer 158 (and corresponding buffers (not shown) in buffer 160) are of the type that look like an open circuit at the output until receipt of a clock-type signal. Specifically, as will be seen below, processor 34 (FIG. 2) provides address input signals to ADC address decoding logic 190 (FIG. 6C), which generates clock-type signals $\overline{\text{STROB10}}$, $\overline{\text{STROB11}}$, . . . (as will be explained in detail below). Thus, $\overline{\text{STROB10}}$ is provided to buffers 158 and 160, which transmit the buffered digital bit data, via interface 30, to processor 34 (FIG. 2), as outputs DAT0 through DAT9.

Finally, it should be noted again that FIG. 6B is a detailed schematic of one half of converter A/D1 of FIG. 6A, and further, that each of converters A/D2-A/D5 are configured identically to converter A/D1. As should be clear from the above explanation, the first halves of A/D1-A/D5 release their digital output DAT0-DAT9 in response to respective clock-type inputs $\overline{\text{STROB10}}$, . . . , $\overline{\text{STROB16}}$, $\overline{\text{STROBPX}}$ (see FIG. 6A), while the second halves of converters A/D1-A/D5 release digital data DAT0-DAT9 in response to respective clock-type inputs $\overline{\text{STROB11}}$, . . . , $\overline{\text{STROB17}}$, $\overline{\text{STROBPY}}$.

Figure 6C:
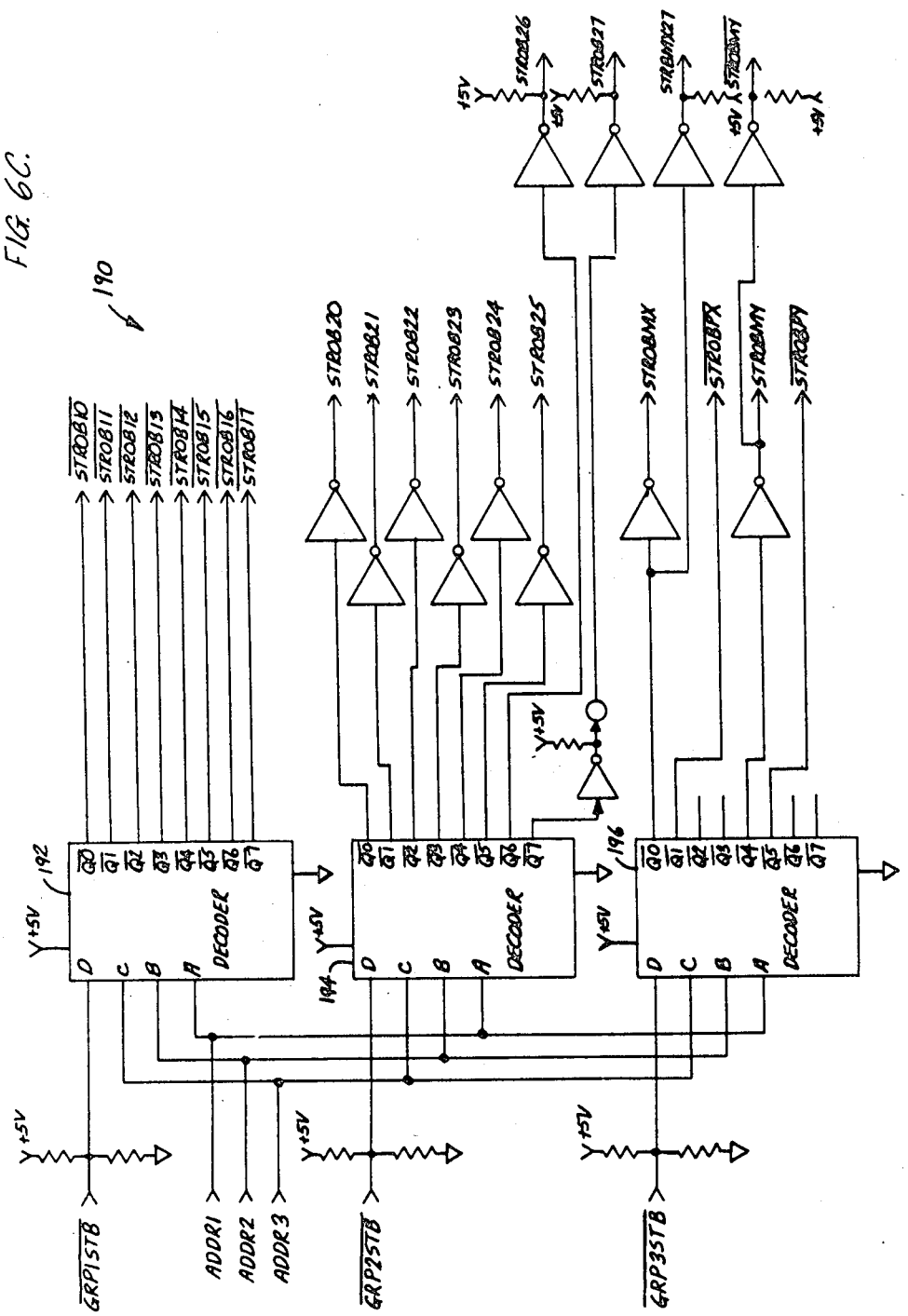
FIG. 6C is a diagrammatic representation of address decoding logic 190 in converter stage 56 of the CEOG system of FIG. 2.

FIG. 6C is a diagrammatic representation of address decoding logic 190 in converter stage 56 of FIG. 2.

Specifically, logic 190 basically comprises binary/octal decoder circuits 192, 194 and 196. Principal inputs to the logic 190 are address inputs ADDR1, ADDR2 and ADDR3, and further inputs $\overline{\text{GRP1STB}}$, $\overline{\text{GRP2STB}}$ and $\overline{\text{GRP3STB}}$.

Binary/octal decoder 192 responds to receipt of signal inputs $\overline{\text{GRP1STB}}$ (acting as a decoding clock signal) and inputs ADDR1-ADDR3 to perform octal conversion, selectively actuating one of the eight outputs $\overline{\text{Q0}}$ through $\overline{\text{Q7}}$ in correspondence to the particular decoder input. In this manner, previously discussed clock-type outputs, $\overline{\text{STROB10}}$–$\overline{\text{STROB17}}$, are obtained. $\overline{\text{STROB10}}$–$\overline{\text{STROB17}}$ are, it will be recalled, clock-type signals provided to respective converter devices A/D1, A/D2, . . . in the ADC portion 56' of converter stage 56 (see FIG. 6A).

Similarly, binary/octal decoder 194 responds to receipt of signal inputs $\overline{\text{GRP2STB}}$ and ADDR1-ADDR3 to perform octal conversion, thus actuating a selected one of the outputs $\overline{\text{Q0}}$ through $\overline{\text{Q7}}$ correspondence to the particular decoder inputs. Thus, clock-type outputs $\overline{\text{STROB20}}$–$\overline{\text{STROB27}}$ are obtained, and these clock-type outputs (as will be discussed subsequently) are utilized in the DAC portion of the converter stage 56 (FIG. 2).

Finally, binary/octal decoder 196 responds to receipt of signal inputs $\overline{\text{GRP3STB}}$ and ADDR1-ADDR3 to perform octal conversion, thus actuating a selected one of the outputs $\overline{\text{Q0}}$ through $\overline{\text{Q7}}$ in correspondence to the particular decoder inputs. Thus, clock-type outputs $\overline{\text{STROBMX}}$ and $\overline{\text{STROBMY}}$ are obtained, and these clock-type outputs (as will be discussed below) are utilized as clock-type inputs to the DAC circuitry 300 (FIG. 6E). Moreover, decoder 196 (FIG. 6C) generates clock-type outputs $\overline{\text{STROBPX}}$ and $\overline{\text{STROBPY}}$ which are clock-type inputs provided to A/D5 (FIG. 6A).

Although any binary/octal converter circuitry may be utilized to implement binary/octal decoders 192, 194 and 196 of FIG. 6C, binary/octal decoders 192, 194 and 196 are preferably SN74LS42 converter circuits (manufactured by Texas Instruments).

FIG. 6D is a detailed schematic diagram of further ADC logic circuity 200 and 250 of the converter stage 56 of FIG. 2.

Logic circuitry 200 consists of a timer 202 (preferably, a one-second timer) which responds to "turn on" of the system by generating—via inverter 204—an output $\overline{\text{RST}}$ utilized to reset the A/D and D/A systems. In particular, output $\overline{\text{RST}}$ is utilized to reset certain latch circuits 302-305 contained in the DAC circuitry 300 (FIG. 6E) to be discussed below.

Logic 250 (FIG. 6D) basically comprises NAND gate 252 and one-shot devices 254 and 256. NAND gate 252 detects the occurrence of either input $\overline{\text{CMPSAMP}}$ (a one-bit (specifically, bit number 14) input from interface 30 of FIG. 2) or $\overline{\text{3MSSAMP}}$ (an input from logic section 62 of FIG. 2), and triggers the one-shot device 254 to provide output SAMPLE, transmitted to the ADC device 154 in each converter A/D1-A/D5 (FIGS. 6A and 6B). As will be recalled, the trailing edge of signal SAMPLE causes each ADC device 154 to start the conversion process.

As will also be recalled, upon completion of the conversion process in all ADC devices 154, output DATRDY is permitted to go "high." This triggers one-shot device 256 (FIG. 6D) which, in turn, results in generation of output $\overline{\text{SNDDAT}}$, transmitted to the processor 34 via interface 30 (FIG. 2). By means of the output $\overline{\text{SNDDAT}}$, the processor 34 becomes aware of the fact that digital data—now converted from analog form—is ready for transmission to the computer processor 34. Accordingly, processor 34 transmits—via interface 30—appropriate decoder inputs $\overline{\text{GRP1STB}}$ (or $\overline{\text{GRP2STB}}$, or $\overline{\text{GRP3STB}}$), and ADDR1-ADDR3, as a result of which address decoding logic 190 (FIG. 6C) issues appropriate clock-type outputs (any one of $\overline{\text{STROBI0}}$–$\overline{\text{STROBI7}}$, $\overline{\text{STROBPX}}$, $\overline{\text{STROBPY}}$) so as to cause the digital data to be transmitted to the processor 34 by the appropriate converter A/D1, ..., A/D5 (FIG. 6A).

FIG. 6E is a detailed schematic diagram of the DAC portion 300 of the converter stage 56 of FIG. 2.

Basically, the DAC portion 300 comprises latch circuits 302 and 303, DAC device 306, and associated amplifier 308. In operation, latch circuits 302 and 303 are reset by input $\overline{\text{RST}}$ applied to the R terminals of each. Then, in response to a clock-type input $\overline{\text{STROBN}}$ applied to the CK terminals thereof, each of latch circuits 302 and 303 receives and latches digital data DTOA6–DTOA9 and DTOA0–DTOA5, respectively, from the processor 34 (FIG. 2) applied thereto.

Whereas any conventional latch circuit may be utilized to implement latch circuits 302 and 303 in FIG. 6F, latch circuits 302 and 303 are preferably 74LS174 latch devices (manufactured by Texas Instruments).

DAC device 306 operates in conjunction with latch circuits 302 and 303 to receive latch outputs Q1–Q4 from latch circuit 302 and latch outputs Q1–Q6 from latch circuit 303. DAC 306 then performs digital-to-analog conversion to produce the analog output signal ANALOUT, which is provided to amplifier 308. Amplifier 308 performs current-to-voltage conversion of the ANALOUT output of DAC device 306 to produce output voltage signal BIASN (N=1,2,...,6), the latter being provided to the biasing circuit 46' of FIG. 5 (previously discussed above).

Whereas any conventional digital-to-analog converting device may be used to implement DAC device 306, DAC device 306 is preferably an AD561J converter device (manufactured by Analog Devices of Massachusetts). Accordingly, DAC 306 is provided with supply voltages $V_{CC}$ and $V_{EE}$ (+5 and −15 volts, respectively). The gain and bias of the outputs of the DAC device 306 are externally set by potentiometers P1 and P4, respectively.

Finally, whereas any conventional operational amplifier may be utilized to implement amplifier 308 of FIG. 6E, amplifier 308 is preferably a UA741 amplifier (manufactured by Analog Devices of Massachusetts). Accordingly, amplifier 308 is supplied with +15 volt and −15 volt supply voltages. Whereas analog output ANALOUT is provided to terminal 2 of amplifier 308, the terminal 3 thereof is connected to ground via grounding resistor R1. Moreover, the output of amplifier 308—besides being connected in a "feedback" arrangement to the DAC device 306 (via potentiometer P1)—is also feedback-connected to its terminal 2 input via feedback capacitor C5. Finally, amplifier 308 is provided with bypass capacitors C6 and C7.

Whereas FIG. 6E and the associated description above describe the DAC circuitry 300 as comprising a pair of latch circuits 302 and 303, a single DAC device 306 and a single amplifier 308, the DAC circuitry 300 preferably includes an additional pair of latch circuits, an additional DAC device, and an additional amplifier, so as to provide dual-channel outputs. In such a preferred arrangement, the output BIASN (N=1, 3, 5) would provide for bias adjustment of the odd-numbered preamplifiers in preamplifier network 24, while the output of the second portion of DAC circuitry 300—designated BIASM (M=2, 4, 6)—would service the even-numbered preamplifiers in preamplifier network 24.

To summarize, processor 34 (FIG. 2) provides digital signals DTOA0–DTOA9 (FIG. 6F)—via latch circuits 302 and 303—to DAC device 306, wherein analog conversion takes place. The resulting analog output ANALOUT—after current-to-voltage conversion in amplifier 308—provides an output voltage signal BIASN. As explained above, in the preferred embodiment, output BIASN (N=1, 3, 5) adjusts the bias of the odd-numbered preamplifiers in preamplifier network 24 (FIG. 2), while an additional output signal BIASM (M=2, 4, 6) adjusts the bias of the even-numbered preamplifiers.

Figure 7A:
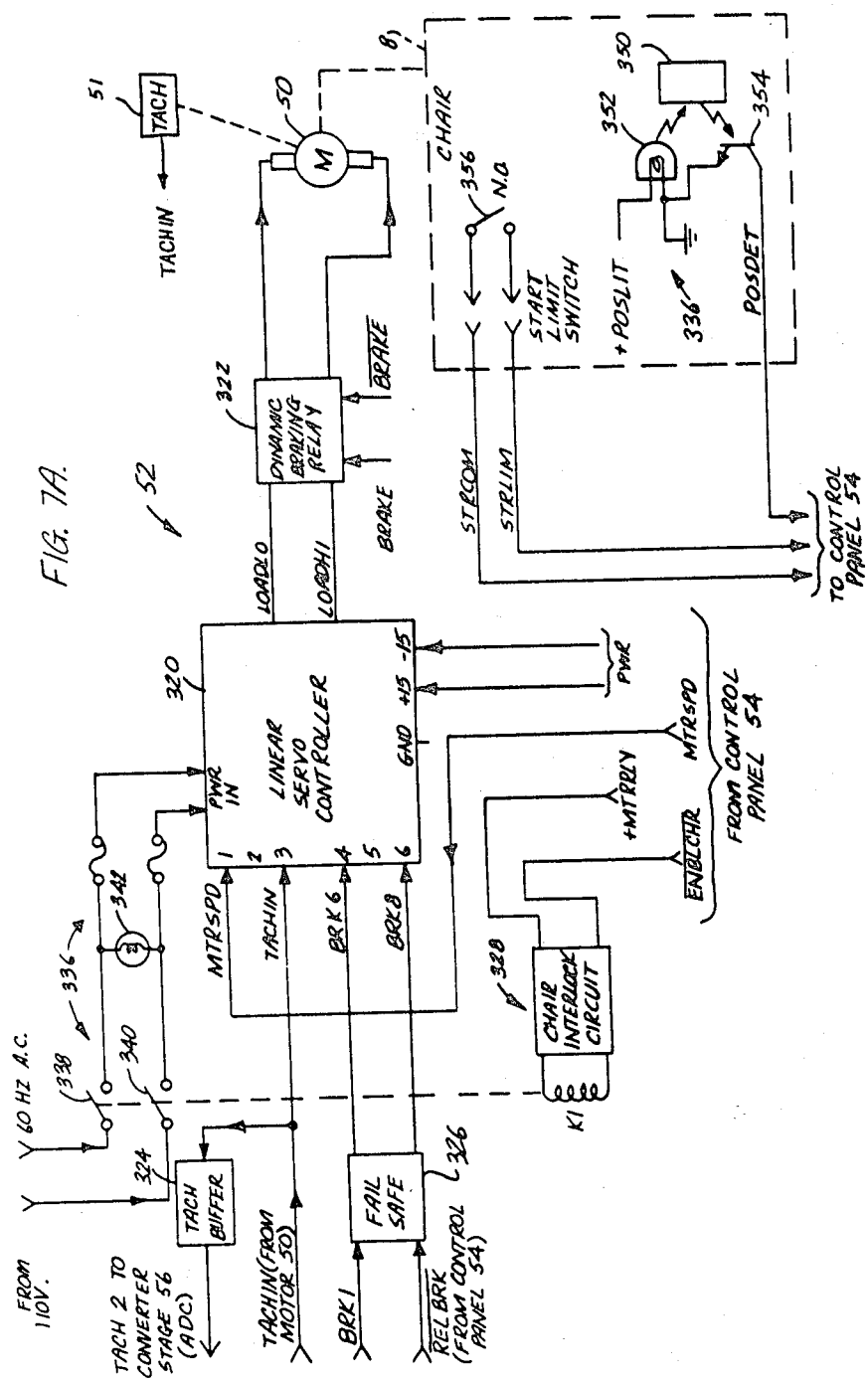
FIG. 7A is a diagrammatic representation of the motor controller 52 of the CEOG system of FIG. 2.

FIG. 7A is a diagrammatic representation of the motor controller 52 of the CEOG system.

Motor controller 52 basically comprises a linear servo controller 320, a dynamic breaking relay 322, tach (motor speed) buffer 324, brake command input (fail safe) circuitry 326, and chair interlock circuitry 328.

In operation, linear servo controller 320 receives a control signal MTRSPD, provided by control panel 54 (FIG. 2), but originating in logic section 62 as a result of operator selection. Linear servo controller 320 also receives a tachometer input signal TACHIN from tachometer 51 associated with the motor 50 (FIG. 2), indicating actual speed of the motor 50. Linear servo controller 320 then performs, in a conventional manner, a comparison operation of actual motor speed (TACHIN) with desired motor speed (MTRSPD), and—as a result of such comparison—controller 320 generates appropriate motor-controlling current (LOADLO/LOADHI) signals. The motor-controlling currents are provided through dynamic braking relay 322 to motor 50 so as to control the speed of operation thereof by increasing or decreasing the speed of the motor 50, and thus the rotational speed of the chair 8 (FIG. 2).

The tachometer input signal TACHIN provided to linear servo controller 320 is also provided to tach buffer 324, from which analog signal TACH2 is provided to the ADC portion 56' of converter stage 56 (FIGS. 2 and 6A) for subsequent digital conversion, and provision to processor 34 via interface 30. In this manner, the processor 34 is kept apprised of the actual speed of the motor-driven chair 8. Tach buffer 324 can be any conventional buffer amplifier, as is well known to on of ordinary skill in the art.

Linear servo controller 320 also receives—at terminals 4 and 6 thereof—respective brake command signals BRK6 and BRK8, these brake command signals being provided by fail safe circuitry 326. Linear servo controller 320 responds to the brake command input signals BRK6 and BRK8 in a conventional manner to force the motor-controlling current from controller 320 to zero during the braking operation.

In the preferred embodiment, input signals BRK6 and BRK8 are outputs of the fail safe circuit 326, which circuit 326 receives inputs BRK1 and $\overline{\text{RELBRK}}$ from control panel 54 (FIG. 2).

Figure 7B:
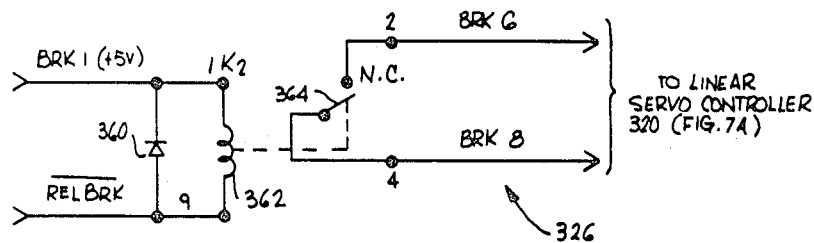
FIG. 7B is a detailed schematic diagram of the failsafe circuit 326 of FIG. 7A.

FIG. 7B is a detailed schematic diagram of the fail-safe circuit 326 of FIG. 7A. Input signal BRK1 is received from logic section 62 (FIG. 2) via control panel 54, and is always maintained at a "high" level (for example, +5 volts). Input signal $\overline{RELBRK}$ is normally maintained "high," so that solenoid 362 is non-actuated, and switch 364 is normally closed. This forces controller 320 (FIG. 7A) to put out zero amps at the LOADLO/LOADHI outputs thereof.

However, when $\overline{RELBRK}$ goes "low," solenoid 362 is actuated, causing normally closed switch 364 to open, and the open-circuited inputs BRK6 and BRK8 to linear servo controller 320 (FIG. 7A) cause linear servo controller 320 to adjust the speed of motor 50 so as to bring actual motor speed (TACHIN) into coincidence with desired motor speed (MTRSPD).

Figure 7C:
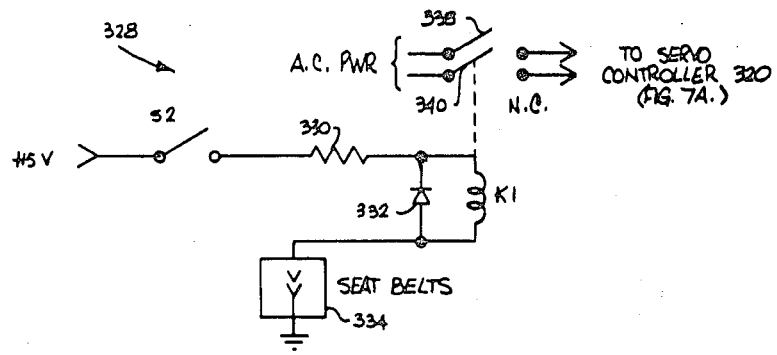
FIG. 7C is a detailed schematic of the chair interlock circuitry 328 of FIG. 7A.

FIG. 7C is a detailed schematic of the chair interlock circuitry 328 of FIG. 7A. Basically, chair interlock circuit 328 comprises resistor 330, transient diode 332 and solenoid K1—arranged as shown in FIG. 7C—and connected, as shown, both to A.C. power switches 338 and 340 (FIG. 7A), and to seat belts 334 (located on the chair 8 (FIG. 2)).

In operation, actuation of switch $S_2$ (the chair motor "on" switch which, as will be seen below, is located on an operator control section of control panel 54 of FIG. 2) causes application of a positive D.C. voltage to solenoid K1 via resistor 330, solenoid K1 actuating A.C. power switches 338 and 340 to the closed position, thus providing A.C. power to the servo controller 320 (FIG. 7A). However, it is to be noted that, as a result of operation of the chair interlock circuit 328, solenoid K1 will not be actuated unless the seat belts 334 (located at the chair 8 of FIG. 2) are connected, thus closing the circuit between the positive D.C. voltage and ground. In this manner, the chair 8 is equipped with a safety feature whereby A.C. power to the servo controller 320, and thus to the motor 50, will be interrupted should the subject seated in the chair 8 unfasten the seat belts 334.

Motor controller 52 further includes position detection circuitry 336 which, in actual implementation, is located on the chair 8 (FIG. 7A). Specifically, the chair 8 is equipped with a reflective plate 350 which reflects light received from lamp 352 (actuated by a voltage +POSLIT), causing the reflected light to impinge on photodetector 354 so as to generate chair position information POSDET, which information passes through motor controller 52 and control panel 54 (FIG. 2) to logic section 62. Signal POSDET indicates that the chair 8 is at a position 90 degrees to the right of its "normal" position.

Motor controller 52 (FIG. 7A) also includes a start limit switch 356 (normally open) which, in actual implementation, is located on the chair 8 (FIG. 7A). Start limit switch 356, when open, allows signal STRLIM to be "high." However, inasmuch as line STRCOM represents a ground connection, when start limit switch 356 is closed, STRLIM goes "low," and this "low" condition is transmitted via control panel 54 (FIG. 2) to logic section 62. As will be seen below, upon operator reset of the system, if start limit switch 356 is open, as indicated by a "high" STRLIM signal, the chair 8 will automatically, under system control, move to its "normal" position, which is attained when the limit switch 356 closes.

Figure 7D:
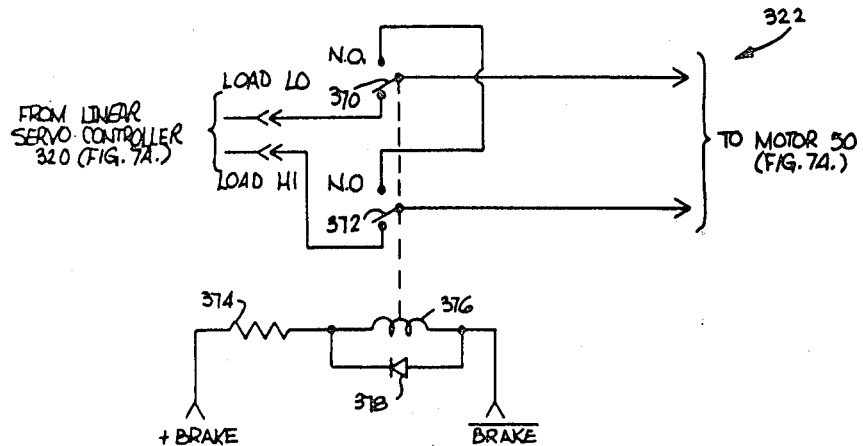
FIG. 7D is a detailed schematic diagram of the dynamic braking relay 322 of FIG. 7A.

FIG. 7D is a detailed schematic diagram of the dynamic braking relay 322 of FIG. 7A. Dynamic braking relay circuit 322 basically comprises relay switches 370 and 372, series-connected resistor 374, actuating solenoid 376, and transient diode 378.

In operation, relay switches 370 and 372 are normally in the downward position so as to pass the LOADLO/LOADHI control current signal of controller 320 to motor 50 (FIG. 7A). Input +BRAKE is maintained at a positive voltage ("high") level and relay switches 370 and 372 remain in the normal downward position. Once $\overline{BRAKE}$ goes "low," however, solenoid 376 is actuated, and forces switches 370 and 372 into the upward position. This not only interrupts the provision of control currents signal LOADLO/LOADHI to the motor 50, but also achieves a dynamic braking effect by short-circuiting the input terminals to motor 50, via the short-circuit connection established between switches 370 and 372.

Figure 8:
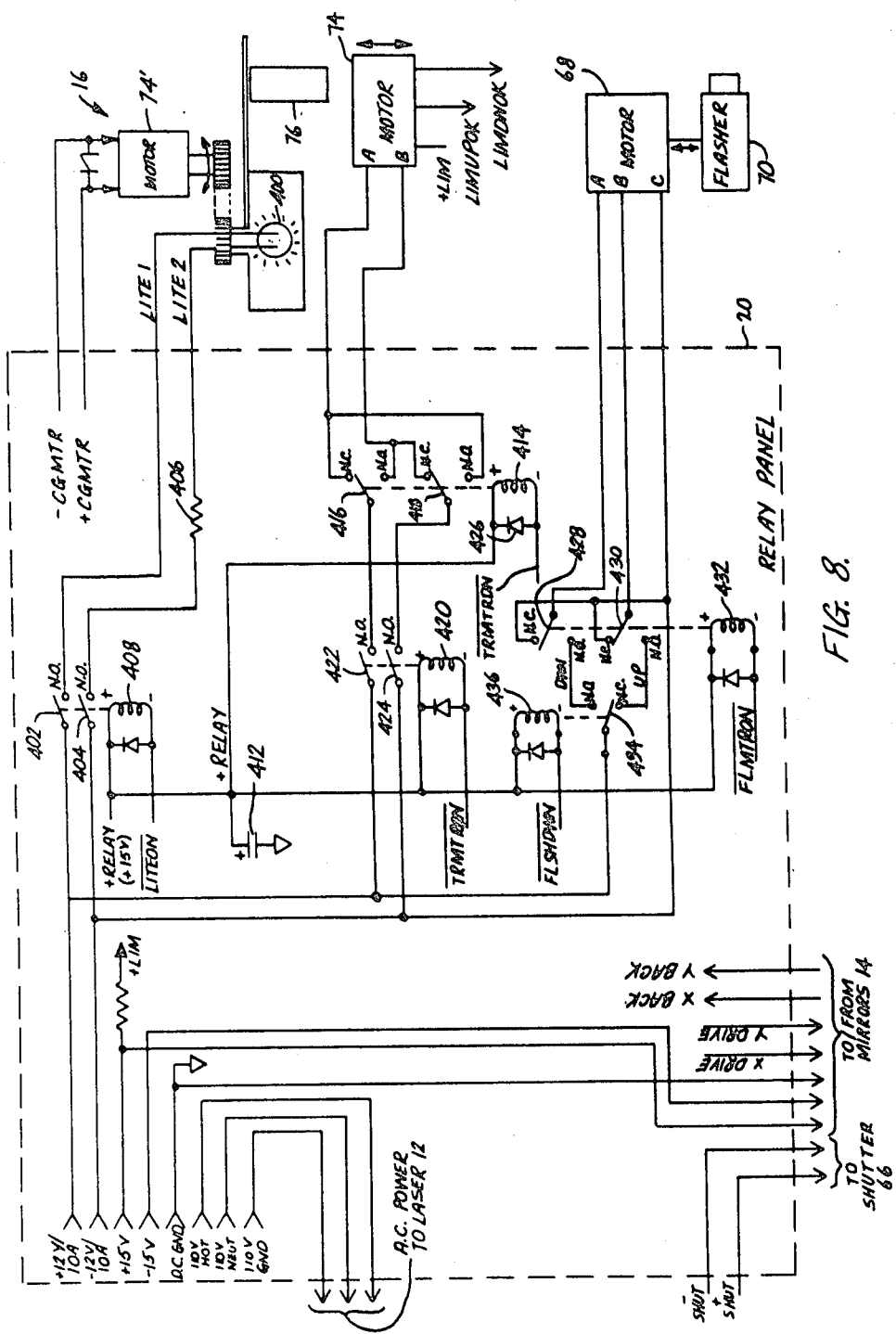
FIG. 8 is a diagrammatic representation of the relay panel 20 of the CEOG system of FIG. 2.

FIG. 8 is a diagrammatic representation of the relay panel 20 of the CEOG system.

In general, relay panel 20 receives various input control signals from control panel 54 and logic section 62 (FIG. 2), and in response thereto, controls the operations of the light source 12, mirrors 14, shutter 66, optokinetic device 16 (comprising motors 74 and 74' and stripe cage 76), the flasher motor 68 and flasher 70. In addition, relay panel 20 receives feedback signals (XBACK and YBACK) from the mirrors 14, and provides these feedback signals, via control panel 54, to logic section 62, wherein—as will be subsequently described—compensation for the distortion of the light source projection on the cylindrical walls 18 (FIG. 1) of the test station 4 is achieved.

Relay panel 20 receives various D.C. voltage inputs (+12 v. and +15 v.), and an A.C. input (110 v.). The A.C. input to relay panel 20 is merely passed therethrough, so as to provide A.C. power to the laser 12 (FIG. 2). The 12 v. D.C. input is provided, via relay switches 402 and 404 and resistor 406, as inputs (LITE1 and LITE2) to the lamp 400 which illuminates the stripe cage 76 (FIG. 2). Specifically, relay switches 402 and 404, which are normally in the open position, are actuated to the closed position by solenoid 408 when $\overline{LITEON}$ (received from logic section 62) goes "low." On the other hand, in response to $\overline{LITEON}$ going "high," solenoid 408 is off, and switches 402 and 404 return to the normally open position, interrupting D.C. power supply to the lamp 400. It is to be noted that relay panel 20 includes a capacitor 412 having its positive terminal connected to power input +RELAY. Capacitor 412 acts as a noise-prevention filter for the +RELAY input (a positive voltage—for example, 15 volts).

Further referring to FIG. 8, relay panel 20 includes switches 422 and 424 which remain in the normally open position so long as input $\overline{TRMTRON}$ (from logic section 62 of FIG. 2) is "high." However, in response to signal $\overline{TRMTRON}$ going "low" (thus commanding turn-on of the stripe cage motor 74), solenoid 420 causes switches 422 and 424 to close, thus defining paths for the input of +12 volts and its return, respectively.

The aforementioned power input paths include switches 416 and 418 which are normally (so long as $\overline{TRMTRDN}$ from logic section 62 remain "high") in the upward position, so that +12 volts and its return are provided to input terminals A and B, respectively, of motor 74. This power input to motor 74 raises, or maintains in the raised position, the stripe cage 76 of optokinetic device 16.

However, when lowering of the stripe cage 76 is commanded by the operator (in a manner to be described below with reference to FIG. 9A), input signal $\overline{TRMTRDN}$ goes "low," resulting in actuation of switches 416 and 418 (by solenoid 414) to the downward position. This effectively reverses the polarity of D.C. input, so that +12 volts and its return are provided to terminals B and A, respectively, of motor 74. Accordingly, motor 74 operates in the reverse direction to lower the stripe cage 76 of optokinetic device 16.

Moreover, motor 74 generates status output signals LIMUPOK or LIMDNOK when the stripe cage 76 is raised to its upper limit or lowered to its lower limit, respectively.

Relay panel 20 also includes an arrangement of switches and solenoids for controlling the raising and lowering of the flasher 70 by motor 68. Specifically, switches 428 and 430 remain in the normal upward position so long as input signal $\overline{FLMTRON}$, applied to solenoid 432, stays "high"—indicating a desire on the part of the operator to maintain the motor 68 in the "off" condition. In fact, switches 428 and 430, when in the upward position, create a short circuit across the power input terminals of motor 68.

However, in response to an operator command for turn-on of the motor 68, $\overline{FLMTRON}$ goes "low," resulting in actuation of switches 428 and 430 to the downward position, thus establishing a power input path to terminals A, B and C of motor 68. Then, motor 68 is caused to raise or lower the flasher 70 in accordance with the position of switch 432—the upward position causing the application of a positive voltage to terminal A of motor 68, thus lowering flasher 70, and the lowermost position of switch 432 resulting in the application of a positive voltage to terminal B of motor 68, causing raising of the flasher 70. More specifically, input $\overline{FLSHDWN}$ remains in the "high" state so long as raising of the flasher 70 is desired, and switch 434 accordingly remains in the lowermost position. Conversely, when $\overline{FLSHDWN}$ goes "low," solenoid 436 actuates switch 434 to the uppermost position, and lowering of the flasher 70 by the motor 68 is effected (provided, of course, that relay 432 is also actuated).

Relay panel 20 of FIG. 8 receives input signals $-CGMTR$ and $+CGMTR$ from control panel 54 (FIG. 2), and supplies same to motor 74' for the purpose of controlling the speed of rotation of the stripe cage 76 by motor 74'.

Relay panel 20 also receives inputs $-SHUT$ and $+SHUT$ from control panel 54, and provides same to shutter 66 (FIG. 2) for the purpose of opening and closing the shutter 66 in response thereto. Furthermore, relay panel 20 provides D.C. power to the mirrors 14, and as well provides output signals XDRIVE and YDRIVE (received from logic section 62 via control panel 54) to the mirrors 14 for the purpose of driving the mirrors in the X and Y directions, respectively. Relay panel 20 also receives, from mirrors 14, the X and Y position signals XBACK and YBACK which are provided to logic section 62 (via control panel 54) for the purpose of developing the POSX and POSY status inputs to processor 34 via interface 30.

The control panel 54 of FIG. 2 will now be described in more detail with reference to FIGS. 9A through 9E.

The control panel 54 (FIG. 2) basically serves two purposes. First, it is used as a junction box to distribute power throughout the system, and to act as a common distribution point for most of the control and status signals passing through the CEOG system. Secondly, it serves the usual function of a control panel—visibly, allowing the operator to interact with the system by means of switches and display indicators. In the preferred embodiment, the former function—that of a junction box—is served by having one cable from each functional unit (for example, as seen in FIG. 2) to the control panel, as opposed to having a plurality of cables passing throughout the system between the various functional units.

Figure 9A:
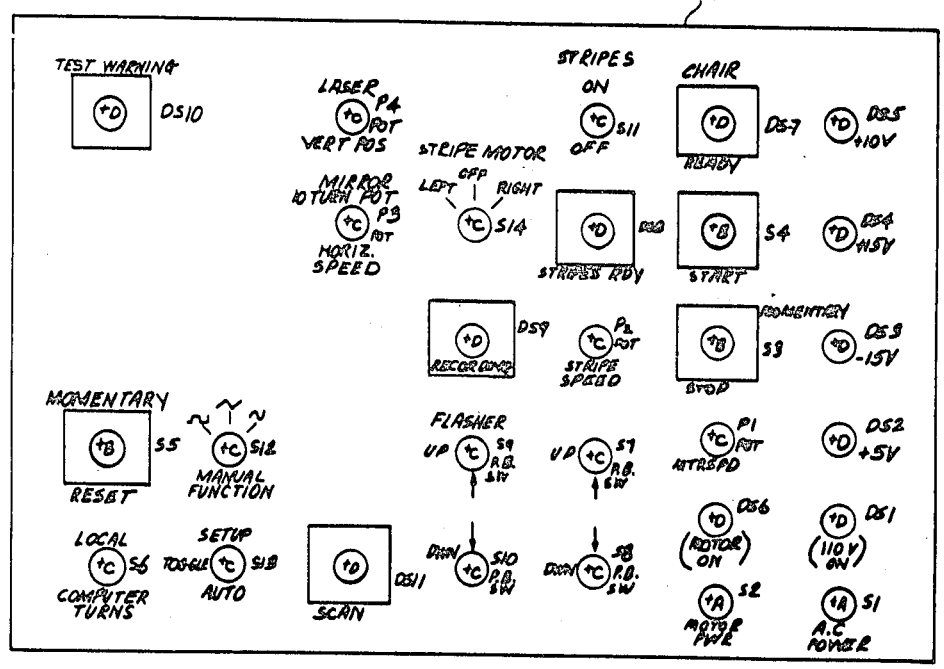
FIG. 9A is a diagrammatic representation of the operator control section 450 of the control panel 54 of the CEOG system of FIG. 2.

FIG. 9A is a diagrammatic representation of the operator control section of the control panel 54 of the CEOG system.

In general, the operator control section 450 of control panel 54 comprises a plurality of display indicators (DS), switches (S), and adjustment knobs connected to potentiometers (P). Moreover, the various display indicators, switches and adjustment knobs can be divided into various categories relating to power, chair control, stripe cage operations, flasher operations, and light source (laser) and mirror operations.

Operator control section 450 includes an A.C. power switch $S_1$, by means of which the system is turned on and A.C. power is supplied thereto. Application of A.C. power is indicated by display indicator DS1. As indicated previously, with respect to FIG. 2, application of A.C. power to the CEOG system, and specifically to power supply 60 thereof, results in generation of various D.C. supply voltages. Returning to FIG. 9A, operator control section 450 includes various display indicators DS2, DS3, DS4 and DS5, indicating availability of the various D.C. power supply voltages—+5 v., −15 v., +15 v., and +12 v., respectively.

Operator control section 450 also includes a switch $S_2$ for turning on the motor 50 (FIG. 2) for the purpose of powering the chair 8. Display indicator DS6 indicates when the motor 50 is turned on. Moreover, a desired speed of the motor 50, and thus a desired speed of revolution of the chair 8, is selected by the operator by means of adjustment knob $P_1$ which is connected to a potentiometer (not shown) for generating the signal MTRSPD applied to the motor controller 52 (FIG. 2), and specifically to the linear servo controller 320 thereof (FIG. 7A).

Operator control section 450 of FIG. 9A also includes switches $S_3$ and $S_4$ for causing momentary stopping and starting, respectively, of the chair 8 (FIG. 2), and a display indicator DS7 indicating when a "CHAIR READY" condition exists.

In addition, operator control section 450 includes a reset switch $S_5$, which is preferably a momentary switch comprising a manual reset button which is utilized for a multitude of purposes, visibly: (1) to cause the rotatable chair 8 (FIG. 2) to be rotated to its normal (reset) position; and (2) to clear a number of computer bits such as SCAN (referring to mirror scanning) and RECORDING ON DISK (to be discussed below).

Operator control section 450 also includes switches $S_7$ and $S_8$ for raising and lowering, respectively, the stripe cage 76 (FIG. 2). Preferably, switches $S_7$ and $S_8$ are one-shot push-button switches for raising and lowering, respectively, the stripe cage 76 in response to a single push of the respective buttons $S_7$ and $S_8$.

Moreover, operator control section 450 includes an adjustment knob $P_2$ connected to a potentiometer (not shown)—preferably, a 10-turn potentiometer—for adjusting the speed of rotation of the stripe cage 76 (FIG. 2).

Operator control section 450 also includes an on-off switch $S_{11}$ for activating-deactivating a linear light bulb 400 (FIG. 8) inside the stripe cage 76 (FIG. 2). Also provided is a three-position switch $S_{14}$ having positions "left" and "right" for designating respective leftward and rightward directions of rotation of the stripe cage 76, and an "off" position for turning off the rotatable stripe cage 76.

Operator control section 450 also includes display indicator DS8 for indicating the "stripes ready" condition, display indicator DS9 (RECORDING ON DISK) which is an indicator that flashes when the computer is transferring data to the disk (so that the system operator will not inadvertently fill the disk to full capacity) and push-button switches $S_9$ and $S_{10}$ for raising and lowering, respectively, the flasher 70 (FIG. 2).

Moreover, operator control section 450 includes adjustment knobs $P_3$ and $P_4$ for controlling the horizontal speed and vertical position, respectively, of the light generated by the light source (laser) 12 (FIG. 12). Specifically, adjustment knob $P_3$ is connected to a potentiometer (not shown)—preferably, a 10-turn potentiometer—for controlling the horizontal speed of the light spot seen by the subject 2 (FIG. 2), such light spot being controlled as a result of movement of the mirrors 14 reflecting the light from the laser 12, such movement of the mirrors 14 being in turn controlled by the potentiometer (not shown) as set by the operator via adjustment of knob $P_3$ Vertical position of the light spot seen by the subject 2 is controlled by adjustment of the laser 12 via the potentiometer (not shown) as set by the adjustment knob $P_4$ Operator control section 450 also, preferably, includes a manual function switch $S_{12}$, by means of which the position of the light spot generated by the laser 12 and mirrors 14 (FIG. 2) can be controlled in accordance with various functions—for example, an alternating square wave function, alternating ramp function, and alternating sine wave function.

Operator control section 450 includes a toggle switch $S_{13}$ for operator selection of the "set-up" or "automatic" modes of operation of the light source 12 and mirrors 14 (FIG. 2). That is to say, designation of the "set-up" mode of operation causes the subject 2 to be subjected to light source stimuli in accordance with a pattern selected by the physician administering the test by means of a previously explained control contained in the operator control section 450. Conversely, designation of the "automatic" mode of operation causes the subject 2 to be subjected to light stimuli as controlled by the computer (processor) 34 of the CEOG system.

Operator control section 450 includes a test warning indicator DS10, which is actuated when testing of or adjustment to the system is being performed (such as manual running of the chair 8 (FIG. 2) by means of a manual switch located in one of the portions L3' (FIG. 10G) of logic section 62 (FIG. 2)). As will be seen below, another "test warning" condition consists of the release of the electromagnetic brake on the chair 8 (FIG. 2) so that the chair 8 can be turned manually away from its normal (reset) position.

Operator control section 450 also includes a display indicator DS11 for indicating the "scan" mode of operation of the CEOG system, and a switch $S_6$ for designating that the number of turns through which the chair 8 (FIG. 2) is to be rotated is as indicated (automatically) by the computer processor 34 of the CEOG system.

FIGS. 9B through 9E are detailed schematic diagrams of the control panel 54 of the CEOG system.

Figure 9B:
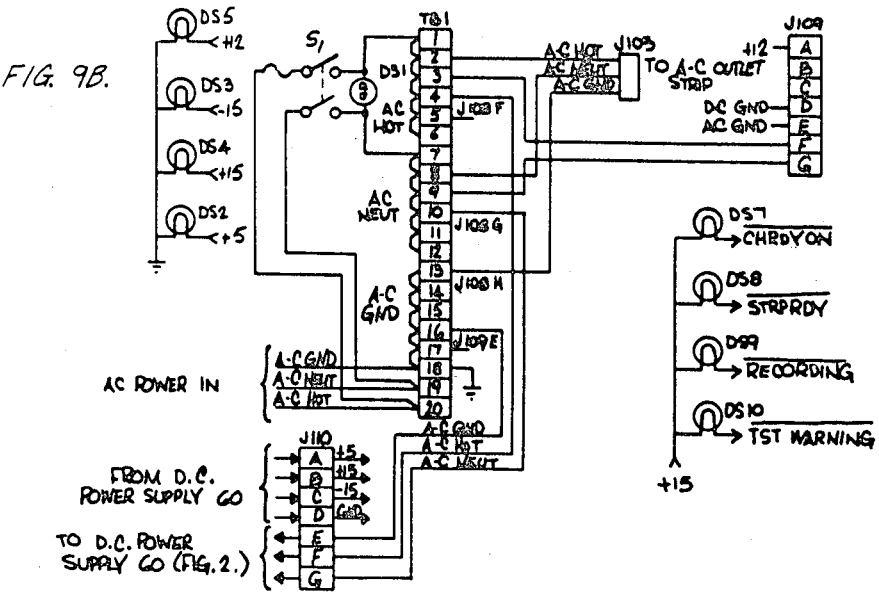

More specifically, FIG. 9B is a detailed schematic diagram relating to the power distribution functions performed by the control panel 54 of FIG. 2, as well as relating to the on-off A.C. power switch ($S_1$) and various display indicators (DS1, DS2, etc.) appearing in the operator control section 450 of the control panel 54. As seen in FIG. 9B, actuation of the switch $S_1$ causes A.C. power in to be distributed—via terminal board TB1—to various parts of the CEOG system via connector terminals J103, J110 (terminals E, F, and G thereof), etc. As previously mentioned, power supply 60 (FIG. 2), in response to actuation of A.C. power in the system, generates D.C. supply voltages (for example, +5 v., +12 v., ±15 v., etc.), as needed.

Further referring to FIG. 9B, the condition "A.C. power on" is indicated by display indicator DS1. Similarly, generation of the D.C. supply voltages mentioned above is indicated by respective display indicators DS2 through DS5.

Finally, certain of the modes of operation or conditions of the CEOG system are indicated by display indicators DS7 through DS10. Specifically, in accordance with the arrangement shown in FIG. 9B, occurrence of a "chair ready" condition causes one terminal of display indicator DS7 to go "low" (as indicated by $\overline{\text{CHAIRREAD}}$), and this grounding of one side of display indicator DS7 causes application of a +15 volt D.C. voltage to display indicator DS7, resulting in visual display of the "chair ready" condition. In a similar manner, display indicators DS8 through DS10 indicate the "stripes ready," "recording," and "test warning" conditions or modes of operation, respectively.

Referring to FIG. 9C, circuit 456 receives an input MTRSPD1, provided (as will be seen below) by logic portion L3 (FIG. 10F), which converts the digital signals RUNFWD, RUNBKD and RUNSLOW to analog signals. Circuit 456 (FIG. 9C)—by means of a voltage divider comprising resistor 458 and the resistance of potentiometer 460 (which is set by adjustment knob $P_1$ (FIG. 9A))—produces output MTRSPD which, as previously mentioned, is an analog signal provided to motor controller 52—specifically, linear servo controller 320 thereof—for the purpose of controlling the speed of rotation of the chair 8 (FIG. 2) to a desired speed in accordance with the operator setting of potentiometer 460 (FIG. 9C).

Circuit 462 shows switch $S_2$, by means of which the motor power supply for operation of the chair 8 (FIG. 2) is turned on. Display indicator DS6 indicates "motor power on" when the chair motor is powered on, and output signals MTPWR and MTRSWON (to be discussed below) are produced in the process.

Circuit 464 in FIG. 9C includes switch $S_3$ which is a momentary switch which, upon actuation, is momentarily moved from an "up" position to a "down" position, thus transferring a ground condition from terminals STOPSW to terminals $\overline{\text{STOPSW}}$. As will be seen below (with reference to portion L2' of FIG. 10D), terminals STOPSW and $\overline{\text{STOPSW}}$ are used to set and reset, respectively, a no-bounce switch 750.

Circuit 466 includes switch $S_4$ which operates in the same manner as switch $S_3$ to selectively produce ground conditions at terminals STRSW and $\overline{\text{STRSW}}$. Moreover, in a similar manner, circuit 468 selectively produces ground conditions at RSTSW and $\overline{\text{RSTSW}}$.

Circuit 470 includes switch $S_6$ (a toggle switch) which, in its upward or closed position, designates local control of the number of turns or revolutions which the chair 8 (FIG. 2) is to take before being stopped. The number of turns or revolutions is locally designated by the operator utilizing a decoded thumb-wheel switch $S_{21}$-$S_{24}$ located in logic portion L1' of FIG. 10B (to be discussed below). When not in the upward or closed position, switch $S_6$ turns control of the number of revolutions of the chair 8 (FIG. 2) over to the computer for automatic control thereof.

Circuit 472 includes potentiometer 474 associated with adjustment knob $P_2$ (FIG. 9A), by means of which stripe speed is designated as a result of voltage division of a +15 volt input between resistor 476 and potentiometer 474, providing an analog output STRIPESPD designating the speed of revolution of the stripe cage 76 (FIG. 2).

Circuits 478 and 480 includes switches $S_7$ and $S_8$, respectively, which, in response to actuation thereof, generate outputs $\overline{UPCGSW}$ and $\overline{DWNCGSW}$, respectively, designating upward and downward movement, respectively, of the cage 76 (FIG. 2).

Circuit 482 includes switch $S_{13}$ which, in its upward position, provides output $\overline{SETUP}$ calling for the mirrors 14 (FIG. 2) to move in accordance with the setting of manual function switch $S_{12}$ (in operator control section 450 of FIG. 9A). Switch $S_{13}$—in its lower position—turns control of the mirrors 14 over to the computer processor 34 (FIG. 2) for automatic control thereof.

Circuit 484 includes display indicator DS11 which is actuated by a +15 volt input in response to terminal $\overline{SCNLIT}$ going "low." Terminal $\overline{SCNLIT}$ goes "low" as a result of logic operations performed in portion L9 (FIG. 10L), as will be described in more detail below, when: (1) the setup switch S13 is "on," (2) the computer is scanning in the X direction, and (3) the computer is canning in the Y direction.

Circuits 486 and 488 include switches $S_9$ and $S_{10}$, respectively, which operate in the same manner as previously described with respect to circuits 464 and 466. The output conditions at terminal UPFLSW, DWNFLSW, etc. in circuits 486 and 488 are utilized to set/reset no-bounce switches contained in portion L4' (FIG. 10I).

Circuit 490 includes switch $S_{11}$ which, in response to actuation thereof, issues output signal STRPWS indicating "turn on" of the light 400 (FIG. 8) in stripe cage 86 (FIG. 2).

Circuit 492 includes switch $S_{12}$ by means of which three scanning functions for scanning of the light source 12 (FIG. 2)—under control of the mirrors 14—may be chosen. Specifically, output signals $\overline{SQUAR}$, $\overline{TRNGL}$, and $\overline{SINE}$ are provided in correspondence to desired scanning in accordance with square wave, triangular (or ramp function) and sine wave functions, respectively.

Circuit 494 includes potentiometer 496 corresponding to adjustment knob $P_3$ (FIG. 9A), by means of which horizontal speed of the mirrors 14 (FIG. 2) can be chosen. Circuit 494 produces output signal OSREF, which designates the desired horizontal scanning speed of the mirrors 14 relative to lowermost and uppermost reference speeds determined by the voltage dividing resistors 498 and 500, respectively.

Circuit 502 discloses potentiometer 504 corresponding to adjustment knob $P_4$ (FIG. 9A), by means of which vertical positioning of the beam from light source 12 is adjusted. As a result of such adjustment, circuit 502 performs voltage division by means of potentiometer 504 so as to provide output signal VERTPOS indicating the desired vertical positioning of the beam from light source 12. It is to be noted that, as will be seen below in connection with the discussion of portion L10 (FIG. 10M), potentiometer 504 acts in parallel with the MOVY input from the computer, and with any other signals which are summed in a summing amplifier of portion L10, to develop the output YDRIVE, by means of which the desired vertical positioning of the beam from light source 12 is achieved.

Turning to FIG. 9D, circuit 506 discloses switch $S_{14}$ (FIG. 9A), by means of which leftward or rightward movement, or stopping, of the stripe cage 76 (FIG. 2) is achieved. Leftward movement of the stripe cage 76 corresponds to output −CGMTR, while rightward movement of the stripe cage 76 corresponds to output +CGMTR—these two output signals being provided to relay panel 20 (FIG. 8), and thence to motor 74' so as to achieve leftward or rightward movement, respectively, of the stripe cage 76 (FIG. 2) under the control of the motor 74'.

As can be seen from circuit 506 of FIG. 9D, switch $S_{14}$ has an "off" position whereby neither leftward nor rightward movement of the stripe cage 76 is designated. Moreover, as seen in FIG. 9D, circuit 506 further comprises a switch $S_{14}'$ which is gang-connected to switch $S_{14}$, and which generates outputs $\overline{LFTSW}$ and $\overline{RHTSW}$ in response to actuation of switch $S_{14}$ to the "left" and "right" position, respectively. The outputs $\overline{LFTSW}$ and $\overline{RHTSW}$ are provided as status signals to logic section 62 (FIG. 2).

Referring to FIG. 9E, further circuits 530 through 533 are shown, which circuits are utilized for converting various control signals to driver signals. Specifically, circuit 530 converts signals TWLON (Test Warning Light On) and CHRDYON (Chair Ready On) to signals which can light display indicators DS10 and DS7, respectively (FIG. 9A). Circuit 531 supplies a regulated +12.3 volts, called +RELAY, which signal—as will be recalled with respect to FIG. 8—is provided to relay panel 20 for the purpose of powering certain previously described solenoid/relay switch combinations.

Circuit 532 converts input signals RELBRK (Release Brake), LITEON (Light On), FLMTRON (Flasher Motor On), FLSHDWN (Flasher Down), TRMTRON (Stripe Cage Motor On), and TRMTRDN (Stripe Cage Down) to their corresponding driver signals.

Finally, circuit 533 converts input signal STRIPESPD—from the "center wiper" of the potentiometer 474 (FIG. 9C) associated with adjustment knob $P_2$ (FIG. 9A)—to output signals +CGMTR and −CGMTR provided to relay panel 20 (FIG. 8), and thence to motor 74' for the purpose of turning the stripe cage 76 (FIG. 2) at a given speed. The latter is accomplished by circuit 533 under the influence of further input TRNCG (Turn Cage) provided (via resistor 536) to the base of transistor 535, the latter pulling −CGMTR to ground so as to turn on the stripe cage motor 74' (FIG. 8).

At this juncture, a short description of operator usage of operator control section 450 (FIG. 9A), with reference to the various other FIGS. 9B through 9E, is appropriate. Specifically, a short description of the usage of operator control section 450 will be given for both the EOG and VER tests.

In order to conduct EOG and VER tests, the operator can take the following actions:

(1) He will power-up the CEOG system by actuating switch $S_1$ on operator control section 450 (FIG. 9A), thus distributing A.C. power and various D.C. supply voltages to various parts of the CEOG system, as previously described with reference to FIG. 9B.

(2) The operator will then actuate switch $S_{13}$ (FIG. 9A), causing generation of signal $\overline{SETUP}$ by circuit 482 (FIG. 9C). At this juncture, shutter 66 (FIG. 2) will be opened, and it will be possible to submit the patient 2 to light stimulation as generated by light source (lasar) 12 in conjunction with mirrors 14. In the "set-up" mode of operation, mirrors 14 will scan the X direction in accordance with the particular manual function previously designated by the operator utilizing switch $S_{12}$ in operator control section 450 (FIG. 9A—see also circuit 492 of FIG. 9C). Moreover, the Y position of the mirror will be determined by a combination of the setting of adjustment knob $P_4$ (and potentiometer circuit 502) and a MOVY command from computer processor 34 (FIG. 2), as will be discussed in more detail below. The scanning speed of mirrors 14 (FIG. 2) will be determined by the setting of adjustment knob $P_3$ (in conjunction with potentiometer circuit 494), and will preferably yield a scanning cycle time of from 0.8 seconds to 10 seconds duration. During the "scanning" mode of operation, this mode of operation will be indicated on display indicator DS11 (see circuit 484 of FIG. 9C).

(3) As previously mentioned, switch $S_{13}$ is a toggle switch, such that subsequent toggling of switch $S_{13}$ will result in "automatic" mode of scanning. As a result of entering this mode of operation, scanning will be performed under computer control. Moreover, the computer processor 34 can be programmed to completely and exclusively control the scanning pattern, speed, etc. to which the subject 2 is subjected. In the alternative, the computer can be programmed so that scanning can be controlled as to the scanning pattern in accordance with whichever scanning function is manually selected at switch $S_{12}$, and can also be controlled so as to cause the horizontal speed of scanning to be in accordance with whatever horizontal speed is set manually at adjustment knob $P_3$ of operator control section 450. As a further alternative, the computer processor 34 can be programmed to cause vertical scanning to be conducted in accordance with whatever speed is set on adjustment knob $P_3$ (even though adjustment knob $P_3$ is normally utilized to merely designate horizontal speed of scanning).

(4) The operator can reset the system by actuating switch $S_5$ which, with reference to FIG. 9C, will cause generation of signal RSTSW which, as will be seen below, will be received and processed in logic section 62 (FIG. 2).

The CEOG system can be utilized to conduct further EOG tests—for example, a test can be performed utilizing operator control section 450 to control rotatable chair 3 (FIG. 1), as follows:

(1) The system is powered on by actuating switch $S_1$ (as discussed above with respect to the EOG test).

(2) The chair motor is activated by actuating switch $S_2$ (such being indicated by display indicator DS6). As previously discussed, this results in generation of signal MTRPWR by circuit 462 (FIG. 9C).

(3) The operator resets the system by actuation of switch $S_5$, which—via circuit 468 of FIG. 9C—results in generation of RSTSW which is provided to logic section 62 (FIG. 2). At this juncture, the chair will seek its normal (reset) position, ready for rotation, and the "chair ready" condition is indicated by display indicator DS7.

(4) The operator can now enter data relating to, for example, the number of turns to be performed by the chair, utilizing terminal 44 (FIG. 2)—this will be explained in more detail below.

(5) By pushing switch $S_4$, the operator can now cause the chair to rotate through the designated number of turns.

(6) By pushing $S_3$, the operator can stop the chair prior to the predesignated number of turns, at which time a blinking CHAIR READY light will be seen at display indicator DS7.

(7) The operator can now restart chair rotation by actuating switch $S_4$, and the predesignated number of turns will be completed. At the completion of the predesignated number of turns, the chair will automatically stop, and a blinking CHAIR READY indicator will be seen at display indicator DS7.

(8) The CEOG system can be programmed (as will be seen subsequently) to continue rotation, but this time in the counter-clockwise direction (presuming that the previous direction of rotation was clockwise), in response to further actuation of switch $S_4$.

(9) During the operation, as previously described, the operator can either press a computer console button calling for a hard-copy printout of the test results, or can type a predesignated character (such as the character "R") on the console of the computer so as to record the test results on a more permanent storage (such as disk 42 (FIG. 2)).

(10) As will be seen in more detail below, the system can operate in an "automatic reset" mode of operation, by which reverse chair rotation will take place in a "slow mode" of operation, and the CEOG system will seek a "limit switch" setting—corresponding to a normal (reset) position—at which time chair rotation will be stopped. This will be explained in more detail below.

(11) Finally, as will also be seen below, switch $S_6$ gives the operator the alternatives of "local" control or "computer" control of the number of turns through which the chair 8 (FIG. 2) is to pass prior to being automatically stopped. As will be recalled from previous discussion, the number of turns through which the rotating chair is to pass can be locally designated by actuation of a decoded thumbwheel switch $S_{21}$-$S_{24}$ in portion L1' (FIG. 10B) of logic section 62 (FIG. 2).

In administering tests to the subject 2, operator console section 450 (FIG. 9A) can be utilized to control the stripe cage 76 (FIG. 2). Thus, by means of one-shot actuation of push-button switch $S_8$, the stripe cage 76 will be lowered into position. At that juncture, if switch $S_{11}$ has been actuated to the "on" mode, and if switch $S_{14}$ is set to either the "left" or "right" position—that is, not to the "off" position—then the linear light bulb 400 (FIG. 8) will come on, and stripe cage 76 will begin to rotate immediately upon arriving at its lowermost position. Actuation of switch $S_7$ at any time during the test will result in automatic cessation of the rotation of stripe cage 76, as well as turn-off of light bulb 400, and the stripe cage 76 will be raised to its uppermost position. As previously discussed, control of the speed of rotation of stripe cage 76 is achieved through adjustment knob $P_2$ and the associated potentiometer 474 in circuit 472 (FIG. 9C). Display indicator DS8 indicates the "stripes ready" condition. Display indicator DS9 is a RECORDING ON DISK indicator which reminds the operator that test data from the subject 2 is being recorded on disk 42 (FIG. 2).

Figure 10B:
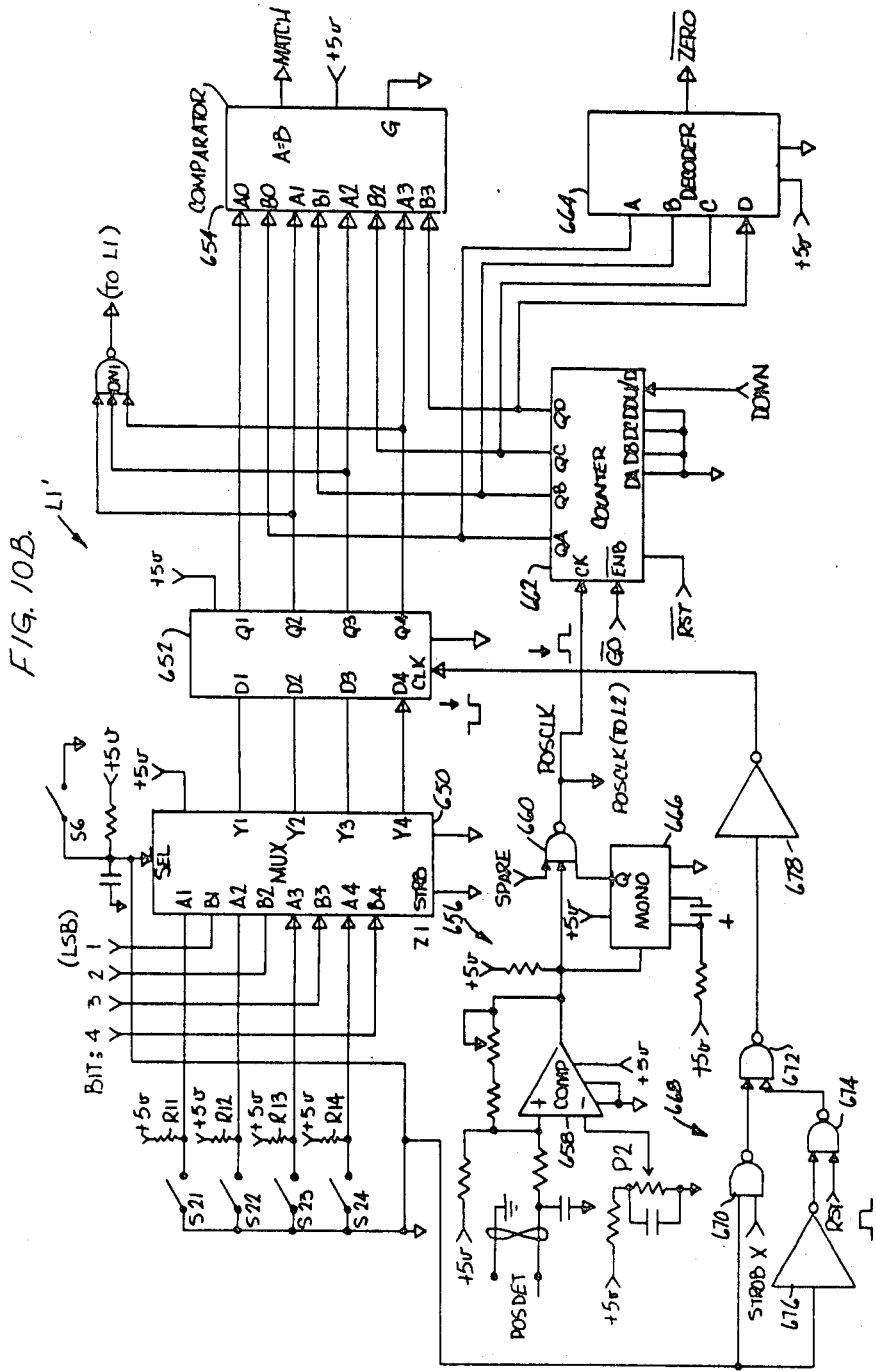
FIGS. 10A through 10O are detailed logic block diagrams and circuit schematics of the logic section 62 of the CEOG system of FIG. 2.
Figure 10O:
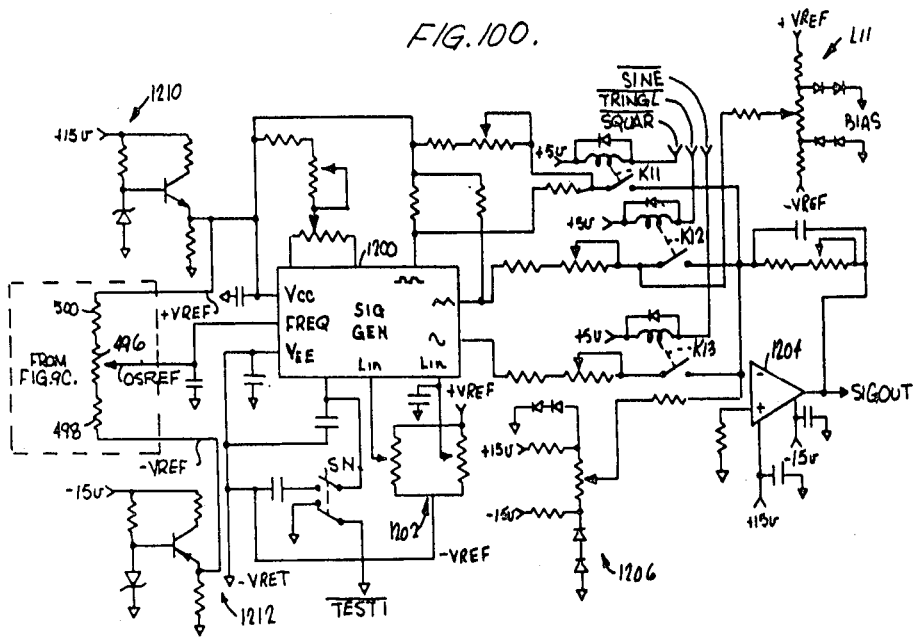
Figure 10G:
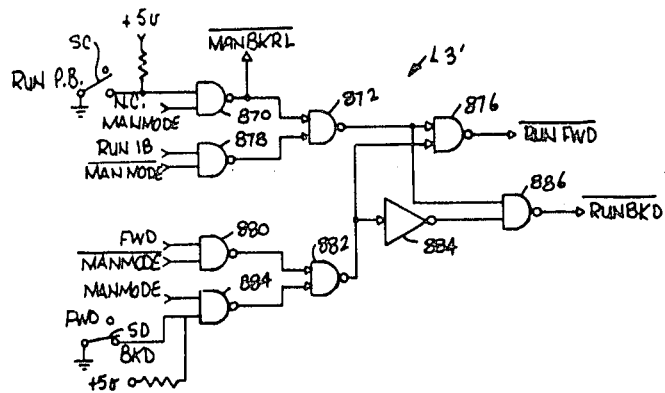
Figures 10E, 10F:
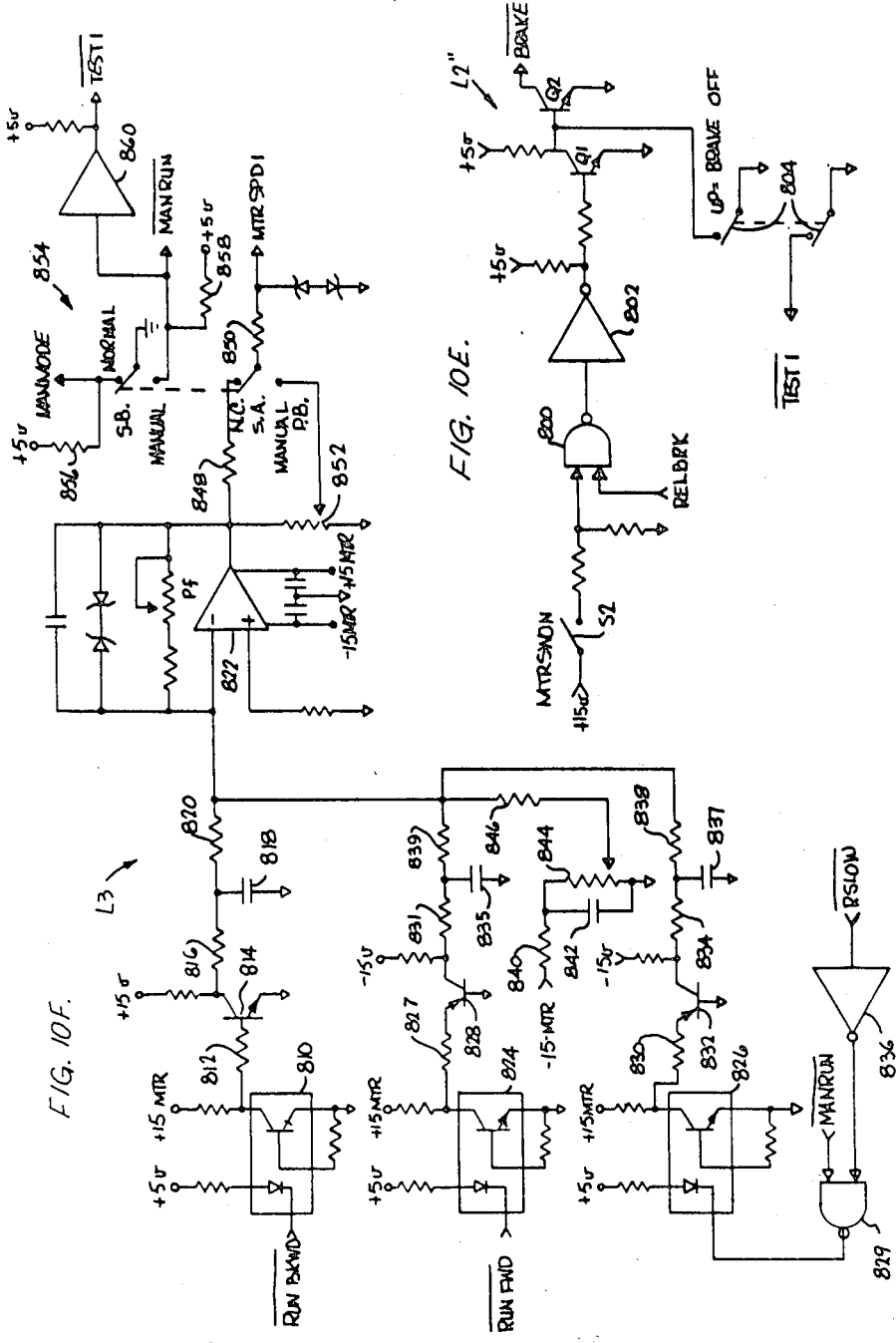
Figure 10H:
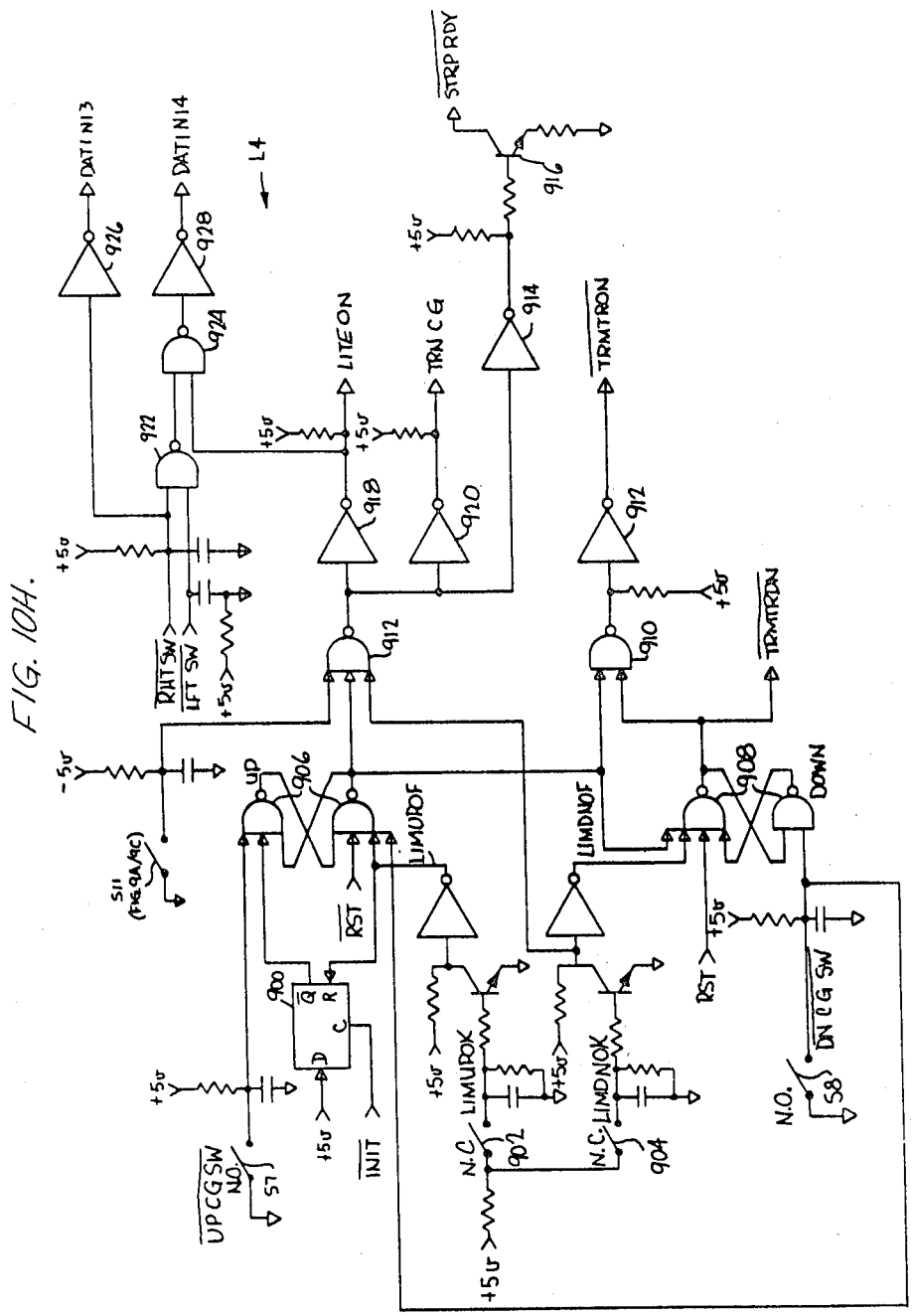
Figure 10K:
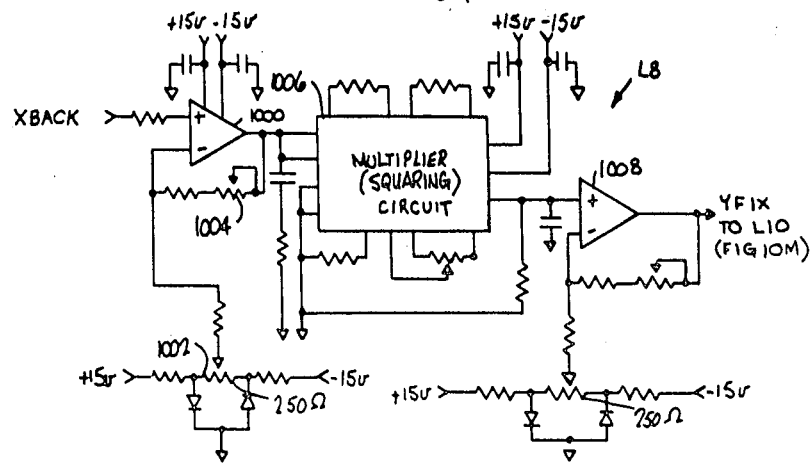
Figure 10I:
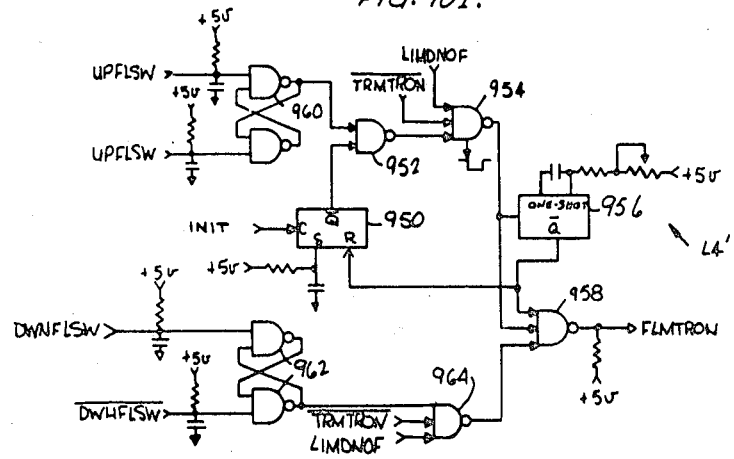
Figure 10N:
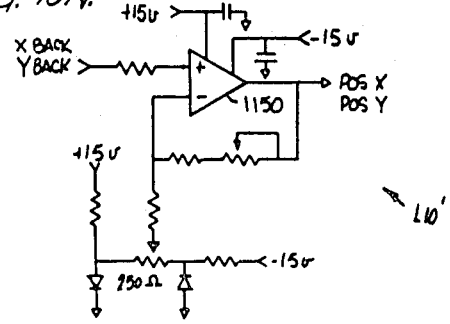

FIGS. 10A through 10N are detailed logic block diagrams and circuit schematics of the logic section 62 of the CEOG system.

Logic section 62 (FIG. 2) receives electronic signals from three sources: the computer processor 34 via EOG interface 30 (FIG. 2), the switches on the control panel (FIG. 9A) and associated circuitry (FIGS. 9B through 9E), and other units or elements of the CEOG system (as will be described below). The logic section 62 processes all of these incoming signals, and produces control and indicator signals that are distributed to the remainder of the CEOG system. Logic section 62 will, for the purpose of the discussion below, be divided into logic section portions L1 through L5 and L8 through L11, each of which will now be considered in detail.

FIGS. 10A and 10B are detailed logic diagrams/schematics of the portions L1 and L1', respectively, of logic section 62 (FIG. 2). Portions of L1 and L1' of logic section 62 basically perform the following four functions:
(1) automatic system initialization for "power-on";
(2) system reset;
(3) test-warning-light generation; and
(4) counter and comparator operations to determine how many turns the chair 8 (FIG. 2) should make.

Referring to FIGS. 9A and 10A, when the system is turned on—by actuation of switch $S_1$—various D.C. and A.C. voltages are caused to flow throughout the system. In response to reception of D.C. input, timer 628 in portion L1 (FIG. 10A) is triggered to issue output INIT. The latter is provided to NAND gate 608—which performs an OR operation—so as to issue output RST and (via inverter 612) output $\overline{RST}$. The output of NAND gate 608 is provided to a one-shot device 616 which—since its Q output is provided, as an enabling input, to NAND gate 608—insures that the RST (and $\overline{RST}$) output is a square pulse of duration no less than 0.1 seconds. In other words, one-shot device 616 protects the RST output from being immediately turned off—as, for example, by reception of a "high" signal from NAND gate 626 if NEARRST or ZERO go "low." This will be more clearly understood from the discussion below.

In addition, NAND gate 608 is caused to issue the output RST upon setting of the no-bounce switch 600 (NAND gates 602 an 604 connected as shown) upon receipt of the "high" RSTSW input, provided by operator actuation of switch $S_5$ in operator control section 450 (FIG. 9A)—see also circuit 468 (FIG. 9C).

Finally, NAND gate 608 is caused to issue the RST output as a result of inputs ZERO and NEARRST (received by NAND gate 626) both being "high" or "on." Input ZERO is an output provided by decoder 664 in portion L1' (FIG. 10B) which, as will be seen below, indicates that the chain has been rotated in the reverse direction by a rpescribed number of turns. In a related manner, input NEARRST is an output of portion L2' (FIG. 10D) which, as will be seen below, is a control signal indicating that the chair is in the "backward rotation" mode of operation. Thus, as a result of the operation of NAND gates 608 and 626 (FIG. 10A), the RST output wil be issued—indicating reset of the CEOG system—whenever the chair has been rotated in a backward direction a prescribed number of turns so that a down-count to zero has been achieved.

Further referring to FIG. 10A, circuit 632 comprises a timer 634 which provides, at its Q output, an oscillator output BLINK applied to various selected display indicators to achieve a "blinking" effect. For example, the test warning indicator DS10 (FIG. 9A) can be caused to blink by application thereto of output BLINK of circuit 632 (FIG. 10A). Furthermore, circuit 632 includes a NAND gate 638 which performs an OR-type operation with respect to inputs $\overline{TESTI}$ and $\overline{TOOHI}$, so that the output TWLON (Test Warning Light On) is issued in the presence of either input $\overline{TESTI}$ or $\overline{TOOHI}$, and input BLINK. As will be seen below, $\overline{TESTI}$ goes "high" whenever a particular test function is to be performed (for example, when the chair is to be manually controlled for rotation via actuation of switches SA and SB in portion L3 (FIG 10F). Moreover, input $\overline{TOOHI}$ is produced by portion L1' (FIG. 10B) whenever the number of turns through which the chair is to rotate, as set by the operator, exceeds an allowed value.

Referring to portion L1' of FIG. 10B, it will be recalled that the number of turns through which the chair 8 is to be rotated can be designated under computer control as entered on a computer console or terminal 44 (FIG. 2), or under local control via presetting of a thumbwheel switch consisting of switches $S_{21}$ through $S_{24}$ (FIG. 10B). Thus, multiplexer (MUX) 650 receives and multiplexes turn information either generated by the computer as bits 1–4 from the processor 34 (FIG. 2), or locally designated via switches $S_{21}$–$S_{24}$. The multiplexed output of multiplexer 650 is provided to latch circuit 652 which provides its latched output to the A0–A3 inputs of comparator cirucit 654.

Circuit 656 of portion L1' of FIG. 10B responds to an input POSDET (representing chair position information), and—via analog comparator 658 and NAND gate 660—generates output POSCLK whenever a reflective strip 350 (FIG. 7A) on the chair is detected by photodetector 354. Output POSCLK provides a clocking input at the CK terminal of counter 662 which is an up-down counter for up-counting the number of chair revolutions (for example, during clockwise rotation), and for conversely down-counting the number of chair revolutions (for example, during counter-clockwise chair rotation). The outputs $Q_A$–$Q_D$ of Counter 662 provide the B0–B3 inputs to comparator 654.

Thus, digital comparator 654 compares the desired number of chair revolutions to the actual number of chair revolutions, and when the two coincide, comparator 654 generates the output MATCH.

Counter 662 is enabled, for counting, by the logical input $\overline{GO}$ (provided by a GO flip-flop 752 in portion L2 of FIG. 10D, to be discussed below). Counter 662 is reset upon occurrence of $\overline{RST}$ (indicating system reset). Up or down counting of counter 662 is determined by the logical input DOWN (provided by up/down flip-flop 772 of portion L2 of FIG. 10D). The outputs $Q_A$–$Q_D$ of counter 662 are provided to decoder 664 which issues a ZERO output upon occurrence of a complete chair cycle (clockwise rotation followed by counter-clockwise rotation). The ZERO output has already been discussed with reference to circuit 618 (FIG. 10A).

Returning to circuit 656 (FIG. 10B), the output of comparator 658 is provided to a monostable device 666 which generates a $\overline{Q}$ output to NAND gate 660 so that output POSCLK will have a minimum time duration in response to either the output from comparator 658 and/or that from monostable device 666.

Circuit 668 of portion L1' comprises NAND gates 670, and 674, and inverters 676 and 678, which provide a clock input to latch circuit 652 under either of the following two conditions:
(1) When the number of rotations of the chair is to be locally controlled, as designated by closing of the switch $S_6$ of FIG. 10B, latching of data by latch circuit 652 is controlled by the RST (Reset) signal received at AND gate 674 (enabled by an input from the switch S$_6$ via inverter 676), and provided to the CLK input of latch 652 via OR gate 672 and inverter 678.

(2) When the number of rotations of the chair is to be computer-controlled, as indicated by opening of the switch S$_6$, latching of data by latch circuit 652 is controlled by STROBX (a computer-generated strobe signal) provided via AND gate 670 (enabled by an enabling input from switch S$_6$), OR gate 672 and inverter 678.

It will be recalled that switch S$_6$ is a toggle switch correspondingly designated in operator control section 450 (FIG. 9A). Closing of the switch results in a ground connection, resulting in a "low" input to AND gate 670 (disabling computer-controlled latching) and resulting in a "high" (inverted "low") input to enable AND gate 674 for reset-controlled latching of data. Conversely, opening of switch S$_6$ results in application of a +5 volt ("high") input to enable AND gate 670 for computer-controlled latching, and to disable AND gate 674 to preclude reset-controlled latching.

Finally, referring to circuit 656 in FIG. 10B, input POSDET as previously mentioned, is an analog signal produced when light is detected from a reflective strip 350 on chair 8 (FIG. 7A). Such light is detected by comparator 658 (FIG. 10B), the negative input of which is adjusted by level-detector potentiometer P$_2$. When light is detected, comparator 658 triggers one-shot device 666 (preferably, having a one-shot duration of 0.25 seconds) so as to maintain an output POSCLK issuing from NAND gate 660 connected to the output of comparator 658. That is to say, NAND gate 660 performs an OR operation between the outputs of comparator 658 and one-shot 666. Thus, circuit 656 insures that output POSCLK is of minimum acceptable duration, and output POSCLK is provided as a clocking input to counter 662 (for counting chair rotations), and as a further input to portion L2' (FIG. 10D), as will be discussed below.

Figure 10J:
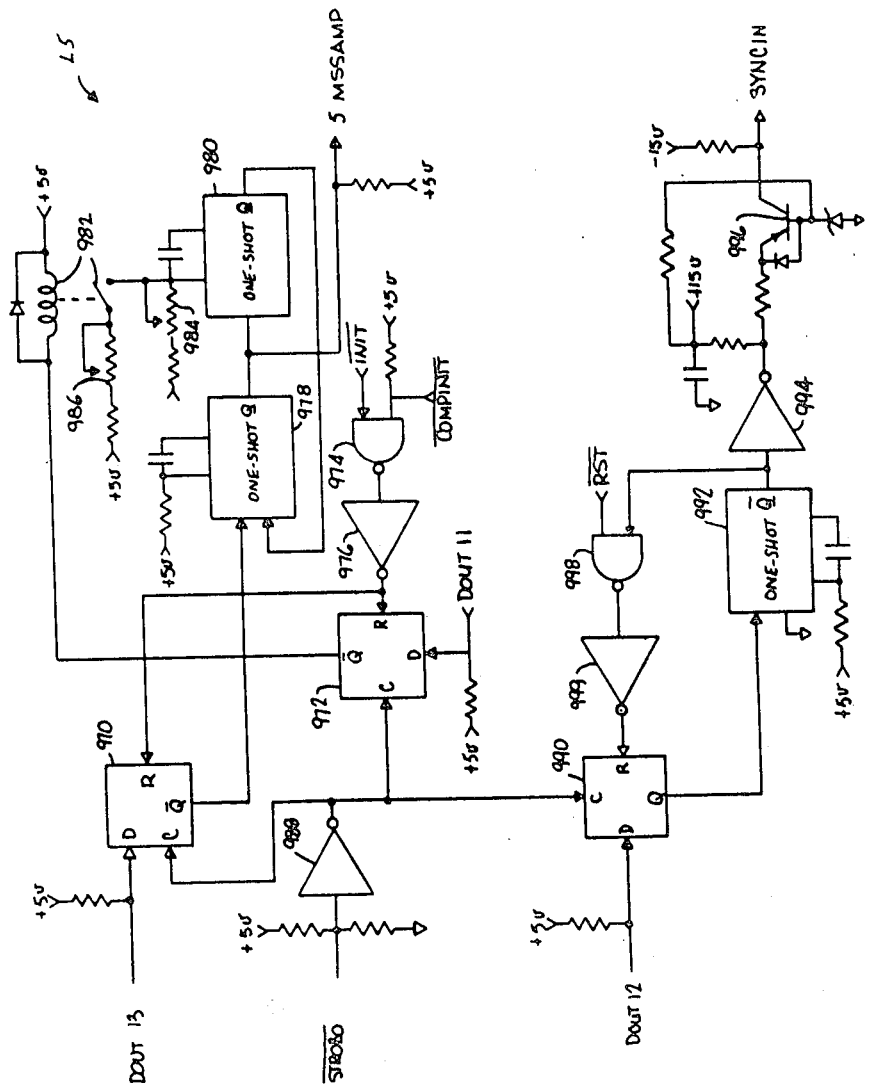
Figure 10C:
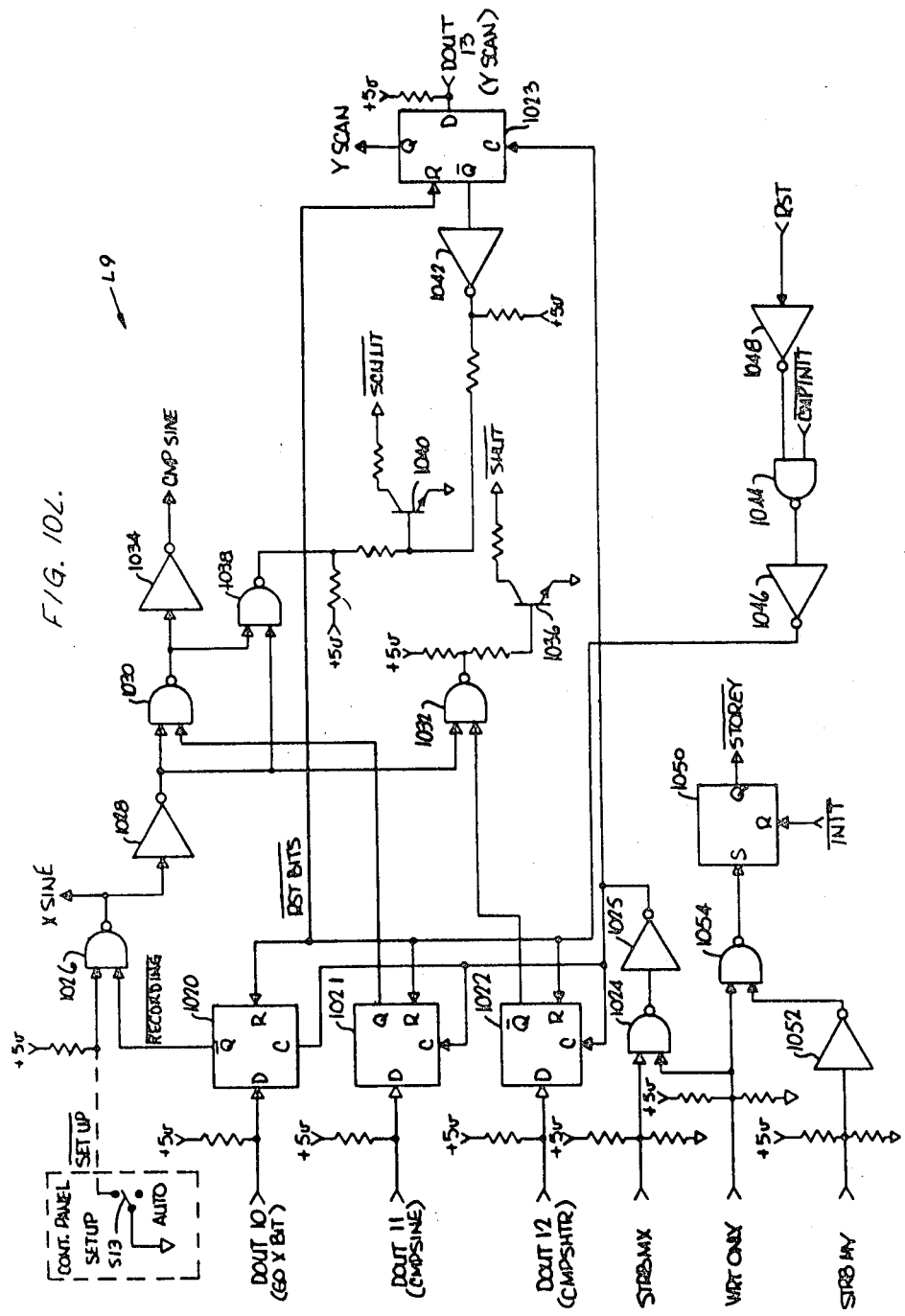

FIGS. 10C, 10D(1) and 10E are detailed schematics of further portions L2, L2' and L2", respectively, of logic section 62 of FIG. 2. FIG. 10D(2) is a timing diagram for explaining the timing of the operations of portion L2' of FIG. 10D(1). Basically, portions L2, L2' and L2" receive input signals STRSW (start switch), STOPSW (stop switch), RST (reset), $\overline{\text{STRLIM}}$ (start limit switch), and MATCH (indicating that the number of counts of chair revolutions matches the predetermined value). Portions L2, L2' and L2" provide logic circuitry for performing various logic functions so as to provide the following signals in proper sequence: CHRDYON (Chair Ready On), RUN1 B (Run Motor), $\overline{\text{RELBRK}}$ (Release Brake), FWD (Go Forward), RSLOW (Run Slowly), and DOWN (Count Down). As will be seen below, other input/output signals are received/provided as well.

Referring specifically to portion L2 of FIG. 10C, three flip-flop devices (cross-coupled NAND gates) are provided, as follows:

(1) A Run flip-flop (NAND gates 700) which provides via inverter 701 an output RUN1B when the chair motor is running, such output being provided to portion L3' (FIG. 10G). The output RUN from flip-flop 700 is OR'ed (in NAND gate 702) with input $\overline{\text{MANBKRL}}$ to provide output $\overline{\text{RELBRK}}$ (Release Brake) either when the motor is running (as indicated by RUN1B) or when manual rotation of the chair is indicated (by $\overline{\text{MANBKRL}}$ from portion L3' of FIG. 10G).

(2) A Forward/Backward flip-flop (NAND gates 704) which issues an output FWD which is "high" when the chair is being driven in the forward direction, or "low" when the chair is being driven in the backward direction.

(3) A Run Slow flip-flop (NAND gates 706) which issues an output $\overline{\text{RSLOW}}$ which is "low" when the chair is running slow. It is to be noted that the chair runs slow only in the backward direction, as dictated by the application of output FWD from NAND gate 704 via inverter 708 to device 706 (lowermost NAND gate thereof). It is to be further noted that device 706 is set by input $\overline{\text{RST}}$, such that the resetting of the system by the operator causes the chair to rotate slowly in the backward direction, this being done for the purpose of centering the chair in its normal (reset) position.

It will be recalled that resetting of the CEOG system results in generation (as previously discussed) of signal RST. Referring to FIG. 10C, input RST is provided via inverter 710 to flip-flop 712, causing resetting of flip-flop 712. As a result, the output $\overline{\text{MECRDY}}$ (to NAND gate 714) is "high." $\overline{\text{MECRDY}}$ goes "low" when the chair 8 finds the start limit switch 356, and NAND gate 714 provides the output CHRDYON. It will be noted that CHRDYON is also produced when signal $\overline{\text{HLDBLNK}}$—a signal produced by a Hold flip-flop to be discussed in connection with FIG. 10D(1) below—goes "low." Moreover, it will be recalled that the signal CHRDYON (Chair Ready On) is provided to a circuit 530 (FIG. 9E), wherein it is converted to an output $\overline{\text{CHRDYON}}$, which in turn is responsible for activation of display indicator DS7 (FIG. 9B), which indicates the "chair ready" condition.

Further referring to FIG. 10C, resetting of the system results in application of signal RST via inverter 710 as a clock input to Check Mechanical Ready flip-flop 716, causing a Q output therefrom to NAND gate 718. When the start limit switch 356 at the chair 8 (FIG. 7A) is open—indicating that the chair is not at its normal (reset) position—signal $\overline{\text{STRLIM}}$ is high (+5 volts), and the output STRLIM of inverter 720 is "low", with the result that the output of NAND gate 722 (which performs an AND operation between STRLIM and the Q output of flip-flop 716) is "high." At the same time, the output of NAND gate 718—as a result of application of "high" inputs ($\overline{\text{STRLIM}}$ and Q of flip-flop 716) thereto—maintains a "low" output $\overline{\text{STARTLOOK}}$ applied to the "set" terminal of Run flip-flop 700. This indicates that the chair 8 (FIG. 7A) is looking for its normal (reset) position. In fact, the $\overline{\text{RST}}$ is applied, as a "set" input, to Forward/Backward flip-flop 704 so that the output thereof FWD is "low," indicating the "backward" mode of rotation. At the same time, the signal $\overline{\text{RST}}$ is applied to the "set" input of Run Slow flip-flop 706, causing output $\overline{\text{RSLOW}}$ to go "low," indicating slow rotation of the chair.

Thus, to summarize, the "reset" mode of operation results in the chair 8 (FIG. 7A) being rotated slowly in the backward direction, in search of its normal (reset) position. When the normal (reset) position is reached, the start limit switch 356 is hit, causing $\overline{\text{STRLIM}}$ to go "low" and STRLIM to go "high." As a result, NAND gate 718 turns "off," and NAND gate 722 goes "low," thus resetting Run flip-flop 700. Accordingly, output RUN of flip-flop 700 goes "high," and output RUN1B goes "low" (causing turn-off of the motor 8 (FIG. 7B)), while output $\overline{\text{RELBRK}}$ goes "low," causing activation of fail-safe circuit 326 (FIGS. 7A and 7D), linear servo controller 320 and dynamic braking relay 322, so as to apply braking action to the motor 50, thus stopping rotation of the chair 8.

Furthermore, when STRLIM (from inverter 720) and the Q output of flip-flop 716 go "low," the resulting "high" output of NAND gate 722 sets flip-flop 712, and MECRDY goes "on." Later, when it is necessary to reset the flip-flop 712, this is done with signal GOB (from FIG. 10D)—which starts the chair 8 (FIG. 1) turning—signal GOB being AND'ed with RUN (from the lower NAND gate in flip-flop 700) so as to insure that the Run flip-flop 700 has been turned on before the Mechanical Ready flip-flop 712 is turned off, this being necessary because MECRDY assists in the generation of signal GOB through NAND gate 752 (see FIG. 10D(1)).

It is to be noted further that the reset (R) input of Check Mechanical Ready flip-flop 716 is connected to NAND gate 728 via resistor 730 (the latter being grounded by grounding capacitor 732). Thus, NAND gate 728 performs an AND operation with respect to the inputs thereto. Specifically, when $\overline{RUN}$ goes "high," and when the output of inverter 732 goes "high" as a result of NAND gate 722 issuing a "low" output, and further when the Q output (MECRDY) of flip-flop 712 goes "high," the Check Mechanical Ready flip-flop 716 is reset, resulting in removal of the Q input from NAND gates 718 and 722, respectively.

Thus, as explained above, resetting of the system results—as previously described—in slow, backward rotation of the chair until a normal (reset) position is arrived at, detected by actuation of the start limit switch 56 at the chair 8 (FIG. 7A).

Referring now to FIG. 10D(1), the operation of starting rotation of the chair will be explained. Actuation of start switch S$_4$ (FIGS. 9A and 9C) results in generation of signal STRSW (as previously discussed), and this signal—as received by portion L2' of FIG. 10D(1)—sets the no-bounce switch (flip-flop device) 750, NAND gate 752—which performs an AND operation with respect to the input MECRDY (Mechanical Chair Ready) from flip-flop 712 (FIG. 10C—generates output XYZ (provided as a "reset" input to Forward/Backward flip-flop 704 (FIG. 10C)). This insures that the flip-flop 704 produces output FWD, corresponding to forward operation of the chair.

Additionally, NAND gate 754 performs an OR operation between XYZ and the further input (STRSW. HOLD)—provided by NAND gate 756—to produce output GOB, the latter being provided as a clock input to "turn on" Go flip-flop 758. Generation of output GOB also turns on the Run flip-flop 700 (FIG. 10C).

As the chair 8 (FIG. 2) begins to rotate, the number of rotations are counted by the arrangement of FIG. 10B, and—when a prescribed number of rotations is counted—the output MATCH is issued by comparator 654 (FIG. 10B), as previously described. At that juncture, NAND gate 762—which performs an AND operation—detects the presence of inputs FWD, GO and MATCH, and flip-flop 764 is set. Accordingly, flip-flop device 766 is set by device 764 upon the occasion of the next POSCLK pulse.

More specifically, referring to FIG. 10D(2)—which is a timing diagram—pulse POSCLK is the primary clock pulse, based on which the number of rotations of the chair is counted. It is to be noted that, in the preferred embodiment, the chair rotates through a one-quarter turn before reception of the first POSCLK pulse. In FIG. 10D(2), it is presumed that the number of rotations is preset for three. Upon the completion of two and one-quarter turns—that is, the beginning of the third full turn—the comparator output MATCH occurs, and flip-flop 766 is set with the reception of the next POSCLK pulse.

Referring to both FIGS. 10D(1) and 10D(2), the Q output of flip-flop 766 enables one-shot device 768 so as to produce a Q output on the trailing edge of POSCLK for a prescribed period of time (preferably, 0.1 seconds), this output being defined as signal $\overline{REVRS}$. The latter is a negative pulse applied to Forward/Backward flip-flop 704 (FIG. 10C) to reset the flip-flop 704, resulting in FWD going "low," further resulting in rotation in the backward direction of the chair 8 (FIG. 2).

As best seen in the timing diagram of FIG. 10D(2), the positive going edge of pulse $\overline{REVRS}$ clocks flip-flop 770 to the "on" condition, resulting in generation of output $\overline{GOC}$. Correspondingly, output GOC goes "low," and this results—via NAND gate 772 and inverter 774—in the setting of flip-flop 776 (see waveform NEARRST in FIG. 10D(2)). Output NEARRST indicates the "backward" mode of operation of the chair 8 (FIG. 2).

Thus, with reference to FIG. 10D(2), when the chair has rotated through three and a fraction turns, it stops, the motor reverses, and reverse rotation begins. Accordingly, the next time that the counter 662 (FIG. 10B) assumes a value of three (the prescribed value of rotations), the output MATCH is issued, but this time the output FWD is "low," and the NAND gate 762 accordingly produces a "low" output.

It is to be noted that flip-flop 766 has its reset input connected to a series connection of NAND gate 778 and inverter 780, NAND gate 778 performing an OR operation between input $\overline{REVRS}$ and input $\overline{RST}$. By virtue of this arrangement, flip-flop 766 is reset under either of two conditions: (1) generation of the negative pulse $\overline{REVRS}$; or (2) occurrence of the reset input $\overline{RST}$. Up/Down flip-flop 782 is set by the $\overline{Q}$ output of flip-flop 766 when flip-flop 766 first goes "on," issuing the output DOWN, indicating the down-count mode of operation of the counter 662 (FIG. 10B).

Referring to FIGS. 10A and 10B, when counter 662 arrives at a zero count, decoder 664 issues output $\overline{ZERO}$. Furthermore, NAND gate 626 (FIG. 10A) performs an AND operation with respect to inputs ZERO and NEARRST, and as a result of the OR operation of NAND GATE 608, the output RST is issued by the arrangement of FIG. 10A. See the timing diagram of FIG. 10D(2). As previously explained, with reference to FIG. 10A, this output RST lasts for 0.1 seconds as a result of the operation of one-shot 616, which deactivates NAND gate 608 after that time period.

Upon occurrence of RST, flip-flop 776 (FIG. 10D(1)) is reset, and the output NEARRST goes "low." Thus, termination of the "backward" mode of operation of the rotatable chair 8 (FIG. 2), is indicated.

It is to be noted that, as a result of signal $\overline{REVRS}$ going "low," during reversal of the rotation of the chair 8 (FIG. 2), an "automatic stop" operation can be achieved. Specifically, referring to FIG. 10D(1), when Automatic Stop switch 784 is closed, $\overline{STOP2}$ is produced—via NAND gate 786 and inverter 788—whenever $\overline{REVRS}$ goes "low." The output $\overline{STOP2}$ turns off the Run filp-flop 700, and sets a Hold flip-flop 790. The output HOLD is AND'ed with BLINK in NAND gate 792, resulting in HLDBLNK, the latter being provided—as previously discussed—to NAND gate 714 in FIG. 10C, for the purpose of generating the CHRDYON (Chair Ready On) indicator. In addition, the HOLD output is provided to NAND gate 756, the other input of which receives the "set" output of flip-flop 750, the latter being set by actuation of the start switch (reception of signal STRSW). Thus, actuation of the start switch results in reverse rotation of the chair 8 (FIG. 2).

Besides being stopped automatically, the chair 8 can, of course, be stopped manually, by actuation of the Stop switch, generating signal STOPSW. The latter signal is a "set" input to flip-flop 794, resulting in generation of output $\overline{STOP}$. The latter output turns off the Run flip-flop 700, resulting in stopping of rotation of the chair.

Finally, manual restart of the chair 8, for the purpose of reverse rotation, as previously discussed, turns on the Run flip-flop 700, and—shortly thereafter—the Hold flip-flop 790 (previously set as a result of automatic stopping via $\overline{STOP2}$) is now reset via $\overline{RUN}$ input thereto.

Referring now to FIG. 10E, portion L2'' receives input MTRSWON from circuit 462 as a result of the actuation of switches $S_2$ in the operator control section 450 (FIG. 9A), and receives input RELBRK from circuit 532 (FIG. 9E). In order for the brake associated with the chair 8 (FIG. 1) to be released, it is necessary that both MTRSWON and RELBRK be "high"—this will cause the output of inverter 802 to be "high," which will turn on transistor Q1, and accordingly turn off transistor Q2. As a result, $\overline{BRAKE}$ will be "high," and the dynamic braking relay 322 (FIG. 7A) will be released (deactivated).

However, when either MTRSWN or RELBRK go "low," the output of NAND gate 800 will go "high," the output of inverter 802 will go "low," transistor Q1 will be turned off, and transistor Q2 will be turned on. As a result, $\overline{BRAKE}$ will go "low," thus activating the dynamic braking relay circuit 322 (FIG. 7A).

Logic portion L2'' (FIG. 10E) also has a manual brake on/off switch 804 which, in the downward position, manually allows the portion L2'' to function as described above. Conversely, when switch 804 is in the upward position, brake application is removed from the chair 8 for manual positioning. In this case, test warning indicator DS10 in operator control section 450 (FIG. 9A) comes on, as a result of $\overline{TESTI}$ being "low" (connected to ground).

FIGS. 10F and 10G are detailed schematics of portions L3 and L3', respectively, of the logic section 62 of FIG. 2.

Referring first to FIG. 10G, portion L3' receives inputs RUN1B (output of Run flip-flop 700 of FIG. 10D(1)) and FWD (output of Forward/Backward flip-flop 704 of FIG. 10D(1)). Switch SC of portion L3' is a push-button switch actuated by the operator in order to manually rotate the chair 8 (FIG. 2). NAND gates 870 and 878 perform an AND operation with respect to the inputs thereto, and NAND gate 872 OR's the outputs of gates 870 and 878. Thus, NAND gate 872 issues an output under either of two conditions: (1) actuation of switch SC in the manual mode (MANMODE) of operation, or (2) receipt of Run flip-flop output RUN1B in the non-manual mode of operation.

NAND gates 880, 882 and 884 operate in a similar manner, so that NAND gate 882 issues an output under either of two conditions: (1) receipt of Forward/Backward flip-flop output FWD in the non-manual mode of operation, or (2) actuation of switch SD (to designate backward rotation) in the manual mode of operation.

NAND gate 876 issues output $\overline{RUNFWD}$ (provided to portion L3 of FIG. 10F) provided that the following two conditions both exist: (1) running of the chair has been ordered either manually or automatically, and (2) either backward rotation of the chair has been manually designated, or forward rotation of the chair has been non-manually designated.

Finally, NAND gate 886 and inverter 884 combine to issue $\overline{RUNBKD}$ (provided to portion L3 of FIG. 10F) under the following conditions: (1) running has been designated either manually or automatically, and (2) neither manual backward rotation nor automatic forward rotation have been designated.

Referring now to FIG. 10F, basically, the input $\overline{RUNFWD}$ will cause a current to flow into the negative input of op amp 822, but this current will not be applied instantaneously because of the RC time constant associated with resistor 830 and capacitor 832. The current into op amp 822 will cause a voltage output from op amp 822. This voltage output is, preferably, +5 volts, as adjusted by potentiometer Pf associated with op amp 822.

The input $\overline{RUNBKD}$ (which is mutually exclusive from $\overline{RUNFWD}$, as dictated by the logic of FIG. 10G) will cause a different output of op amp 822. Again, as stated above, this voltage output of op amp 822 is preferably −5 volts.

Finally, the input $\overline{RUNSLOW}$ will cause the $\overline{RUNBKD}$ output to be decreased in magnitude (preferably, from −5 volts to −2.5 volts). $\overline{RSLOW}$ will be "on" only during system reset (as dictated by previously described signal RST).

The above-described input signals processed by the portion L3 originate mainly in previously described portions L2, L2' and L2'' of FIGS. 10C, 10D(1) and 10E, respectively. Portion L3 (FIG. 10F) contains switches SA and SB which provide the capability of selecting manual operation of the chair motor 50 (FIG. 2), for example, for the purpose of testing the system.

Inputs $\overline{RUNBKD}$ and $\overline{RUNFWD}$ are provided to optical coupler devices 810 and 824, respectively. When input $\overline{RUNBKD}$ goes "low," current is caused to flow through resistor 812, turning off NPN transistor 814, resulting in application of a negative current via resistors 816 and 820 to op amp 822. As a result, op amp 822 provides a negative output.

Conversely, when $\overline{RUNFWD}$ goes "low," optical coupler device 824 causes current to flow through resistor 826, turning off transistor 828, and resulting in a negative current input to the op amp 822. As a result, op amp 822 provides a positive (+15 volts) input.

When input $\overline{RSLOW}$ goes "low" in the non-manual mode of operation of chair 8 (FIG. 2), a "low" input is detected by optical coupler device 826. It is to be noted that non-manual operation is indicated by $\overline{MANRUN}$ going "high," as applied to NAND gate 829, the other input of which is provided with $\overline{RSLOW}$, inverted (to RSLOW) by inverter 836. Optical coupler device 826, in response to detection of a "low" input, turns off PNP transistor 832, and a negative voltage is provided to the negative input of op amp 822. However, resistors 834 and 838 are twice the impedance value of corresponding resistors (discussed above) 816, 830 and 820, 834 (respectively). Accordingly, the input to op amp 822 is not as large a negative current, but half that. As a result, op amp 822 issues an output one-half the magnitude of the previously discussed outputs.

When switches SA and SB are in the "normal" position, the output of op amp 822 is provided—via resistors 848 and 850—to output terminal MTRSPD1, this output (as will be recalled) being an analog input to circuit 456 (FIG. 9C), the latter circuit producing further analog output MTRSPD which is a speed-indicating input to linear servo controller 320 (FIG. 7A), and determines the speed of operation of the motor 50 which drives the chair 8. Accordingly, "low" inputs at $\overline{RUNFWD}$ and $\overline{RUNBKD}$ result in positive and negative voltage outputs MTRSPD1, corresponding to forward and reverse rotation of the chair at full speed. Moreover, a "low" input $\overline{RSLOW}$ results in a negative voltage output MTRSPD1, reduced by one-half in value, so as to result in reverse rotation at half speed.

Portion L3 includes switches SA and SB which are actuable to a "manual" position. In such position, output MTRSPD1 is connected via potentiometer 852 to the output of op amp 822, with the result that manual adjustment of motor speed MTRSPD1 can be accomplished. Moreover, when switch SB is moved to the "manual" position, output $\overline{MANRUN}$ goes "low" indicating the "manual run" mode of operation, while output MANMODE goes "high," resulting in the same indication. In addition, output $\overline{TEST1}$ (discussed previously with reference to FIG. 10A) goes "low," so that the test warning display indicator DS10 (FIG. 9A) will be caused to blink as a result of output TWLON (FIG. 10A).

Finally, portion L3 is provided with a potentiometer 844 which is a zero-bias potentiometer, utilized to insure that the output of op amp 822 is zero volts when both $\overline{RUNFWD}$ and $\overline{RUNBKWD}$ are "high" (that is, both RUNFWD and RUNBKWD are "off").

FIGS. 10H and 10I are detailed schematics of portions L4 and L4', respectively, of logic section 62 of FIG. 2. The logic circuitry in portions L4 and L4' receive signals from the various switches on the operator control section 450 (FIG. 9A), and as well from limit switches on the motors 68 and 74 (FIG. 2) which raise and lower the flasher 70 and stripe cage 76, respectively. As a result of the reception of such signals, the logic circuitry in portions L4 and L4' generally produce signals that operate relays in relay panel 20 (FIGS. 2 and 8) previously discussed so as to raise and lower the flasher 70 and stripe cage 76, and to also rotate the stripe cage 76. Finally, logic portions L4 and L4' provide status output signals which indicate, to the processor 34 (FIG. 2), the status of the two devices—flasher 70 and stripe cage 76.

Referring to portion L4 of FIG. 10H, when $\overline{INIT}$ goes "high," flip-flop 900 is turned on. As a result, the Q output thereof is "low."

Limit switches 902 and 904 are "limit up" and "limit down" switches, respectively, associated with the optokinetic device 16. Specifically, referring to FIG. 8, motor 74—which raises and lowers the stripe cage 76—includes, in the preferred embodiment, the switches 902 and 904 (FIG. 10H). Switches 902 and 904 are normally closed, but are selectively opened when the stripe cage 76 is raised by the motor 74 to its upper limit and lower limit, respectively.

Upon system initialization, the stripe cage 76 will normally be in its uppermost position, such that switch 902 will be open and switch 904 will be closed. Moreover, resetting of the system ($\overline{RST}$), in combination with upper limit switch 902 being open (LIMUPOF) and operator actuation of switch $S_8$ (to lower the stripe cage—$\overline{DNCGSW}$), results in operation of Up flip-flop 906 and Down flip-flop 908 via NAND gate 910 to turn the motor on ($\overline{TRMTRON}$ goes "low") and to designate lowering of the stripe cage 76 (via $\overline{TRMTRDN}$ going "low"). Turn-on of the motor 74 and lowering of the stripe cage 76 is effected by signals $\overline{TRMTRON}$ and $\overline{TRMTRDN}$, respectively, in the manner previously described with reference to FIG. 8.

When the lower limit of the stripe cage 78 is reached, switch 904 opens, and the "stripes ready" condition ($\overline{STRPRDY}$) is indicated via NAND gate 912, inverter 914 and NPN transistor 916, provided that switch $S_{11}$ (in operator control section 450 of FIG. 9A) has been actuated to energize the stripe cage light 400 and stripe gate rotation motor 74' (FIG. 8).

NAND gate 912 issues output LITEON via inverter 918 and TRNCG via inverter 920, provided to circuits 532 and 533 (FIG. 9E), respectively, so as to provide further outputs $\overline{LITEON}$ and +CGMTR/−CGMTR to relay panel 20 and motor 74' (FIG. 8). It will be recalled that, with reference to FIG. 8, $\overline{LITEON}$ going "low" results in application of power to stripe cage light 400, while inputs −CGMTR and +CGMTR to motor 74' result in forward and reverse rotation, respectively, of the stripe cage 76 under the influence of motor 74'.

The direction of rotation of the stripe motor 76 (FIG. 8) is designated by switch $S_{14}$ in operator control section 450 (FIG. 9A). This results in selective generation of inputs $\overline{LFTSW}$ and $\overline{RHTSW}$ to NAND gates 922 and 924 which—via inverters 926 and 928—provide outputs DATIN13 and DATIN14 to the computer processor 34 (FIG. 2). DATIN13 indicates the "stripes right" condition of rotation, while DATIN14 indicates the "stripes on" condition.

Finally, previously mentioned signal LITEON—commanding turn on of the stripe cage light 400 (FIG. 8)—is inhibited when raising of the stripe cage is commanded by actuation of switch $S_7$ ($\overline{UPCGSW}$) via Up flip-flop 906, NAND gate 912 and inverter 918. In a similar manner, output TRNCG (the turn cage command) is also inhibited via NAND gate 912 and inverter 920.

Referring to FIG. 10I, portion L4' includes a flip-flop 950 which is set by turn-on of the system power, at which time the Q output of flip-flop 950 is provided via NAND gates 952 and 954 to one-shot 956, which generates a short (preferably, 0.15 seconds) pulse $\overline{Q}$. It is to be noted that NAND gate 952 performs an OR operation with respect to the inputs thereto, while NAND gate 954 permits the output of NAND gate 952 to be blocked by $\overline{TRMTRON}$ and LIMDNOF (the latter two signals being received from portion L4 of FIG. 10H).

The $\overline{Q}$ output of one-shot 956 results in generation, by NAND gate 958, of the output FLMTRON (Flasher Motor On), the latter comprising a "high" input to circuit 532 (FIG. 9E), generating a low output $\overline{FLMTRON}$, which causes application of power to the flasher motor 68 (FIG. 8). In addition, the $\overline{Q}$ output of one-shot 956 resets the flip-flop 950.

Portion L4' also receives an input UPFLSW (as a result of operator actuation of switch $S_9$ in operator control section 450 of FIG. 9A for the purpose of raising the flasher). Input UPFLSW sets flip-flop 960, and the "set" output thereof is provided via NAND gates 952 and 954 (so long as it is not blocked by $\overline{TRMTRON}$ and LIMDNOF provided to NAND gate 954). As a result, operator actuation of the "flasher up" switch S9 (FIG. 9A) results in automatic turn-on of the flasher motor (FLMTRON).

In a similar manner, operator actuation of "flasher down" switch S8 in operator control section 450 results in setting of flip-flop 962 via DWNFLSW, and the set output thereof is provided—via NAND gates 964 and 958—to produce FLMTRON (again, presuming that NAND gate 964 is not inhibited by $\overline{\text{TRMTRON}}$ and LIMDNOF).

FIG. 10J is a detailed schematic portion L5 of logic section 62 of FIG. 2. Portion L5 generates SYNCIN and 5MSSAMP which—via photostimulator 72 (FIG. 2)—operate the flasher 70, such operation being conducted under the control of computer processor 34 via EOG interface 30 and portion L5. In general, portion L5 actuates photo-stimulator 72 to send a trigger pulse to the flasher 70 to produce a single flash on command. Furthermore, the CEOG system can, again via photostimulator 72, arrange for stimulation of the subject 2—and thus, transmission of electrode test data to the computer processor 34—once during any given time interval (for example, 2.5 milliseconds, 5 milliseconds, etc.).

Referring to FIG. 10J, portion L5 includes flip-flops 970 and 972 which are reset by a power-on initialization input ($\overline{\text{INIT}}$) or a computer initilization input ($\overline{\text{COMPINIT}}$), provided to flip-flops 970 and 972 via NAND gate 974 and inverter 976.

The $\overline{\text{Q}}$ output of flip-flop 970 actuates one-shot device 978 and series-connected one-shot device 980 to generate short (preferably, 10 microseconds) pulses separated by a longer (preferably, 5 milliseconds) time duration, such output being designated 5MSSAMP. The latter comprises an "initiate sample" pulse provided to circuit 250 of FIG. 6D, wherein it is utilized to provide the output SAMPLE (used for ADC in FIG. 6A).

Flip-flop 972—via its $\overline{\text{Q}}$ output—actuates solenoid/switch combination 982 to cause closing of the switch so as to provide a variable (by virtue of potentiometers 984 and 986) time control to the one-shot device 980. As a result, one-shot 980 can be adjusted to provide "initiate sample" pulses of less than 5 milliseconds (preferably, 2.5 milliseconds) duration.

It is to be noted that one-shot 978 is triggered by the falling edge of the pulse output from the $\overline{\text{Q}}$ output of flip-flop 970. This falling edge is generated by flip-flop 970 in response to the D input, DOUT13—comprising a "Go bit" input from the computer processor 34 (FIG. 2). DOUT13 designates a desired stream of pulses which will occur typically at 5 millisecond intervals. Similarly, processor 34 provides input DOUT11 to the D input of flip-flop 972, and this results (as previously explained) in adjustment of one-shot 980 so as to provide a 2.5 millisecond "initiate sample" pulse separation.

It is to be noted that flip-flops 970 and 972 are clocked (at the C inputs) by computer-generated strobe input $\overline{\text{STROB0}}$, provided via inverter 988. $\overline{\text{STROB0}}$ is, as will be seen below, decoded in interface 30 of FIG. 2 (see discussion of FIG. 11D below).

Further referring to portion L5 of FIG. 10J, processor 34 (FIG. 2) generates a flash bit DOUT12, provided to the D input of flip-flop 990, the latter being clocked by computer-generated strobe $\overline{\text{STROB0}}$. The Q output of flip-flop 990 triggers one-shot 992 which generates—via inverter 994—a square wave pulse of short duration (preferably, 15 microseconds). The latter pulse is provided as an emitter input to transistor 996, the collector output of which generates flasher sync plus SYNCIN. SYNCIN is a pulse, preferably having a 25-volt "swing," and is provided to photostimulator 72 so as to synchronize the flashing light produced thereby.

Flip-flop 990 is reset either by operator-initiated reset ($\overline{\text{RST}}$) or by the $\overline{\text{Q}}$ output of one-shot 992, provided via NAND gate 998 and inverter 999.

FIG. 10K is a detailed schematic diagram of the portion L8 of logic section 62 of FIG. 2. Portion L8 uses feedback from the X mirror signal (XBACK) to generate a signal (YFIX) that is sent to the Y mirror 14 (FIG. 2)—specifically, to the Y-deflection circuitry of mirrors 14—to correct for the curvature of the light spot (laser spot) on the cylindrical walls 18 (FIG. 1) of the test station 4. This curvature results from the fact that the laser 12 is located above the head of the subject 2, and is accordingly aimed downwardly on the cylindrical walls 18.

Referring to FIG. 10K, portion L8 receives input XBACK, an analog signal provided by mirrors 14. Isolation op amp (voltage follower) 1000—in response to the positive input XBACK and the negative bias/gain-adjusted input (bias and gain are adjusted via potentiometers 1002 and 1004, respectively)—provides its output to both positive inputs of a multiplier 1006. Multiplier 1006 squares the output of amplifier 1000, and provides the result—via isolation op amp (voltage follower) 1008—as output YFIX. The latter output YFIX is provided to portion L10 (FIG. 10M) to be discussed below.

As a result of the operation of portion L8, correction or compensation for the vertical angle existing between the line-of-sight from the light source (laser) 12 and the cylindrical wall 18 (FIG. 1) and the line-of-sight between the eyes of the subject 2 and the cylindrical walls 18 is achieved.

FIG. 10L is a detailed schematic diagram of the portion L9 of logic section 62 of FIG. 2. Generally, portion L9 receives and stores four bits from a Move X register (to be subsequently explained), the four bits being designated:

DOUT10 (GO X bit)—a bit which causes scanning of the mirror in the X direction in accordance with circuitry contained in portion L10 (FIG. 10M) to be discussed below.

DOUT11 (CMPSINE)—a bit which causes scanning of the mirror in the X direction using bits 0 through 9 of the MOVX register (to be discussed below), the deflection ranging from $-30°$ to $+30°$ in 1024 increments thereof.

DOUT12 (CMPSHTR)—a bit which causes opening of the shutter 66 (FIG. 2).

DOUT13 (YSCAN)—a bit which causes scanning of the mirror in the Y direction in accordance with a signal from the portion L10 (FIG. 10M) to be discussed below.

It is to be noted that—as previously discussed—the inputs DOUT10–DOUT13 are strobed into respective flip-flops 1020–1023 by STRBMX via NAND gate 1024 and inverter 1025.

The $\overline{\text{Q}}$ output of flip-flop 1020 forms the output XSINE via NAND gate 1026. NAND gate 1026 has its other input connected to switch S13 (in operator control section 450 of FIG. 9A), such that actuation of the auto/setup switch S13 to the "setup" position (or DOUT10) will generate XSINE.

XSINE, the output of inverter 1028, is OR'ed with the $\overline{\text{Q}}$ output of flip-flop 1022 in NAND gate 1032 to provide—via transistor 1036—output $\overline{SHUT}$. $\overline{SHUT}$ is utilized to open/close the shutter 66 associated with the mirrors 14 (FIG. 2). Furthermore, $\overline{XSINE}$ from inverter 1028 is AND'ed with the Q output of flip-flop 1021 in NAND gate 1030 and inverter 1034 to provide output CMPSINE.

The respective outputs of inverter 1028 and NAND gate 1030 are OR'ed in NAND gate 1038, the latter providing a base-controlling input to transistor 1040. Transistor 1040 provides a collector output $\overline{SCNLIT}$, the latter indicating operation of the laser 12 associated with the mirrors 14 and shutter 66 (FIG. 2). It is to be noted that the $\overline{Q}$ output of flip-flop 1023 is provided via inverter 1042 in a wire-OR'ed connection to the base of transistor 1040. Thus, the presence of DOUT13 (YSCAN)—input to flip-flop 1023—also actuates the scan light.

Input signal $\overline{CMPINIT}$—provided via NAND gate 1044 and inverter 1046 whenever the computer is turned on or off—resets flips-flops 1020–1023. Input $\overline{RST}$—generated whenever $\overline{INIT}$ occurs, the operator resets the system, or the chair goes into "reset" mode—also functions to reset flip-flops 1020–1023 via inverters 1046 and 1048 and NAND gate 1044.

Portion L9 also includes flip-flop 1050 which is reset by initialization input $\overline{INIT}$ (which occurs for one second after the power to the system is turned on). Flip-flop 1050 is set by inputs WRTONLY (indicating that the computer wants to write data to one of its register addresses) and $\overline{STRBMY}$ (a strobe for loading data into the MOVY register, to be discussed below). These inputs are provided via inverter 1052 and NAND gate 1054. The $\overline{Q}$ output of flip-flop 1050 is output $\overline{STOREY}$ (to be discussed further below with respect to FIG. 10M).

Figure 10M:
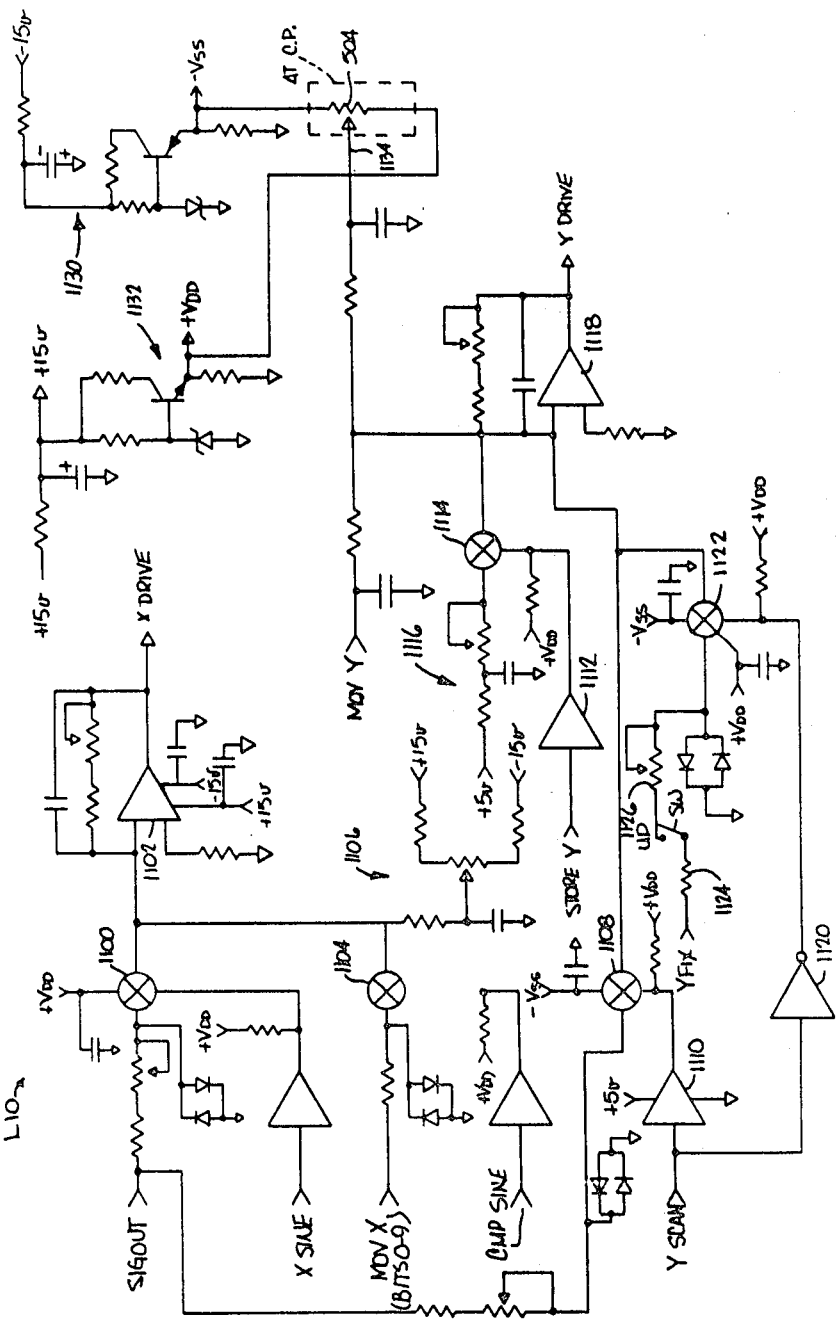

FIGS. 10M and 10N are detailed schematic diagrams of portions L10 and L10', respectively, of logic section 62 of FIG. 2. Portions L10 and L10' are responsible for performing various analog switching functions which enable the driving of the mirrors 14 (FIG. 2) in the X direction to be accomplished either under computer control or under local control. Furthermore, portions L10 and L10' are responsible for the performance of various summing and analog switching functions to accomplish the following:

(1) Control of the driving of mirrors 14 (FIG. 2) in the Y direction by both adjustment knob $P_3$ (in operator control section 450 of FIG. 9A) and computer processor 34 (FIG. 2), the latter being accomplished via a Move Y register (as will be subsequently explained).

(2) Adjustment of the Y-direction scanning of the mirrors 14 in accordance with correction signals generated by portion L8 (FIG. 10K), so as to correct for curvature of the laser spot on the cylinder walls 18 (FIG. 1), as previously described above.

(3) Origination of driving signals for Y-direction scanning of the mirrors 14 by the generating circuitry in portion L11 of FIG. 10O, as will be subsequently discussed), the latter generating the driving signals for X-direction scanning as well.

In addition to the above, portion L10' contains two buffer amplifiers provided for the purpose of feeding back the signal from the mirrors 14 (FIG. 2) so that the computer processor 34 can read and display the positions of the X mirror and Y mirror relative to the corresponding Position X and Position Y registers (discussed in more detail below).

Referring to FIG. 10M, portion L10 receives SIGOUT—an analog signal produced by portion L11 (FIG. 10O—to be discussed below); this analog signal defines a desired pattern of scanning to be performed by the laser 12/mirrors 14 (FIG. 2). In addition, portion L10 receives output XSINE—generated by portion L9 of FIG. 10L, previously discussed—the latter forming an enabling input permitting gate 1100 (preferably, a field-effect transistor analog switch) to pass SIGOUT through to the negative input of summing amplifier 1102, the positive input of which is connected to ground. As a result, summing amplifier 1102 produces mirror-driving output signal XDRIVE.

Portion L10 receives input MOVX (bits 0–9 of the MOVX register to be discussed below), and—in a similar manner—input MOVX is gated to the negative input of summing amplifier 1102 via gate 1104 enabled by input CMPSINE (generated by portion L9 of FIG. 10L, previously discussed). Proper biasing of the negative input of summing amplifier 1102 is provided by biasing circuitry 1106.

Thus, in accordance with which input, XSINE or CMPSINE, is received by portion L10, either SIGOUT (the pattern generated by portion L11 of FIG. 10O) or MOVX (the computer-generated pattern) is gated through summing amplifier 1102 to form mirror-driving output XDRIVE. Output XDRIVE is an analog input to the X-driver card (not shown), which is a conventional hardware element supplied with the mirrors 14 (FIG. 2).

Further referring to portion L10, initialization of the system ($\overline{INIT}$) results in generation of $\overline{STOREY}$, the latter being provided via amplifier 1112 as an enabling input to the switch 1114. As a result, biasing voltage provided by biasing circuitry 1116 is gated through switch 1114 to the negative input of further summing amplifier 1118.

In response to input YSCAN (designating desired Y-direction scanning in accordance with the pattern SIGOUT), switch 1108 gates SIGOUT through to the negative input of amplifier 1118. As a result, amplifier 1118 generates YDRIVE (the Y-direction driving signal for the mirrors 14 of FIG. 2) in accordance with either SIGOUT (the pattern generated by portion L11 of FIG. 10O) or MOVY (the computer-generated pattern). The inverse of YSCAN is provided by inverter 1120 as an enabling input to switch 1122, thus disabling a further input to the negative input of amplifier 1118 (and thus, the parabolic correction when using YSCAN). Specifically, when switch SW is in the upward position, input YFIX is provided via resistor 1124 and potentiometer 1126, as well as gate 1122, to the negative input of summing amplifier 1118, thus providing a correction factor (as previously discussed) for the YDRIVE output driving the mirrors 14 of FIG. 2.

Portion L10 includes circuitry 1130 and 1132 which supply voltages $-V_{ss}$ and $+V_{dd}$, respectively, and are as well used to supply voltages to potentiometer 504. Potentiometer 504 is associated with adjustment knob $P_4$ in operator control section 450 (FIG. 9A) which, as previously explained, is utilized to adjust the vertical position of the laser beam from light source 12. As a result of adjustment of potentiometer 504, the center tap thereof provides another summed input to the negative input of amplifier 1118, thus achieving necessary adjustment of the Y-direction mirror-driving output YDRIVE so as to achieve the desired vertical positioning of the light beam.

Referring to FIG. 10N, the portion L10' basically comprises an op amp (voltage-following) 1150 which receives feedback signal XBACK from the mirror driving circuitry in mirrors 14 (FIG. 2), and appropriately amplifies same to obtain the analog output POSX. The analog output POSX is, as previously described, provided via converter stage 56 (FIG. 2)—that is, the ADC portion thereof—so as to provide the computer processor 34 with a digital input representative of the mirror position. It is to be understood that portion L10' is identical to a circuit which performs the same function with respect to the feedback signal YBACK (Y-direction feedback signal from the mirrors 14) so as to generate the analog output POSY.

FIG. 10O is a detailed schematic diagram of the portion L11 of logic section 62 of FIG. 2. Basically, portion L11 includes a sine wave oscillator utilized in conjunction with establishment of a scanning pattern for the light beam generated by light source 12 in the case where manual function switch $S_{12}$ (on operator control section 450 of FIG. 9A) is set to call for scanning of the light source 12 in accordance with a sine wave pattern. As will be seen below, the frequency of the sine wave generated by the sine wave oscillator in portion L11 is controlled by various input signals corresponding to the scanning speed setting, as set by adjustment knob $P_3$ on operator control section 450. Moreover, portion L11 of FIG. 10O contains the necessary circuitry for choosing between the various scanning waveform patterns, as selected by manual function switch $S_{12}$.

Referring to FIG. 10O, device 1200 is a conventional device (preferably, an ICL8038 made by Intersil of Cupertino, Calif.). It generates, at output terminal 2 thereof, a sine wave having characteristics as determined by an adjustable sine wave timing circuit 1202 provided at the $L_{in}$ terminal of the device 1200. In addition, device 1200 provides (at terminal 9 thereof) a square wave output and (at terminal 3 thereof) a sawtooth output. As previously discussed with reference to FIG. 9C, switch $S_{12}$ is employed by the operator to designate the desired type of output. Switch $S_{12}$ generates signals $\overline{SQUAR}$, $\overline{TRINGL}$ and $\overline{SINE}$ (selectively), and these inputs are provided to corresponding relays K11, K12 and K13, respectively (FIG. 10L). As a result of selective actuation of switches K11, K12 or K13, the square wave, sawtooth or sine wave output of device 1200 is provided to the negative input of isolation amplifier 1204, the positive input of which is grounded. As a result, amplifier 1204 issues output SIGOUT. Proper biasing of the negative input of isolation amplifier 1204 is provided by biasing circuit 1206.

Device 1200 is provided, at terminal 8 thereof, with a frequency-controlling input OSREF originating in a potentiometer 496 connected in a voltage-divider arrangement with voltage-dividing resistors 498 and 500 (see FIG. 9C). It will be recalled that signal OSREF is a frequency-controlling input resulting from operator actuation of adjustment knob $P_3$ in operator control section 450 (FIG. 9A), by which the operator adjusts the horizontal speed of scanning of mirrors 14. This effect is achieved by application of the input OSREF as a frequency-controlling input to the device 1200. Finally, reference voltage inputs +VREF and −VREF are provided to supply voltage input terminals $V_{CC}$ and $V_{EE}$, respectively, of the device 1200, the latter terminals also being connected to respective supply voltage circuits 1200 and 1212.

Portion L11 is provided with ganged switches SN connected to the terminal 10 input of device 1200. When switches SN are in the downward position, a normal frequency of operation of device 1200 results. However, when switches SN are actuated to the upward position, a high-frequency of operation of device 1200 results, and this is indicated by output signal $\overline{TESTI}$ going "low."

FIGS. 11A through 11D and 11G are detailed logic block diagrams and circuit schematics of the interface 30 of the CEOG system of FIG. 2. FIGS. 11E, 11F and 11H are timing diagrams of the write (data out) sequence, read (data in) sequence and interrupt sequence, respectively, relating to the operation of the interface 30 of the CEOG system of FIG. 2.

Referring to FIG. 11A, three tristate buffers 1230, 1232 and 1234 are provided, each of which is responsive to input signal $\overline{GATVEC}$. Specifically, when $\overline{GATVEC}$ goes "low," each of tristate buffers 1230, 1232 and 1234 is actuated so that a prewired address (for example, in the preferred embodiment, address 000,154) in the processor 34 (FIG. 2) passes through the tristate buffers 1230, 1232 and 1234 to outputs DAT0-DAT15. The latter outputs are provided to the arrangement of FIG. 11B, which will be discussed further below.

Conversely, when $\overline{GATVEC}$ goes "high," tristate buffers 1230, 1232 and 1234 appear as an open circuit to output terminals DAT0-DAT15, and as a result data from DAT0-DAT9 (from processor 34 of FIG. 2) is provided to the arrangement of FIG. 11B. As a result of the "open circuit" condition of tristate buffers 1230, 1232 and 1234, outputs DAT10-DAT15 are not active.

Tristate buffers 1230, 1232 and 1234 are, in the preferred embodiment, SN74LS365 devices (manufactured by Texas Instruments).

Referring to FIG. 11B, the arrangement therein comprises bus transceiver devices 1240-1243 and tristate buffers 1244 and 1245. Bus transceivers 1240-1243 receive and respond to input $\overline{DGATE}$. Specifically, when $\overline{DGATE}$ goes "low," data DAT0-DAT15 passes through internal inverter 1246 (shown, for illustrative purposes, in device 1240 only) to terminals $\overline{DAL}$ 0-$\overline{DAL15}$ (the latter terminals representing a common data bus to the computer processor 34 (FIG. 2)), and data $\overline{DAL0}$-$\overline{DAL15}$ passes through inverter 1247 to output terminals DAL0-DAL15.

Conversely, when $\overline{DGATE}$ goes "high," data DAT0-DAT15 does not pass through internal inverter 1246, but again data $\overline{DAL0}$-$\overline{DAL15}$ passes through inverter 1247 to output terminals DAL0-DAL15.

Output terminals DAL0-DAL11 are connected as inputs to tristate buffers 1244 and 1245, which are responsive to input $\overline{GATWRIT}$. More specifically, when $\overline{GATWRIT}$ goes "low," inputs DAL0-DAL11 are passed through to outputs DTOA0-DTOA11, the latter (as will be recalled from above) providing inputs to the DAC circuitry in converter stage 56 (FIG. 2). Conversely, when $\overline{GATWRIT}$ goes "high," tristate buffers 1244 and 1245 are open-circuited, thus precluding any output DTOA0-DTOA11.

To summarize the above, when $\overline{DGATE}$ goes "low," data DAT0-DAT15 are written to the computer via the computer bus ($\overline{DAL0}$-$\overline{DAL15}$). Conversely, when $\overline{DGATE}$ goes "high" and $\overline{GATWRIT}$ goes "low," data is provided by the computer processor 34 (FIG. 2) via the computer bus ($\overline{DAL0}$-$\overline{DAL15}$), bus transceivers 1240-1243, tristate buffers 1244 and 1245, and output terminals DTOA0-DTOA11, to the DAC circuitry in converter stage 56 (FIG. 2).

It is to be noted that—in the preferred embodiment—computer-generated control data (specifically, $\overline{\text{DOUT}}$, $\overline{\text{DIN}}$, $\overline{\text{SYNC}}$, $\overline{\text{WTBT}}$, $\overline{\text{IAKI}}$, $\overline{\text{BS7}}$ and $\overline{\text{INIT}}$) are transmitted over the computer bus to further bus transceiver devices (not shown)—identical to bus transceivers 1240-1243—so as to produce at the output thereof corresponding control data DOUT, DIN, SYNC, WTBT, IAKI, BS7 and INIT. These control data are utilized in a manner to be described below.

Finally, bus transceivers 1240-1243 are, in the preferred embodiment, bus transceivers, Model No. DM8838 (manufactured by National Semiconductors). Moreover, tristate buffers 1244 and 1245 are, in the preferred embodiment, buffer devices SN74LS365 (manufactured by Texas Instruments).

Referring to FIG. 11C, interface 30 (FIG. 2) further comprises tristate buffer devices 1250-1253 and latch circuit 1254.

In operation, device 1250 responds to $\overline{\text{GATWRIT}}$ going "low," to pass data DAL8-DAL13 (the outputs of bus transceiver devices 1240 and 1241, respectively, of FIG. 11B, just discussed above) to output terminals DOUT8-DOUT13. Thus, the latter outputs are derived indirectly from the corresponding inputs $\overline{\text{DAL 8-DAL13}}$ (provided via the computer bus—FIG. 11B) to bus transceiver devices 1240 and 1241, and in particular are control bits 8-13 in a control word register (to be discussed below). Conversely, when input $\overline{\text{GATWRIT}}$ is "high," tristate buffer 1250 is open-circuited, and data does not pass therethrough.

Tristate buffer 1251 responds to $\overline{\text{GRPISTB}}$ (a "Group 1" strobe) going "low," to connect outputs DAT10-DAT15 to ground, thus creating "low" (zero) output conditions at DAT10-DAT15. It is to be noted that $\overline{\text{GRPISTB}}$ goes "low" whenever analog-to-digital converted data (from converter stage 56 to FIG. 2) is to be entered in the processor 34. Referring back to FIG. 6A, since converters A/D1-A/D5 provide 10 bits of data (DAT0-DAT9), tristate buffer 1251 performs the necessary function of inserting leading zeros into the most significant six bit positions (DAT10-DAT15). Referring back to FIG. 11B, it will be recalled that $\overline{\text{DGATE}}$ goes "low," when data input to the computer is to be achieved. Accordingly, DAT0-DAT15 from tristate buffers 1250-1252 are passed through devices 1240-1243 to the computer bus ($\overline{\text{DAL0-DAL15}}$).

Further referring to FIG. 11C, tristate buffer 1252 responds $\overline{\text{STOBI}}$ (a "status in" strobe) going "low," to pass data DATIN9-DATIN14, provided by logic section 62 (of FIGS. 2 and 10A-10O), to outputs DAT9-DAT14. The latter is provided to the computer bus via devices 1240 and 1241 (FIG. 11B), as previously described. When $\overline{\text{STROBI}}$ is "high," tristate buffer 1252 blocks transfer of data.

Latch circuit 1254 responds to STROB0 (a "control register" strobe) to strobe data DAL0-DAL4 (received from processor 34 of FIG. 2 via the computer bus and devices 1242 and 1243 of FIG. 11B) into latch circuit 1254. Tristate buffer 1253 responds to $\overline{\text{STROBI}}$ (a "status register" strobe) going "low," to send data DAL0-DAL4 latched by device 1254 to outputs DAT0-DAT4, the latter being provided to the computer bus via devices 1242 and 1243 of FIG. 11B. In addition, tristate buffer 1253 receives input DOSAMP (a "write busy" signal set in the logic whenever a write operation is to be performed), and provides DOSAMP to output DAT15 in response to $\overline{\text{STROBI}}$ going "low." When $\overline{\text{STROBI}}$ goes "high," tristate buffer 1253 blocks transfer of data therethrough.

Figure 11D:
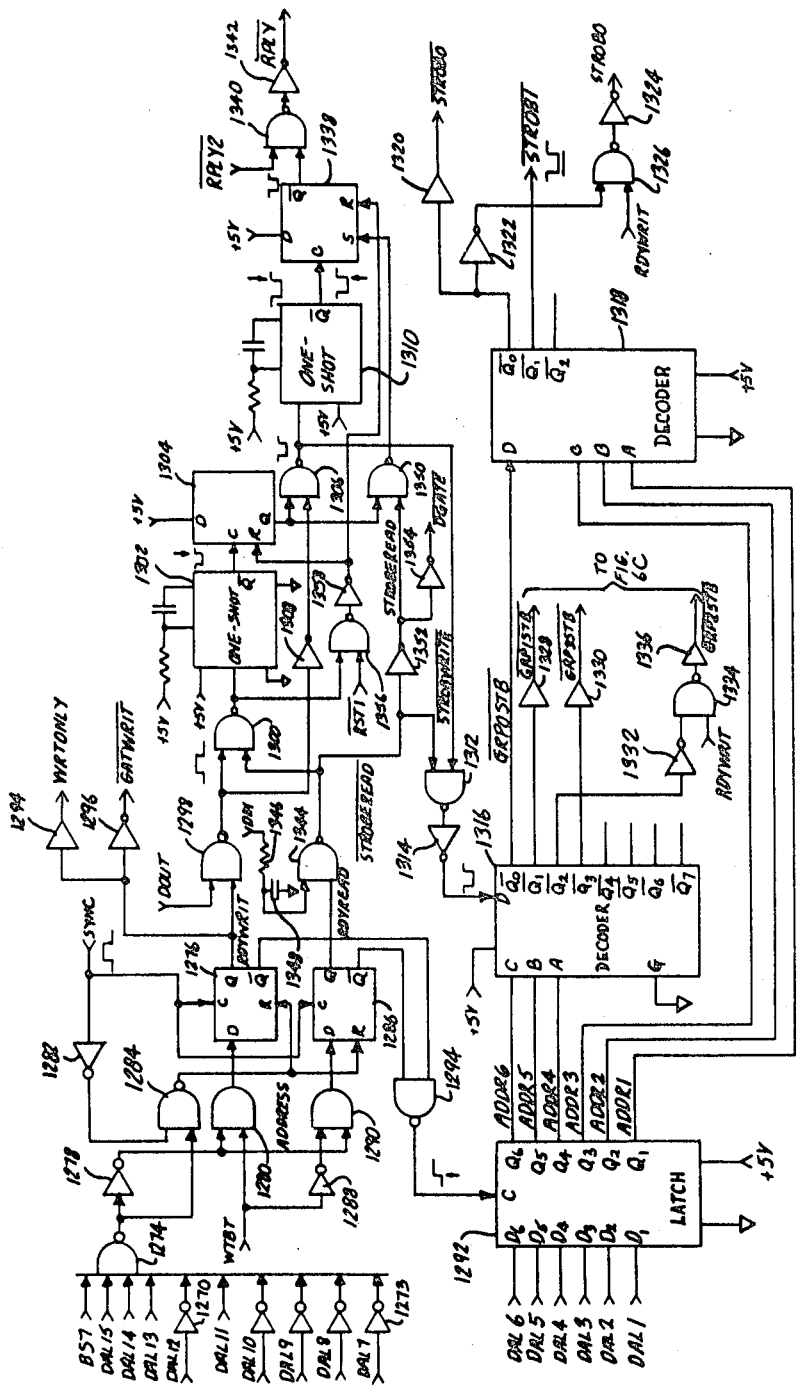
Figure 11E:
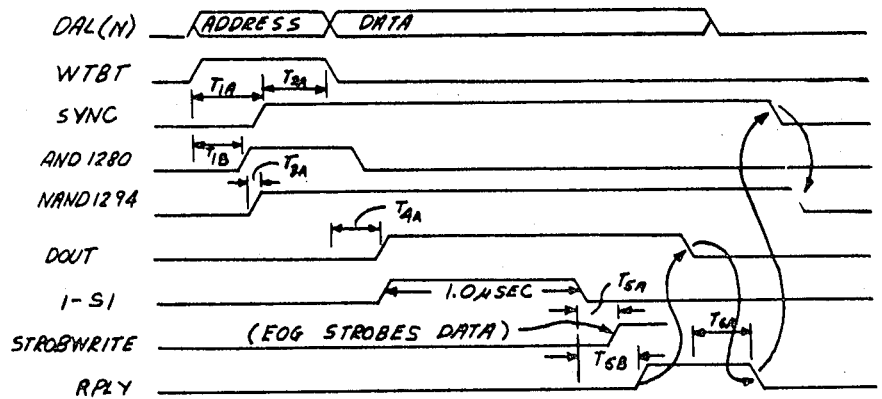
FIGS. 11E, 11F and 11H are timing diagrams relating to write (data out), read (data in) and interrupt operations, respectively, as carried out in the interface 30 of the CEOG system of FIG. 2.
Figure 11F:
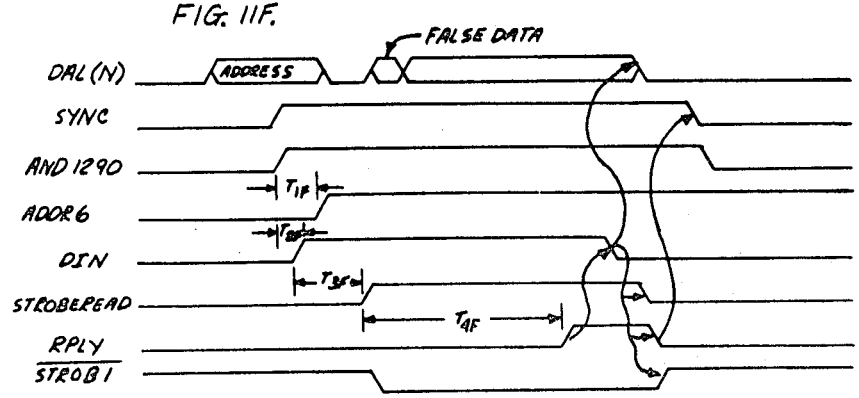
Figure 11H:
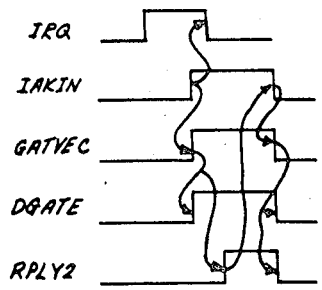

FIG. 11D illustrates the read/write decoding and control circuitry in interface 30 of FIG. 2, and will now be explained in conjunction with timing diagrams FIGS. 11E and 11F, respectively.

Referring to FIGS. 11D and 11E, inverters 1270-1273 receive inputs DAL12, DAL10, DAL9, DAL8 and DAL7, respectively, from the circuitry of FIG. 11B. NAND gate 1274 receives inputs BS7, DAL15, DAL14, DAL13 and the outputs of inverters 1270-1273, and decodes these inputs so as to derive a logic one output whenever inputs (address line inputs) DAL7-10, DAL12-15 indicate a predetermined block of addresses in processor 34 (FIG. 2). In this particular case, inputs DAL7-DAL10 and DAL12-DAL15 indicate address blocks 164,0xx or 164,1xx. More specifically, DAL0-DAL17 are address inputs from the processor 34 of FIG. 2, and—when the various DAL bits have the values shown in Table 1 (below)—corresponding address blocks are indicated. t,1010

When input BS7 is logic 1 ("on"), and when NAND gate 1274 decodes the desired address blocks, the computer has—via its address inputs DAL0-DAL17—called for data for the desired addresses. Accordingly, the output of NAND gate 1274 sets flip-flop 1276—via inverter 1278 and AND gate 1280—provided that the WTBT input to AND gate 1280 is "high," indicating a write operation (that is, sending of data to the computer). Input SYNC (an address sync pulse) is applied to the clock input of flip-flop 1276, so as to strobe the output of AND gate 1280 into flip-flop 1276, resulting in RDYWRIT going "high." SYNC is further provided—via inverter 1282—to NAND gate 1284, the other input of which receives the decoder output of NAND gate 1274. Thus, so long as $\overline{\text{SYNC}}$ is "low," or so long as the output of NAND gate 1274 is "high" (indicating that the desired address block has not been decoded as called by the computer), the flip-flop 1276 cannot be reset by NAND gate 1284. However, once either SYNC goes "high" or NAND gate 1274 goes "low," flip-flop 1276 is reset.

Whereas the above has described achievement of the "ready write" condition (flip-flop 1276 being designated the Ready Write flip-flop), the same basic operation takes place with respect to the Ready Read flip-flop 1286. When input BS7 is logic 1 ("on"), and when WTBT goes "low," indicating a "read" operation, and when a desired address block has been decoded by NAND gate 1274, Ready Read flip-flop 1286 is set via inverter 1288 and AND gate 1290. Flip-flop 1286 is strobed (via its C input) and reset (via its R input) in the same manner as described above with respect to flip-flop 1276.

The arrangement of FIG. 11D also includes latch circuit 1292 which receives computer-generated addresses DAL1-DAL6 from the arrangement of FIG. 11B. Latch 1292 is strobed by NAND gate 1294 whenever either of flip-flops 1276 and 1286 are set. Referring to the timing diagram of FIG. 11E, computer-generated address data DAL(N), N=1-6, are provided via computer bus $\overline{\text{DAL1-DAL6}}$ (FIG. 11B). WTBT (FIG. 11E) goes "high," indicating a write operation, enabling AND gate 1280 to set Ready Write flip-flop 1276 when the desired address block is decoded by NAND gate 1274. (This, preferably, occurs no more than 20 nanoseconds after WTBT going "high.") Once Ready Write flip-flop 1276 is set, NAND gate 1294 goes "high," preferably within a maximum of 14 nanoseconds after AND gate 1280 has gone "high." As indicated earlier, the "high" output of NAND gate 1294 strobes address data (from the processor 34 of FIG. 2) into latch 1292.

Returning to FIG. 11D, when flip-flop 1276 is set by AND gate 1280, and output RDYWRIT is issued, the latter output provides further outputs WRTONLY (via amplifier 1295) and $\overline{\text{GATWRIT}}$ (via inverter 1296). Output RDYWRIT is also provided to NAND gate 1298, the other input of which receives signal DOUT, which goes "high" when the computer has begun putting out data (preferably, at least 25 nanoseconds after data output begins—see the timing diagram of FIG. 11E). NAND gate 1298 performs an AND operation with respect to inputs DOUT and RDYWRIT, and the output of NAND gate 1298 is provided—via NAND gate 1300 (which performs an OR operation)—to trigger one-shot device 1302. One-shot device 1302 issues a short (preferably, one microsecond) negative pulse, the trailing edge of which triggers flip-flop 1304.

The Q output of flip-flop 1304 is provided to NAND gate 1306, the other input of which receives the inverted (via inverter 1308) output of NAND gate 1298. NAND gate 1306 performs an AND operation with respect to the inputs thereto so as to issue a negative pulse, the leading edge of which triggers further one-shot device 1310. The output of NAND gate 1306 is designated $\overline{\text{STROBWRITE}}$, and this output is provided as one input to NAND gate 1312 which performs an OR operation with respect thereto. The output of NAND gate 1312 is provided, via inverter 1314, as a strobe input to decoder 1316 which, at its A-C inputs, receives address inputs ADDR4-ADDR6 from latch 1292. The further address outputs ADDR1-ADDR3 of latch 1292 are provided directly to a further decoder 1318 which is strobed (at its D input) by the $Q_0$ output of decoder 1316.

In short, decoder 1316—as a result of the ADDR4-ADDR6 inputs thereto and $\overline{\text{STROBWRITE}}$—creates groups of strobe signals $\overline{\text{GRP0STB}}$, $\overline{\text{GRP1STB}}$, $\overline{\text{GRP2STB}}$ and $\overline{\text{GRP3STB}}$. Outputs $\overline{\text{GRP1STB}}$-$\overline{\text{GRP3STB}}$ are provided to corresponding decoders 192, 194 and 196 (FIG. 6C), wherein a decoding operation takes place so as to generate further appropriate strobe inputs STROBN for use in the DAC circuitry (FIG. 6E) of converter stage 56 (FIG. 2). Output $\overline{\text{GRP0STB}}$ from decoder 1316 is provided to further decoder 1318, which also receives address inputs ADDR1-ADDR3 from latch 1292. As a result of its operation, decoder 1318 generates output $\overline{\text{STROB0}}$ (via amplifier 1320), output STROB0 (a "control word" strobe generated via inverters 1322 and 1324 and NAND gate 1326), and output $\overline{\text{STROB1}}$ (a "status word" strobe).

To summarize, the circuitry of FIG. 11D decodes the address line inputs DAL1-DAL6, and generates the various groups of strobe signals (GRP0STB, GRP1STB, GRP2STB and GRP3STB) which are variously sent to the logic section 62 (FIGS. 2 and 6A-6E). These groups of strobe signals insure that the computer processor 34 (FIG. 2) retrieves the proper data from, or stores the proper data in, proper address locations in memory, while properly timing the various transfer and analog-to-digital (or digital-to-analog) conversion functions.

It will be recalled that the leading edge of the output of NAND gate 1306 triggered one-shot 1310. Subsequently, the trailing edge of the output of one-shot 1310 triggers (sets) flip-flop 1338. The Q output of flip-flop 1338 is accordingly a negative pulse which—via NAND gate 1340 and inverter 1342—causes output $\overline{\text{RPLY}}$ to go "low," the latter being provided to the computer processor 34 (FIG. 2) via the computer bus. NAND gate 1340 also receives $\overline{\text{RPLY2}}$—generated by the circuitry of FIG. 11G during device (i.e., CEOG system) interrupt of the computer—and performs an OR operation so that $\overline{\text{RPLY}}$ goes "low" either upon the occurence of the $\overline{Q}$ negative pulse output of flip-flop 1338 or upon $\overline{\text{RPLY2}}$ going "low."

Finally, after some unknown time has passed (thus, amounting to asynchronous operation), input DOUT (received via the computer bus, as explained above in discussion of FIG. 11B) goes "low" (see the timing diagram of FIG. 11E), so that the output of NAND gate 1300 goes "low." This "low" signal passes through NAND gate 1356 (acting as an OR gate) and inverter 1358 to reset flip-flops 1304 and 1338, resulting in output $\overline{\text{RPLY}}$ going "high" (or RPLY going "low")—see the timing diagram of FIG. 11E. Shortly thereafter, signal SYNC also goes "low," and the write (data out) sequence is completed.

Further referring to the timing diagram of FIG. 11E, in the preferred embodiment, the time lapses shown therein are preferably as follows. Time lapse $T_{1A}$ is preferably 75 nanoseconds at the minimum; $T_{1B}$ is preferably 66 nanoseconds maximum (inlcuding a 20 nanosecond set-up time); $T_{2A}$ is preferably 25 nanoseconds minimum; $T_{3A}$ is preferably 14 nanoseconds maximum; $T_{4A}$ is preferably 25 nanoseconds minimum; $T_{5A}$ is preferably 190 nanoseconds minimum; $T_{5B}$ is preferably 220 nanoseconds minimum; and $T_6$ is preferably 120 nanoseconds maximum (typically, 60 nanoseconds). The above preferred time durations are based on the particular hardware utilized in the preferred embodiment of the CEOG system, as discussed above with respect to FIGS. 11A-11D.

Referring to the timing diagram of FIG. 11F, a read (data input to the computer) operation takes place as follows. The computer generates address inputs DAL(N), which inputs are provided to latch 1292 of FIG. 11D. The computer processor 34 (FIG. 2) further generates SYNC which is provided as a strobe input to flip-flop 1286 (the Ready Read flip-flop). This strope (SYNC) sets flip-flop 1286 if its D input is a logic one on the leading edge of SYNC.

So long as WTBT is "low," indicating a read operation, AND gate 1290 provides a logic one at the D input of flip-flop 1286 in response to detection of the desired address block (so long as BS7 is logic 1 ("on")), as decoded by NAND gate 1274 in conjunction with inverter 1278. NAND gate 1344 performs an AND operation with respect to inputs RDYREAD (from flip-flop 1286) and DIN (indicating that the computer is ready to receive input data) so as to generate $\overline{\text{STROBEREAD}}$. DIN is provided to NAND gate 1344 via an RC (delay) network—resistor 1346 and capacitor 1348—so as to insure a necessary time delay (preferably 60 nanoseconds) between the occurrence of SYNC and the leading edge of DIN.

$\overline{\text{STROBEREAD}}$ going "low" strobes decoder 1316 (via NAND gate 1312 and inverter 1314) so as to decode the inputs ADDR6-ADDR4 provided by latch 1292. Decoders 1316 and 1318 function as previously described above to generate the groups of strobe signals $\overline{\text{GRP0STB}}$, $\overline{\text{GRP1STB}}$, ... and STROB0, $\overline{\text{STROB0}}$, ...

The signals generated by STROBEREAD each gate a particular set of data (e.g., STROB10 will gate data from channel 1 in the A/D section of FIG. 6A) onto the data lines DAT0–DAT9. At the same time, lines DAT10–DAT15 will be zeroed by GRPISTB as shown in FIG. 11C.

Furthermore, STROBEREAD going "low" causes one-shot 1302 to be triggered. After 1 microsecond, the trailing edge of the signal from one-shot 1302 sets flip-flop 1304. The output from flip-flop 1304 is AND'ed with STROBEREAD in NAND gate 1350 to produce the signal that sets flip-flop 1338 via its S input. RPLY goes "low" in response to setting of flip-flop 1338, the latter acting via its $\bar{Q}$ output, NAND gate 1340 and inverter 1342.

In the meantime, STROBEREAD generates DGATE via inverters 1352 and 1354. Inverter 1354 is an open-collector device, which is to say that its output may be connected to other open-collector outputs which also generate DGATE (as seen later). It will be recalled that DGATE was used (in FIG. 11B) to put data DAT0–DAT15 on the bus lines DAL0–DAL15. Once DIN goes "low" STROBEREAD goes "low" (via the operation of NAND gate 1344 and inverter 1352). The reset (R) terminal of flip-flop 1338 will be accordingly enabled by NAND gates 1300 and 1356 (the latter of which performs an OR operation with respect to input RSTI) and inverter 1358. Thus, flip-flop 1338 will be reset, causing RPLY to go "high" via the operation of NAND gate 1340 and inverter 1342. Subsequently, the computer will cause SYNC to go "low," and the read (data in) sequence will be completed.

Further referring to the timing diagram of FIG. 11F, time durations disclosed therein are, in the preferred embodiment, as follows. Time duration $T_{1F}$ is preferably 54 nanoseconds maximum (in order to preclude a previous code (and thus, an erroneous code) from remaining in decoder 1316 of FIG. 11B for too long a time duration); $T_{2F}$ is preferably 60 nanoseconds; $T_{3F}$ is preferably 83 nanoseconds; and $T_{4F}$ is preferably one microsecond. Again, the above-stated time durations are preferable based on the previously described circuitry of FIGS. 11A–11D.

Interface 30 of FIG. 2—and the interrupt request procedure—will not be further described with reference to the logic block diagrams/circuit schematics of FIG. 11G and the timing diagram of FIG. 11H. Input SNDDAT is received by and sets flip-flop 1400 (the Data Ready flip-flop), while input DAL15 (the most significant bit from a control register to be described below) is received by and sets flip-flop 1402 (the Interrupt Enable flip-flop). The Q outputs of flip-flops 1400 and 1402 are provided to NAND gate 1404 (which performs an AND operation), and the output thereof is provided—via inverter 1406—as a clock input to set flip-flop 1408. The Q output of flip-flop 1408 is provided via inverter 1410 as output IRQ (see IRQ of the timing diagram of FIG. 11H). It is to be noted that flip-flop 1402 is clocked by STROB0 generated by the circuitry of FIG. 11D. IRQ is transmitted to the processor 34 as an "interrupt computer" command.

Figure 11G:
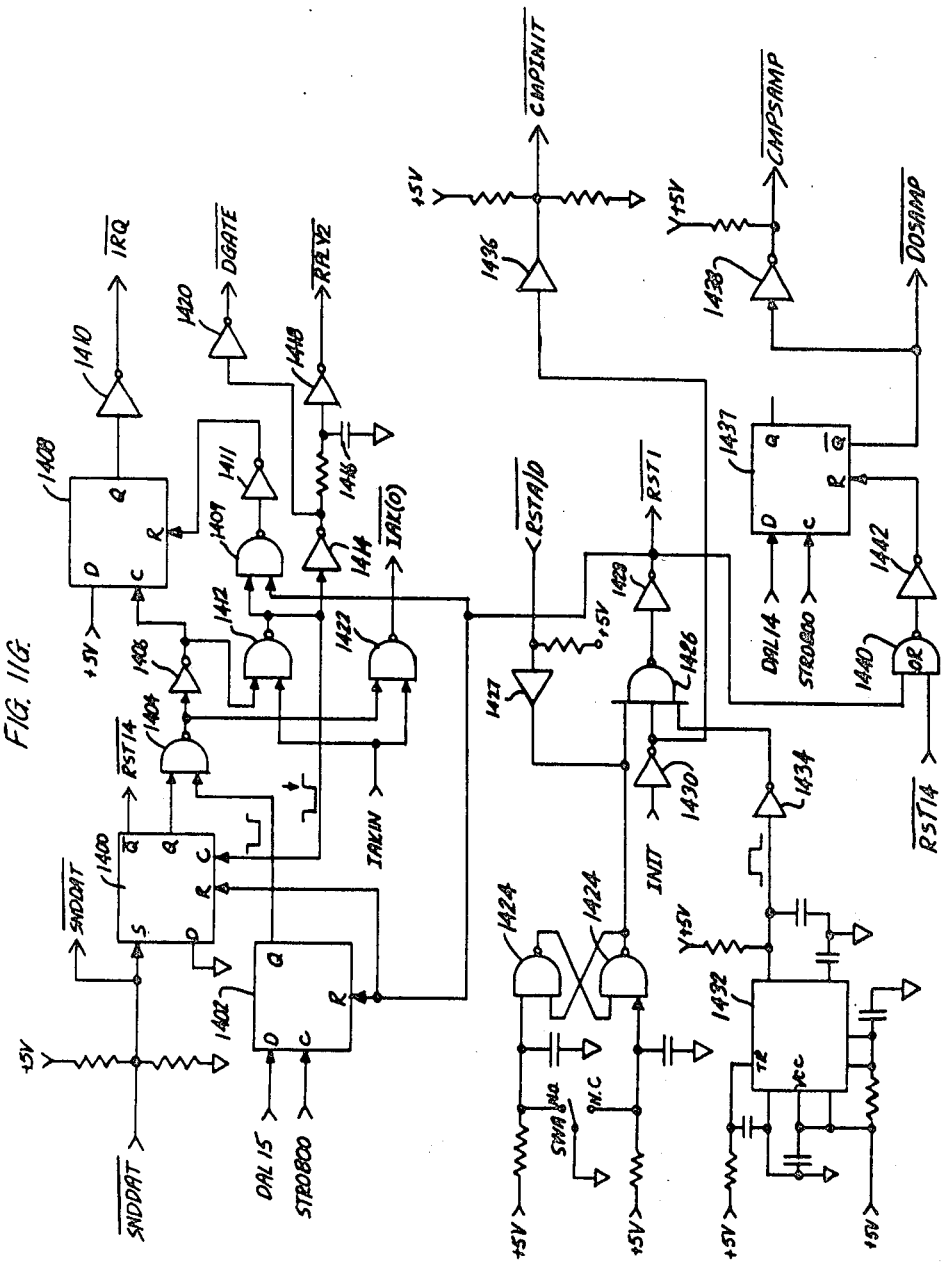

The circuitry of FIG. 11G receives input IAKIN which (as mentioned above) is generated by a bus transceiver device similar to devices 1240–1243 of FIG. 11B in response to computer-generated input IAKI received over the computer bus. Thus, further referring to FIGS. 11G and 11H, when both IAKIN and the output of inverter 1406 are "high," the output of NAND gate 1412 (GATVEC) goes "low." Output OVS,/GATVEC/ is provided, via inverter 1414 and RC delay network 1416, to inverter 1418, the output of which is RPLY2. Accordingly, RPLY2 goes "low" in response to GATVEC going "low." Moreover, GATVEC going "low" causes DGATE (the output of inverter 1420, the input of which is connected to inverter 1414) to also go "low." Finally, it is to be noted that flip-flop 1408 is reset in response to either GATVEC going "low" or RSTI going "low," such being accomplished via NAND gate 1409 and inverter 1411.

Referring back to FIG. 11D, it will be recalled that RPLY2 is OR'ed with the $\bar{Q}$ output of flip-flop 1338 in NAND gate 1340, with the result that the output RPLY goes "low" either in response to operator interrupt of the computer (RPLY2), or in response to DIN or DOUT in a Computer Read or Computer Write operation. Moreover, it will be further recalled that the output DGATE—in its "low" condition—provides an enabling input for bus transceivers 1240–1243, allowing the transceivers 1240–1243 to pass data DAT15, DAT14, . . . through to the computer bus (DAL15, DAL14, . . . ).

Returning to FIG. 11G, when IAKIN (an input from the computer via a bus transceiver device (not shown))—see the discussion of FIG. 11B above—goes "low" in response to RPLY2, output GATVEC of NAND gate 1412 goes "high," resulting in GATVEC going "low" (see FIG. 11H). Accordingly, outputs DGATE and RPLY2 also go "low." In addition, IAKIN is passed along to other devices on the computer bus by IAKO)/, which is generated by NAND gate 1422 in response to IAKIN when the CEOG system is not requesting an interrupt.

Resetting of the circuitry of FIG. 11G is accomplished in response to either of three conditions: operation of a manual switch SWA (preferably, physically located in the interface 30) so as to reset the no-bounce switch 1424, resulting in generation of output RSTI via NAND gate 1426 (which performs an OR operation) and inverter 1428; INIT going "high," as provided via inverter 1430 to NAND gate 1426; or turn-on of the system, activating a one second timer 1432 which provides an output via inverter 1434 to the NAND gate 1426 and inverter 1428. In the preferred embodiment, input RSTA/D is connected, via an amplifier 1427 and a wired-OR connection, to one input of NAND gate 1426 so as to cause RSTI to go "low" in response to RSTA/D going "low," thus achieving reset of the circuitry of FIG. 11G in response to resetting of the ADC circuitry in converter stage 56 (FIG. 2).

Returning to consideration of inverter 1430, which receives the input INIT, the output of inverter 1430 is connected to the input of amplifier 1436, the output of which produces CMPINIT (previously discussed above).

The circuitry of FIG. 11G further comprises a flip-flop 1437 which is clocked by input STROB0, and set by input DAL14—the fourteenth bit of a control word register (to be discussed below) in computer processor 34 of FIG. 2. As a result of being set, flip-flop 1437 generates a "low" output DOSAMP, which is bit 15 in a status word register (also to be discussed below). Correspondingly, output CMPSAMP from inverter 1438 goes "high." Finally, in response to reset via RSTI or RSTI4—as provided to NAND gate 1440—flip-flop 1437 is reset via inverter 1442, with the result that DOSAMP goes "high," while CMPSAMP goes "low."

The computer processor 34 of FIG. 2 will now be described. It will be recalled that the processor 34 operates in conjunction with computer programs (software) 36, display device 38, hard-copy printer 40, floppy disk 42, and keyboard (for user control) 44. Whereas any general-purpose digital computer having at least the aforementioned elements/capabilities can be utilized, the preferred embodiment of this invention includes a PDP 11/03 central processing unit as processor 34, a UT-52 terminal as display 38/keyboard 44, an RXV-11 disk unit as floppy disk 42, and the RT-11 software package as computer programs 36 (the latter being readily available from Digital Equipment Corporation). In addition, the circuitry of FIGS. 11A–11G constitutes an addition to the memory locations of the computer. A summary of the additions is shown in Table 2 (below).

TABLE 2

| EOG I/O ADDRESSES | | |
|---|---|---|
| Register | Address | Read/Write |
| Control Word Register | 164,000 | Write Only |
| Status Word Register | 164,002 | Read Only |
| Data In Ch 1 | 164,020 | Data CH 1 |
| 2 | 22 | Data CH 2 |
| 3 | 24 | Data CH 3 |
| 4 | 26 | Data CH 4 |
| 5 | 30 | Data CH 5 |
| 6 | 32 | Data CH 6 |
| 7 | 34 | Chair Speed |
| 8 | 36 | Strip Cage Speed |
| Data out Ch 1-8 | 164,040 thru 164,056 | Write Only |
| Move X | 164,060 | Write Only |
| Position X | 164,062 | Read Only |
| Move Y | 164,070 | Write Only |
| Position Y | 164,072 | Read Only |
| Chair Control | 164,004 | Write Only |
| Interrupt Location | 000,154 | For Data |
|  | 000,160 | For Zero Adj. |

The control word register (mentioned in Table 2) is a 16-bit, write-only register, organized from bit 15 through bit 0, as follows:

Bit 15: Interrupt Enable bit—this bit will be reset whenever the logic section 62 (FIGS. 10A–10O) or the computer processor 34 (FIG. 2) initializes the system. Otherwise, it is set/reset by the computer programs (software) 36. This bit is actually generated—in the preferred embodiment—by flip-flop 1402 in FIG. 11G.

Bit 14: A "single step" bit provided to the ADC in converter 56 (FIG. 2). This bit is generated—in the preferred embodiment—by flip-flop 1437 and results in generation of signal CMPSAMP (via data bit DAL14 of FIG. 11G), which is one of the signals which generates SAMPLE (see FIG. 6D), the latter being utilized (it will be recalled) in the analog-to-digital conversion process (FIG. 6A).

Bit 13: A Go bit, which is provided (at input DOUT13) to the arrangement of FIG. 10J so as to cause generation of signal 5MSSAMP, calls for the generation of data at the rate of one sample point (six channels) every 5 milliseconds. It will be recalled that DOUT13 turns on flip-flop 970, triggering one-shot 978, so as to generate 5MSSAMP.

Bit 12: A Flash bit is provided, as input DOUT12 (CMPSHTR), to flip-flop 1022 of FIG. 10L, so as to generate output SHUT, resulting in pulsing of the flasher 70.

Bit 11: A 2.5 Millisecond Sample bit is provided as input DOUT11 to flip-flop 972 of FIG. 10J. Flip-flop 972 accordingly—via its Q output—enables relay (solenoid/switch) 982, so as to adjust the timing of one-shot 980. As a result, the sampling time is decreased from 5 milliseconds to 2.5 milliseconds.

Bit 10: A bit DOUT10 is provided to flip-flop 1020 of FIG. 10L, to set that flip-flop. As a result, flip-flop 1020—via its Q output—generates output $\overline{\text{RECORDING}}$. When $\overline{\text{RECORDING}}$ goes "low," display indicator DS9 of FIGS. 9A and 9B is illuminated thus indicating that the system is in the "recording" mode of operation.

Bit 9: A Copy bit, which causes the hard-copy printer 40 (FIG. 2) to make a printout of test results.

Bits 8–0: Bits 5–8 are "spare" bits available for use in accomplishing other functions or display indications, as would be judged by one of ordinary skill in the art to be necessary with respect to the CEOG system. Furthermore, bits 0–4—it will be noted—are stored in latch circuit 1254 of FIG. 11C as written thereinto by STROB0. Thus, these bits may be read back by the computer processor 34 through tristate buffer 1253, as enabled by $\overline{\text{STROB1}}$. This affords the user of the CEOG system with an advantageous test capability for testing the timing in interface 30 (FIG. 2), and as well with a test capability for error-testing of data passing through the computer bus via the interface 30.

The status word register is a 16-bit, read-only register, organized from bit 15 through bit 0, as follows:

Bit 15: A Write Busy bit, which must be checked before the computer writes a word into any of the registers (except for the control register). If bit 15 is "on," this indicates that the CEOG system is involved in storing a word transmitted by the computer processor 34 (FIG. 2) during the last "write" command. In the preferred embodiment, bit 15 is provided by flip-flop 1437 of FIG. 11G. It is to be noted that output $\overline{\text{DO SAMP}}$ of flip-flop 1437 becomes computer input DAT15 via tristate buffer 1253 of FIG. 11C.

Bit 14: A Stripe-On bit indicating that the stripe cage 76 in optokinetic device 16 is turning. This bit is generated by switch S11 (FIGS. 9A and 9C)—when turned on by the operator—and is provided to the computer processor 34—via NAND gate 912, inverter 918, NAND gate 924 and inverter 928 of portion L4 of FIG. 10H—as input DATIN14.

Bit 13: A Stripe Right bit, indicating that the stripe cage 76 is rotating rightward (bit 13=1) or leftward (bit 13=0).

Bit 12: A Copy Busy bit, indicating that the hard-copy printer 40 (FIG. 1) is busy printing from the last command.

Bits 11–0: These bits are indicated as spare bits, but can be utilized for providing various other control functions/display indicators as would be obvious to one of ordinary skill in the art.

The Data-In registers are made up of the above-specified (Table 2) I/O addresses, which correspond to respective channels 1–8 of information. As will be recalled from the discussion of the ADC circuitry (FIG. 6A), digital channel 1 (responding to analog input AMPOUT1) contains left vertical eye movement test data, channel 2 contains right vertical eye movement test data, channel 3 contains left horizontal eye movement test data, channel 4 contains right horizontal eye movement test data, channels 5 and 6 contain VER test data, channel 7 (corresponding to analog input TACH2) contains chair speed data, and channel 8 (corresponding to analog input STRIPESPD) contains cage speed test data.

Data Out channels 1-8 (referred to in Table 2 above) include digital data from the computer processor 34 of FIG. 2 for conversion in converter stage 56. Specifically, channels 1-4 of the Data Out channels comprise digital data for deriving analog signals BIASN (N=1, 2, ..., 6)—see FIG. 6E—for use in developing zero-adjustment signals ZRADJ (J=1, 2, ..., 6). Discussion of channels 5-8 is eliminated as not being critical to the full disclosure of this invention; however, it will be obvious to one of ordinary skill in the art that channels 5-8 could be utilized for the development of various other analog functions.

The Move X register (referred to in Table 2) is a 16-bit, write-only register, organized (in the preferred embodiment) as follows:

Bit 10: Go X mirror—instructs the mirrors 14 (and associated driving circuitry) to begin scanning in the X direction with its own sine wave. See input DOUT10 to flip-flop 1020 in FIG. 10L, resulting in generation of XSINE.

Bit 11: The CMPSINE bit which instructs the mirrors 14 that the computer processor 34 is to control the X deflection of the mirrors 14 so that the 10 least significant bits of the MOVX register are in control of operation of the X-deflection mirrors. See input DOUT11 (CMPSINE) to flip-flop 1021 in FIG. 10L, and resultant generation of CMPSINE by inverter 1034.

Bit 12: The CMPSHTR bit which opens the shutter 66 (FIG. 2) to allow the light from laser 12 to pass therethrough, usually used in conjunction with bits 10 or 11 above. See input DOUT12 (CMPSHTR) applied to flip-flop 1022 in FIG. 10L, with resultant generation of SHUT by NPN transistor 1036.

Bit 13: YSCAN bit which causes the Y-deflection mirrors to scan—similar to Bit 10 except that it controls scanning in the Y direction. See input YSCAN to amplifier 1110 in FIG. 10M, with subsequent generation of mirror driving output YDRIVE.

It is to be noted that, in the preferred embodiment, when Bits 10 and 13 are simultaneously on, mirror scanning in a 45 degree direction (that is, along a line with a slope of one) can be achieved.

Bits 0-9: These 10 bits are provided by the processor 34—via interface 30—to converter stage 56 (FIG. 2). Specifically, in the preferred embodiment, bits 0-9 are provided as inputs DTOA0-DTOA9 to circuitry of the type illustrated as DAC circuitry 300 of FIG. 6E, the data being strobed into latch circuits 302 and 303 by a strobe input STROBMX (similar to STROBN). Therein, the digital data is digital-to-analog converted to develop analog output MOVX (similar to BIASN of FIG. 6E), thus providing an analog voltage (preferably, having a value of from −5 volts (000 ... 000) to +5 volts (111 ... 111)) defining desired movement of the X mirrors of mirrors 14 (FIG. 2).

Position X register (referred to in Table 2) is a read-only register which feeds back (to the computer processor 34 of FIG. 2) information relative to the position of the X-scanning mirrors 14. The 10 least significant bits of this register give the relative X position of the mirrors. However, in the preferrred embodiment, either the Go bit or the single-step bit (both of which were referred to above) must be turned on, and an interrupt received, before the 10 least significant bits of the Position X register contain up-to-date data. (This is true of all the outputs of A/D converters 56' of FIG. 6A). The Move Y register is a write-only register used for controlling scanning of the mirrors 14 in the Y direction. The 10 least significant bits (0-9) of this register are D/A converted—in the same manner as described above for bits 0-10 controlling X direction scanning—to form MOVY, an analog voltage which operates in conjunction with the Y position potentiometer (under the control of the operator)—see FIGS. 9A-9E—to move the Y-deflection mirrors. See potentiometer 504 in circuit 502 of FIG. 9C.

Position Y register is a read-only register, the 10 least significant bits of which give the relative Y position of the mirrors 14. As was the case with the Position X register, either the Go bit or the single-step bit must be on, and an interrupt received, before the 10 least significant bits of the Position Y register have up-to-date data contained therein.

Finally, with reference to the above discussion, the CEOG system address decoding scheme is set forth in Table 3 (below). It is to be noted that, in the preferred embodiment, memory locations 164,000 through 164,176 are not true memory locations in processor 34 (FIG. 2). Rather, locations 164,000-164,016 include the control word register, status word register, and chair control register, and addressing of these locations is accomplished by the decoding NAND gate 1274, decoders 1316, 1318, etc. of FIG. 11D (previously described) which produce STROB0, STROB1, etc. to send data to the proper address.

In a similar manner, locations 164,020-164,036 are channels 1-8 of data input from the CEOG system to the processor 34, such data input being, of course, analog-to-digital converted prior to input. Locations 164,040-164,056 are channels 1-8 of data output from the processor 34 to the CEOG system, such data output being, of course, digital-to-analog converted after output.

TABLE 3

EOG ADDRESS DECODING

| Address | D6 | D5 | D4 | D3 | D2 | D1 | D0 | Octal Decoding | |
|---------|----|----|----|----|----|----|----|----------------|--|
| 164,000 | 0 | 0 | 0 | 0 | 0 | 0 | 0 | STROB0 | Control out |
| 002 | 0 | 0 | 0 | 0 | 0 | 1 | 0 | 1 | status in |
| 004 | 0 | 0 | 0 | 0 | 1 | 0 | 0 | 2 | chair |
| 006 | 0 | 0 | 0 | 0 | 1 | 1 | 0 | 3 | |
| 010 | 0 | 0 | 0 | 1 | 0 | 0 | 0 | 4 | |
| 12 | | | | 1 | 0 | 1 | 0 | 5 | |
| 14 | | | | 1 | 1 | 0 | 0 | 6 | |
| 16 | | | | 1 | 1 | 1 | 0 | 7 | |
| 20 | 0 | 0 | 1 | 0 | 0 | 0 | 0 | STROB10 | (A/D) Data |
| 22 | | | 1 | 0 | 0 | 1 | 0 | 11 | in ch. 1 |
| 24 | | | 1 | 0 | 1 | 0 | 0 | 12 | thru 8 |
| 26 | | | 1 | 0 | 1 | 1 | 0 | 13 | |
| 30 | | | 1 | 1 | 0 | 0 | 0 | 14 | |
| 32 | | | 1 | 1 | 0 | 1 | 0 | 15 | |
| 34 | | | 1 | 1 | 1 | 0 | 0 | 16 | |
| 36 | | | 1 | 1 | 1 | 1 | 0 | 17 | |
| 40 | 0 | 1 | 0 | 0 | 0 | 0 | 0 | STROB20 | (D/A) Data |
| 42 | | 1 | 0 | 0 | 0 | 1 | 0 | 21 | out ch. 1 |
| 44 | | 1 | 0 | 0 | 1 | 0 | 0 | 22 | thru 8 |
| 46 | | 1 | 0 | 0 | 1 | 1 | 0 | 23 | |
| 50 | | 1 | 0 | 1 | 0 | 0 | 0 | 24 | |
| 52 | | 1 | 0 | 1 | 0 | 1 | 0 | 25 | |
| 54 | | 1 | 0 | 1 | 1 | 0 | 0 | 26 | |
| 56 | | 1 | 0 | 1 | 1 | 1 | 0 | 27 | |
| 60 | | 1 | 1 | 0 | 0 | 0 | 0 | STROB30 | Move x (to) |
| 62 | | 1 | 1 | 0 | 0 | 1 | 0 | 31 | position x |
| 64 | | 1 | 1 | 0 | 1 | 0 | 0 | 32 | I/P |

TABLE 3-continued

EOG ADDRESS DECODING

| Address | Bits | | | | | | | Octal Decoding |
|---|---|---|---|---|---|---|---|---|
| | $D_6$ | $D_5$ | $D_4$ | $D_3$ | $D_2$ | $D_1$ | $D_0$ | |
| 66 | 1 | 1 | 0 | 1 | 1 | 0 | | 33 move y (to) |
| 70 | 1 | 1 | 1 | 0 | 0 | 0 | | 34 position y |
| 72 | 1 | 1 | 1 | 0 | 1 | 0 | | 35 |
| 74 | 1 | 1 | 1 | 1 | 0 | 0 | | 36 |
| 76 | 1 | 1 | 1 | 1 | 1 | 0 | | 37 |

Finally, locations 164,060–164,076 are the Move X register, Position X register, Move Y register, and Position Y register (previously discussed above).

Thus, in the preferred embodiment, much of the circuitry described in FIGS. 11A through 11G above act as, or perform the functions of, locations 164,000–164,076. Thus, a "1" deposited in bit 12 of address 164,000 will cause the flasher 70 (FIG. 2) to flash. This bit will be reset after the flash occurs (as previously described above).

Referring to Table 3, address data bits D6–D0 represent the seven least significant bits of a data address for addressing any one of the locations 164,000–164,076. It is to be noted that since, in the preferred embodiment, only alternate locations (164,000; 164,002; etc.) are utilized, bit D0 can be dropped in terms of the octal decoding of bits D6–D0. Thus, bits D6–D1 correspond to address line inputs DAL6–DAL1 provided as data address line inputs DAL6–DAL1 provided by the computer bus to bus transceiver devices 1240–1243 of FIG. 11B (discussed above), and further correspond to inputs ADDR6–ADDR1 provided to decoders 1316 and 1381 of FIG. 11B (also discussed above). As a result of octal decoding (in decoders such as previously mentioned), various groups of strobe signals GRP0STB, GRP1STB, GRP2STB and GRP3STB (as shown in Table 3) are developed—specifically, STROB0–STROB7, STROB10–STROB17, STROB20–STROB27 and STROB30–STROB37.

As mentioned earlier, the CEOG system of FIG. 2 includes a processor 34 which is preferably software-controlled by computer programs 36. As also mentioned earlier, computer programs 36 preferably use the RT-11 software package (provided by Digital Equipment Corporation for use with the preferred processor unit PDP11/03).

Figure 12A:
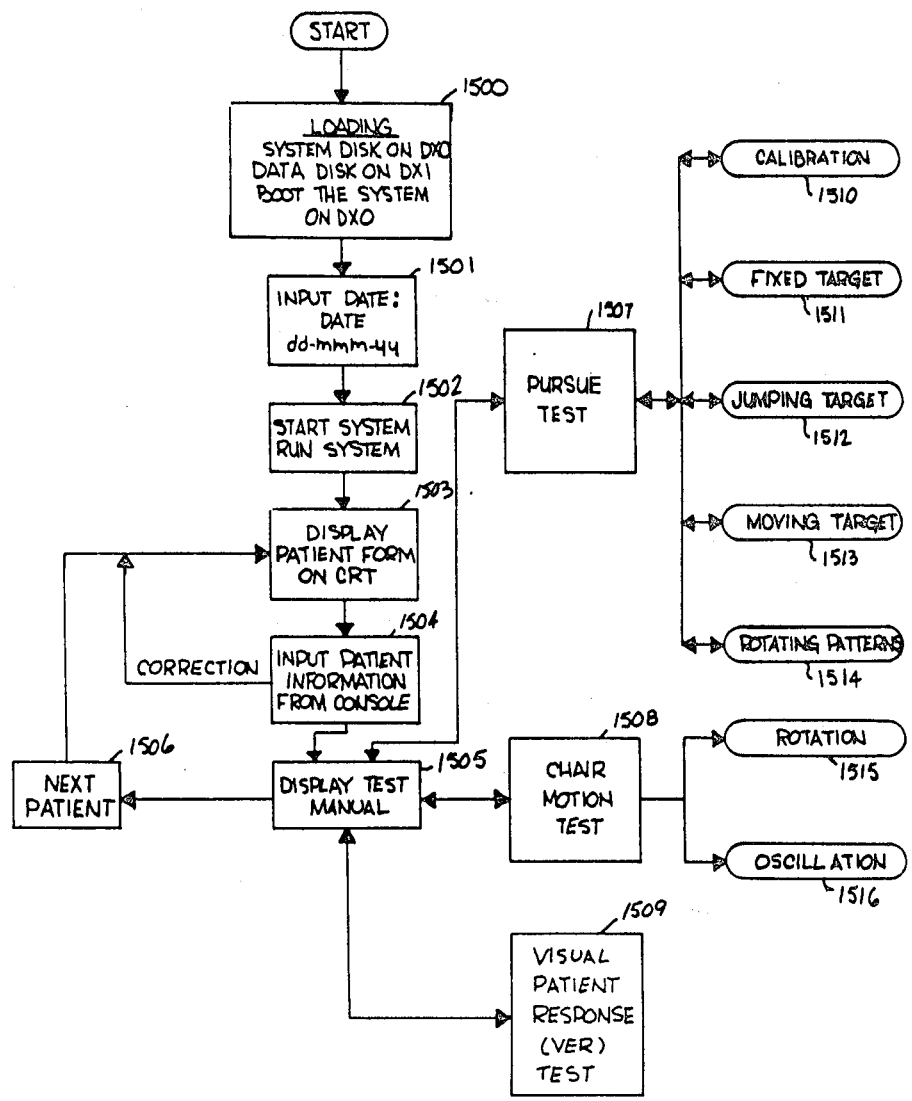
FIGS. 12A and 12B are general flowcharts of the test program and analysis program, repectively, implemented by the processor 34 of the CEOG system of FIG. 2.
Figure 12B:
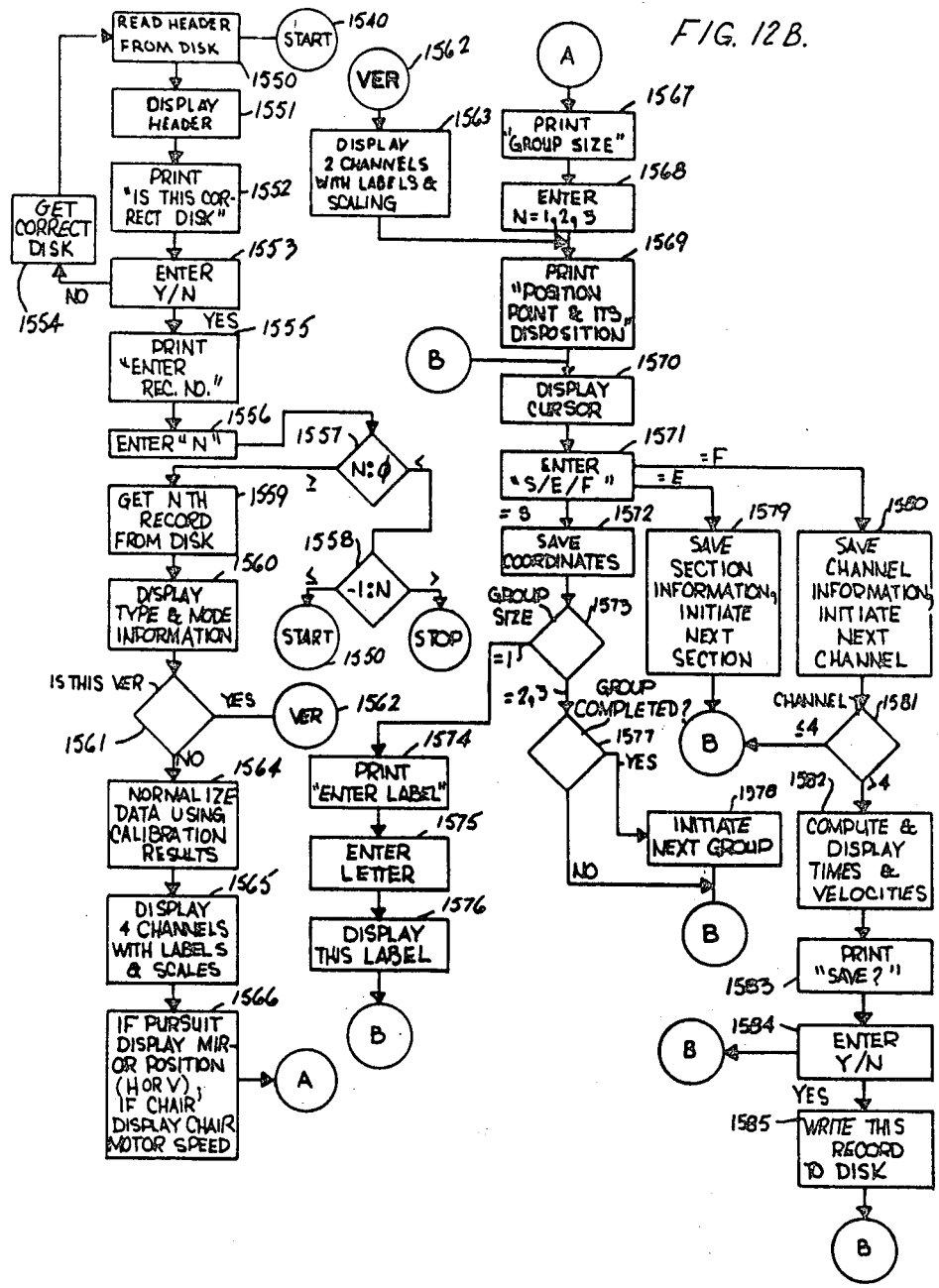

FIGS. 12A and 12B are general flowcharts of the test program and analysis program, respectively, implemented by the processor 34 of the CEOG system of FIG. 2, as a preferred implementation of computer programs 36. That is, computer programs 36 of FIG. 2 are divided into a Run program (FIG. 12A) by means of which various selected tests are performed on the patient, and an Analysis program (FIG. 12B) by means of which the test results are analyzed/processed and a display or hard copy of the test results in a convenient format is provided to the test administrator.

Prior to discussion of FIGS. 12A and 12B, a few additional introductory comments are appropriate. In the preferred embodiment of the CEOG system of the present invention, there are three processes: test, analysis and review. Specifically, RUN TEST calls up the test process for presenting the stimulus to the patient and recording the patient's reaction; RUN ANALYSIS calls up the analysis process, by which the patient's reaction is analyzed and recorded on the patient's record; and RUN REVIEW calls up the review process, by which the patient's record is reviewed, a directory of patients processed can be displayed, and a hard copy replication of the patient's records can be made. As would be obvious to one of ordinary skill in the art, the processor 34 is preferably programmed to provide the operator (test administrator) with the capacity of choosing which of the three processes (test, analysis or review) to enter by means of entry of an appropriate alphabetical character (e.g., T, A or R) on the keyboard 44 (FIG. 2).

Referring to FIG. 12A, presuming that the test process has been selected, such test process will be commenced by loading the system and data disks, and "booting" the system—block 1500 of FIG. 12A. The present data (such as the present date) is then entered into the computer's file record—block 1501. The test process is formally commenced by starting the system (e.g., by typing .RUN SYS on the keyboard 44 of FIG. 2)—block 1502. A display of a patient data form on display device 38 (FIG. 2) will then occur—block 1503. The test administrator then enters various patient information (such as name, ID, etc.) onto the data form from the keyboard 44—block 1504.

Upon completion of patient data input, the system displays a test menu—block 1505—such as the following:

P = pursuit test
C = chair motion test
V = visual evoked response (VER) test
R = return to the CEOG system Upon selection of the pursuit test—block 1507—a pursuit test menu is then presented, as follows:

C = calibration
F = fixed target
J = jumping target
M = moving target
R = rotating patterns
S = recall test type menu Presuming selection of the calibration procedure—block 1510—the test administrator then commences a calibration procedure. Such calibration procedure is predetermined in accordance with the particular calibration regimen dictated by the programming of the processor 34 via computer programs 36. For example, in the preferred embodiment, such calibration procedure is as follows:

1. Perform auto-zero adjustment; type C when completed.
2. Calibration continued—perform horizontal 15° left calibration; type C when completed.
3. Calibration continued—perform auto-zero; type C when completed.
4. Calibration completed—perform horizontal 15° right calibration; type C when completed.
5. Calibration continued—perform auto-zero; type C when completed.
6. Calibration continued—perform vertical 8° up calibration; type C when completed.
7. Calibration continued—perform auto-zero; type C when completed.
8. Calibration continued—perform vertical 8° down calibration; type C when completed.
9. Calibration completed—computer returns to pursuit menu.

Presuming that the test administrator chooses the fixed target test—block 1511—the fixed target test will be administered under control of the processor 34 and computer programs 36. In the preferred embodiment, instructions for administration of the fixed target test are as follows:

E = recall pursuit menu.

To record test results, push Space Bar to start, push again to stop.

T = time scale—follow with 5, 7.5, 10, 12.5, 15, 17.5 or 20 seconds—otherwise time scale is 2.5 seconds.

A = auto-zero; push C when completed.

O = eyes open; push carriage return to stop.

C = eyes closed; push carriage return to stop.

Presuming operator selection of the jumping target test—block 1512—the preferred procedure is as follows:

E = recall pursuit menu.

To record, push Space Bar to start, push again to stop.

T = time scale: follow with 5, 7.5, 10, 12.5, 15, 17.5 or 20 seconds; otherwise, time scale is 2.5 seconds.

A = auto-zero; push C when completed.

H = horizontal; push carriage return to stop.

V = vertical; push carriage return to stop.

FH = 50 spots horizontal.

FV = 50 spots vertical.

Presuming selection of the moving target test—block 1513—the preferred test procedure is as follows:

E = recall pursuit menu.

To record, push Space Bar to start, push again to stop.

T = time scale: follow with 5, 7.5, 10, 12.5, 15, 17.5 or 20 seconds; otherwise, time scale is 2.5 seconds.

To choose period, turn potentiometer adjustment knob (horizontal speed adjustment knob P3 to FIG. 9A).

Choose test: push carriage return to stop.

A = auto-zero; push C when completed.

HT = horizontal, triangle.

HS = horizontal, sine.

VT = vertical, triangle.

VS = vertical, sine.

Presuming selection of the rotating patterns test—block 1514—the preferred procedure is as follows:

E = recall pursuit menu.

To record: push Space Bar to start, push again to stop.

T = time scale: follow with 5, 7.5, 10, 12.5, 15, 17.5 or 20 seconds; otherwise, time scale is 2.5 seconds.

Lower rotating drum (by operator control section 450 of FIG. 9A).

To choose rotation speed, turn potentiometer adjustment knob (P2 in FIG. 9A).

P = perform rotating pattern test, to stop push carriage return.

TP = perform three revolutions of the drum for the pattern test.

If the test administrator chooses the chair motion test—block 1508—either rotation of the chair (block 1515) or oscillation of the chair (1516) can be selected. The preferred procedure is as follows:

C = calibration.

R = rotate chair right or left.

C = oscillate chair four cycles.

F = rotate chair with fixation light.

S = recall test type menu.

For rotation of the chair—block 1515—the procedure is preferably as follows:

E = recall chair motion menu.

To record: push Space Bar to start, push again to stop.

T = time scale: follow with 5, 7.5, 10, 12.5, 15, 17.5 or 20 seconds; otherwise, time scale is 2.5 seconds.

Set rotation speed selection knob (potentiometer adjustment knob P1 of FIG. 9A).

To set number of rotations, type N followed by any number from 1 through 14.

A = auto-zero; push C when completed.

R = rotate chair right: take horizontal data at end.

L = rotate chair left: take horizontal data at end.

RHV = rotate chair right: take horizontal and vertical data at end.

LHV = rotate chair left: take horizontal and vertical data at end.

It is to be noted, that, in the chair rotation test, data may be taken during rotation and also after the chair has stopped.

Presuming that oscillation—block 1516—has been chosen, the chair will be automatically oscillated for four cycles, and data will be taken during chair motion. The procedure is preferably as follows:

E = recall chair motion menu.

To record: push Space Bar to start, push again to stop.

T = time scale: follow with 5, 7.5, 10, 12.5, 15, 17.5 or 20 seconds; otherwise, time scale is 2.5 seconds.

Set rotation speed selector knob to "oscillate" position.

A = auto-zero; push C when completed.

T = perform test.

As indicated above, during the rotation test —block 1515—the operator can designate rotation with use of a fixation light, with data being derived during chair rotation. The preferable procedure is the same as stated with respect to oscillation of the chair (immediately above), with one exception: change "Set rotation speed selector knob to 'oscillate' position" to the following:

Position fixation light (via switches S9 and S10 of FIG. 9A) and turn the light on.

Set rotation speed selector knob to "fixation light" position.

Presuming selection of the visual evoked response (VER) test—block 1509—the preferable procedure is as follows:

Blinking letter (on display 38 of FIG. 2) indicates next test to be done in the normal VER sequence.

B8 = both eyes open, 128 flashes, one per second.

B4 = both eyes open, 64 flashes, one per second.

R4 = right eye occluded, 64 flashes, one per second.

L4 = left eye occluded, 64 flashes, one per second.

T(f,r) = test VER using number of flashes f (f is 16, 32, 64 or 128) and flashes per second r (r is ½, 1 or 2).

M(m) = on display, choose magnification factor m.

REC = record the display.

S = recall test type menu.

To summarize the above, it is to be noted that in each instance, the particular test or group of tests selected by the test administrator is automatically administered to the patient under control of the processor 34/software 36 of FIG. 2. Specifically, whereas manual or semi-automatic systems of the prior art called for the test administrator to manipulate the various test devices in accordance with a prescribed procedure for each test (typically, as set forth in a bulky and inconvenient instruction manual), the system of the present invention provides for truly automated test administration, in that the above-listed instructions (for each test) are sequentially displayed on display device 38 (FIG. 2). A bare minimum of information is then required from the test administrator, and such information is entered by the administrator utilizing the keyboard 44. Moreover, in the case where the test administrator is required by the test program to provide parameters (such as chair rotation speed via potentiometer adjustment knob P1 of FIG. 9A, etc.) such information can be very quickly and efficiently set by utilization of the integrated operator control section 450 illustrated in FIG. 9A.

By virtue of this automated test administration utilizing an integrated CEOG system, the administration of pursuit tests, chair motion tests and visual evoked response (VER) tests—which previously were relatively inefficient in their administration—can be very quickly and efficiently performed. The end result is, of course, that a larger number of patients can be treated by utilization of the integrated CEOG system of the present invention. Moreover, the integrated CEOG system of the present invention is highly flexible in that, as previously discussed and described in great detail above, the test administrator always has the option of manually administering one or more of the particular tests by manipulation of the various controls in operator control section 450 of FIG. 9A.

Finally, in either mode of operation—automated or manual test administration—immediate display of the test results, in a graphical format readily usable by the attending test administrator or physician, is provided (as illustrated on display device 38 of FIG. 1). By providing the test administrator or attending physician with immediate display of useful test results, the administrator or physician is able to: (1) determine immediately if the test has been properly administered, (2) determine whether or not the patient has validly received/reacted to the test stimuli presented, and (3) thus, determine whether further testing (or repeated testing) is necessary.

The analysis program of the software 36 of FIG. 1 will now be described with reference to FIG. 12B. Upon commencement of the analysis program (see START block 1540), the following steps are taken:

Header information is read from the disk 42 (FIG. 1)—block 1550.

Header information is displayed—block 1551.

A message "Is this the correct disk?" is printed out—block 1552.

Operator enters a Y (for "yes") or N (for "no")—block 1553.

If "no," the system obtains the correct disk—block 1554—and returns to block 1550.

If "yes," the system prints the message "enter record number"—block 1555.

The operator enters the record number "N"—block 1556.

N is compared to zero (block 1557); then, if N is equal to or greater than zero, the Nth record is obtained from the disk (block 1559), while if N is less than zero, a further decision (block 1558) is made. Specifically, if −1 is equal to or less than N, the system returns to START (block 1550), while if −1 is greater than N, the system stops.

Once the Nth record from disk is obtained (block 1559), the system displays the type and mode information—block 1560.

Decision as to whether or not a VER test has been performed is made—block 1561.

If VER—block 1562—the system displays two channels with labels and scaling—block 1563—and enters a "print" routine (to be subsequently discussed).

If not VER, data is normalized using calibration results—block 1564.

Four channels with labels and scales are then displayed—block 1565.

Then, if the test is a pursuit test, mirror position (H or V) is displayed, while if chair rotation is called for, chair motor speed is displayed—block 1566—and the "print" routine is entered.

In the print routine, the following procedure applies:

The "group size" is printed—block 1567.

The operator then enters N=1, 2, 3 as the group size—block 1558.

At this point, the print routine would be entered if the test question was a VER test (see discussion above).

The system prints the message "position point and its disposition"—block 1569.

The system displays a cursor—block 1570.

The operator enters one of three alphabetic characters: S, E or F—block 1571.

If S is entered, the coordinates (previously entered) are saved—block 1572.

Then, a determination as to group size is made—block 1573.

If group size equals 1, the system prints the message "enter label" (block 1574), the operator enters a character (block 1575), the system displays the label so entered (block 1576), and the system returns to "display cursor" (block 1570).

If the group size is 2 or 3 (block 1573), a decision as to whether or not the group is completed is made—block 1577.

If the group is completed, the next group is initiated (block 1577), and then a return to "display cursor" (block 1570) is executed.

If the group is not completed, a return to "display cursor" (block 1570) is immediately executed.

If the operator enters E (in block 1571), section information is saved, and initiate next section is executed—block 1579—the system returning to "display cursor" (block 1570).

If the operator enters F (in block 1571), the channel information is saved, and initiate next channel is executed—block 1580—followed by a decision (block 1581) as to whether the channel is less than, equal to or greater than 4.

If the channel is equal to or less than 4, a return to "display cursor" (block 1570) is executed.

On the other hand, if the channel is greater than 4, the system computes and displays times and velocities (block 1582), and prints the message "save?" (block 1583).

Then, the operator enters Y ("yes") or N ("no")—block 1584.

If "no," the system returns to "display cursor" (block 1570), while if "yes," the system writes this record to disk (block 1585), and then returns to "display cursor" (block 1570).

The Test program of FIG. 12A and Analysis program of FIG. 12B are implemented by various computer programs 36 (FIG. 1)—preferably, a master control program, individual test programs for the respective EOG and VER tests, and individual main analysis programs for the respective EOG and VER tests.

More specifically, the computer programs 36 of FIG. 1 are implemented, in the preferred embodiment, by the following:

a master control and stored format (for printout) program;
a program for calling forms for display;
an EOG test program;
a VER test program;
a main analysis program (for EOG test analysis);
a main analysis program (for VER test analysis); and
a display program.

The CEOG system of FIG. 2, and more particularly the "feedback control of test stimuli" feature thereof will now be described with reference to FIGS. 14A and 14B which are diagrams of portions of the control panel 54 of the system of FIG. 2, as modified for feedback control of test stimuli, and with reference to FIGS. 13A and 13B which are flowcharts of the feedback control program implemented by the processor 34 of the CEOG system of FIG. 2.

As indicated earlier, the system of the present invention is especially flexible and adaptable so as to provide automatic feedback control of test stimuli in response to the processing and analysis of electrode test data derived from the patient. In the past, various experiments relating to variable feedback testing and the development of control theory models for eye tracking movements have been performed and documented. For example, see the following: "Variable Feedback Experiments Testing A Sampled Data Model For Eye Tracking Movements", by Young et al, *IEEE Transactions on Human Factors in Electronics* (September 1963), pp. 38-51; *Neurological Control Systems—Studies in Bioengineering*, by Stark, New York: Plenum Press (1968), Chapter 3, pp. 271-295; "The Mechanics of Human Smooth Pursuit Eye Movement", by D. A. Robinson, *J. Physiol.*, Volume 180, pp. 569-591 (1965); "Saccadic and Smooth Pursuit Eye Movements in the Monkey", by A. F. Fuchs, *J. Physiol,* Volume 191, pp. 509-631 (1967); "Adaptive Properties of the Eye-Tracking System as Revealed by Moving-Head and Open-Loop Studies", by Fleming et al, *Annals New York Academy of Sciences*, pp. 825-850 (1969); "Ocular Stability in Variable Visual Feedback Conditions in the Rabbit", by Collewijn et al, *Brain Research,* Volume 36, pp. 47-57 (1972). However, the subject matter disclosed in the latter articles relates to experimental arrangements of the analog type developed for the purpose of elucidating the structure of the ocular motor system. That is to say, the latter articles do not present a high-speed digital system which not only administers tests to a patient, but also processes test results and, based on the latter analysis, adjusts the test stimuli in accordance with the processed test results.

Thus, the present invention is provided with a capability, implemented by the processor 34 (FIGS. 1 and 2), by means of which feedback control of the test stimuli is achieved. Specifically, the processor 34 contains a feedback control of test "stimuli" program or group of programs 1517 (FIG. 12A) which, together with certain modifications to the hardware of the system described above, achieves this capability.

Figure 13A:
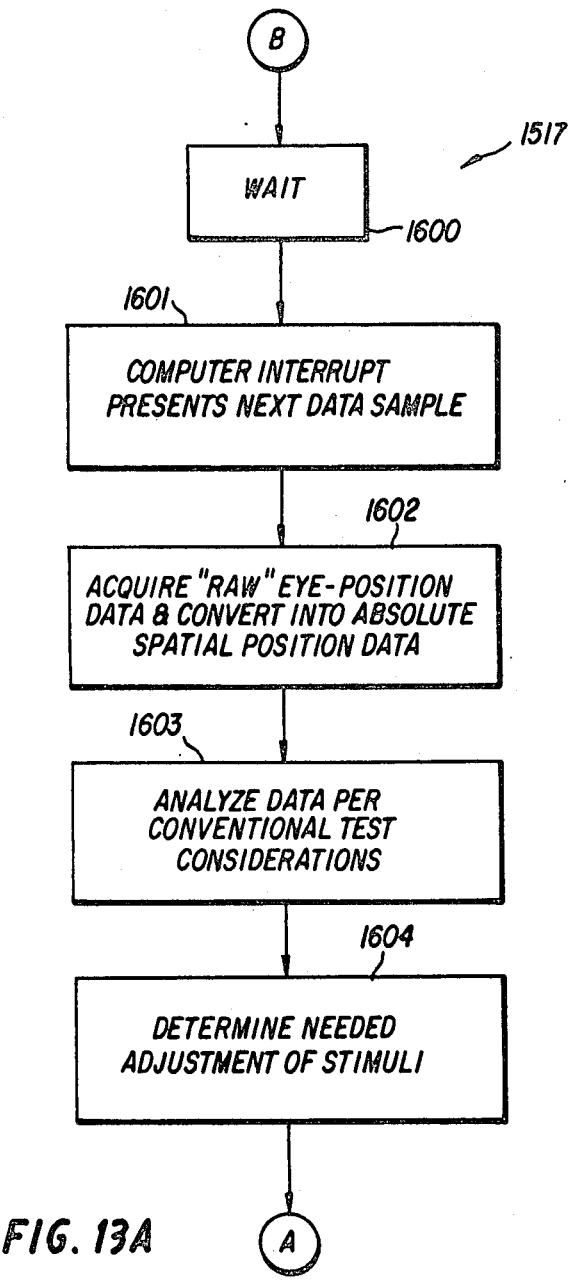
FIGS. 13A and 13B are flowcharts of the feedback control program implemented by the processor 34 of the CEOG system of FIG. 2.
Figure 13B:
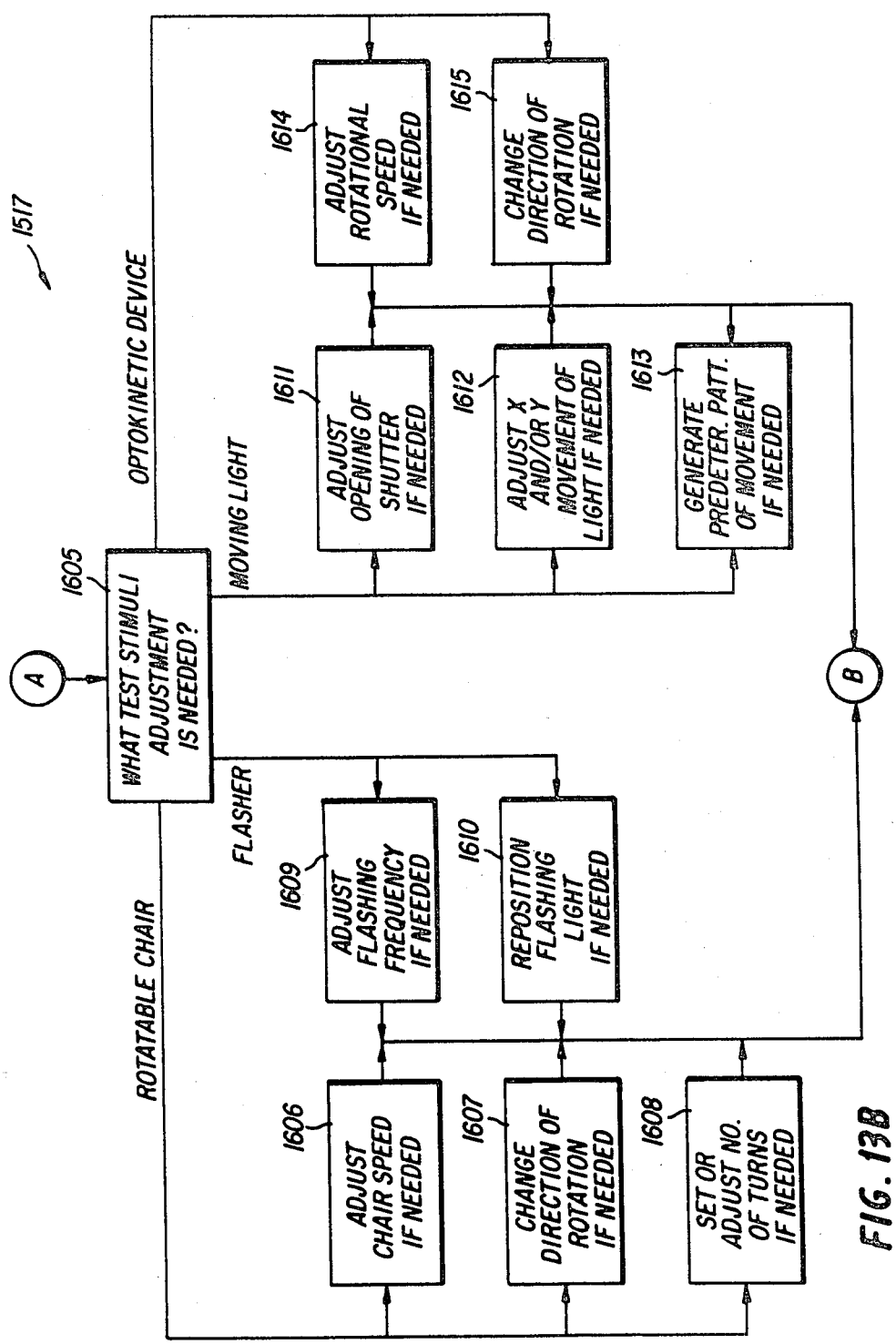

Referring to FIG. 13A, the program 1517 is disclosed in more detail in the form of a flowchart of the operations performed thereby. After a waiting period (block 1600), during which the processor 34 awaits new test data via preamp network 34, filters/amplifiers 26, digitizer 28, and computer interface 30 (FIG. 1), a computer interrupt is generated, indicating the presentation of a next data sample (block 1601). In this manner, the processor 34 acquires the "raw" eye-position data and converts it into absolute spatial position data (using well-known, conventional geometric coordinate conversion techniques), as indicated in block 1602. The data thus obtained is then analyzed in accordance with conventional medical testing procedures (block 1603).

More specifically, it is well known that various medical testing procedures are appropriate for diagnosis of various patient conditions, and these tests or procedures can be easily programmed by a skilled programmer, with appropriate medical guidance.

In general terms, the analysis function of block 1603 and determination function of block 1604 can be expressed mathematically as follows. Consider a one-dimensional experiment wherein only horizontal eye position (for example) is measured, and wherein one horizontal movement of the target is effected. Let:

$E(t_i)$ = eye position at time $t_i$ ($i=0,1,2,\ldots$)
$T(t_i)$ = target position at time $t_i$ ($i=0,1,2,\ldots$)
$t_i = i\cdot(\Delta t)$ where $\Delta t$ = sampling internal (say 5 msecs).

Then, in general, we want the following to occur or to be realized:

$T(t_{i+1})$ = position to which target is to be moved at time $t_{i+1}$ =

$$\sum_{j=0}^{i} f(j)\cdot e(t_j)$$

where
  f(j) = a weighting function
  $e(t_j)$ = eye position at earlier time $t_j$ before $t_{i+1}$; i.e., j less than i+1 and the summation is some function of eye position at earlier time(s).

Of course, as mentioned above, this is merely a theoretical expression of a medical decision-making process. Any skilled programmer, provided with appropriate technical guidance, would be able to implement the functions of block 1603, so as to arrive at the determinations made in block 1604, such determinations relating to the question of whether or not adjustment of the test stimuli is needed.

The program 1517 then makes a decision as to what test stimuli adjustment, if any, is desired or needed (block 1605), and appropriate action is then taken by the processor 34.

For example, if the rotatable chair is being utilized as a test stimuli, the processor 34 can be programmed to adjust the chair speed (block 1606), the direction of rotation of the chair (block 1607), or the number of turns in a particular direction (block 1608), any of which adjustments will be in accordance with the processed electrode data previously analyzed (block 1603).

Figure 14A:
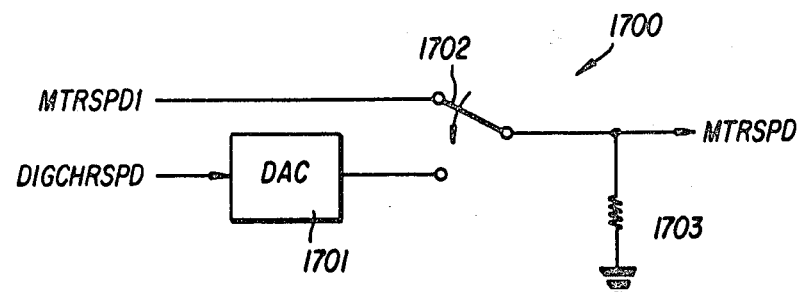
FIGS. 14A and 14B are diagrams of portions of the control panel 54 of the CEOG system of FIG. 2, modified for feedback control of test stimuli.
Figure 14B:
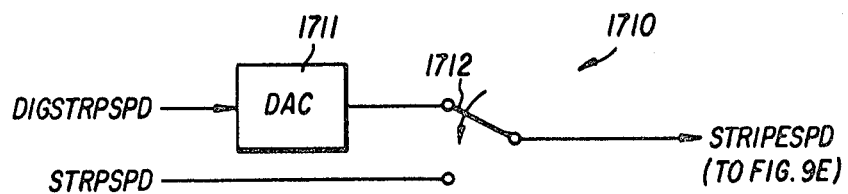

Referring to FIG. 14A, chair speed can be adjusted by loading a register (not shown) in the processor 34 with a speed-indicating digital word DIGCHRSPD. Then, the latter word is converted to analog form by DAC 1701, and provided to switch 1702, which, in this particular mode of operation, would be in its downward position so that the analog output of DAC 1701 would be provided via resistor 1703 as analog output MTRSPD from the control panel 54 (FIG. 2) to the motor controller 52. That is to say, the circuit 456 of FIG. 9C would be replaced by the circuit 1700 of FIG. 14A in order that analog output MTRSPD be derived selectively from analog input MTRSPD1 (set on the control panel 54 of FIG. 2 by the operator for automatic test administration), or from processor-generated digital word DIGCHRSPD.

In order to change direction of rotation of the rotatable chair (block 1607 of FIG. 13A), it is only necessary that the processor 34 generate the previously discussed commands RUNBKD, RUNFWD, provided as inputs to the portion L3' of the logic 62 (FIG. 10G). Finally, in order to set or adjust the number of turns of the rotatable chair (block 1608 of FIG. 13A), it is only necessary for the processor 34 to set the input B1-B4 to the multiplexer 650 (FIG. 10B), as previously discussed above.

With respect to adjustment of the flasher light stimuli, as mentioned above, flasher pulses are normally generated at a pulse separation of 5 milliseconds, as designated by the digital output DOUT13 from the computer 34. If it is decided that the flashing frequency is to be doubled, the computer can generate output DOUT11, which calls for the pulse separation to be cut to 2.5 milliseconds, thus doubling the frequency of flashing. It will be obvious to one of skill in the art that any number of digital bit outputs DOUTx could be provided in order to adjust the frequency of flashing either upward or downward to certain predetermined frequencies, as indicated by the particular bit DOUTx which is activated.

It is also within the capability of the present system to reposition the flashing light (block 1610) if such is determined to be necessary as a result of analysis of the data (block 1603). Accordingly, the processor 34 generates HORPOS and VERTPOS, digital data indicating horizontal and vertical positioning of the flashing light. This digital data is utilized, in the manner already covered above, to adjust or reposition the flashing light. Of course, various other techniques could be employed. For example, several alternative flashing lights could be located within the view of the patient, and, when it is desired to "reposition" the currently flashing light, the currently flashing light could be deactivated by computer command, and the "repositioned" flashing light could then be activated, also by computer command.

When the test stimuli comprises a moving or scanning light, such test stimuli can be varied in several ways: (1) adjustment of the opening of the shutter 66 (FIG. 2); (2) adjustment of the X and/or Y movement of the light via adjustment of the mirrors at drivers 14 (FIG. 2); and (3) generation of a predetermined pattern of movement (sine, triangle, etc.), as indicated and discussed above.

With respect to the adjustment of the opening of the shutter (block 1611 of FIG. 13A), such is achieved by computer-generation of −SHUT and +SHUT which control the opening and shutting, respectively, of the shutter 66, thus controlling the observance of the scanning light generated by the laser 12. When adjustment of the X and/or Y movement of the light is indicated (block 1612), the processor 34 generates commands XDRIVE and YDRIVE (discussed above), calling for the X-driving and Y-driving, respectively, of the mirrors 14. More specifically, it will be recalled from the above discussion (relative to FIGS. 10M and 10N) that the portion L10 of the logic 62 responds to data inputs MOVX and MOVY from the lowermost ten bits of the "Move X" and "Move Y" registers in the processor 34 to generate XDRIVE and YDRIVE for controlling X-direction and Y-direction scanning of the combination of laser 12 and mirrors/drivers 14 (FIG. 2).

If, as a result of the analysis of data (block 1603), it is determined (block 1604) that the needed adjustment of test stimuli amounts to generation of a predetermined pattern of movement of the moving light (block 1613), the processor 34 accomplishes this by generating digital words corresponding to the inputs SQUAR, TRINGL, and SINE to signal generator 1200 of FIG. 10O. In this manner, processor 34 causes the generation, by portion L11 of logic circuit 62, of signal SIGOUT corresponding to the desired pattern of light scanning selected by processor 34. As previously discussed, this signal SIGOUT is provided to portion L10 (FIG. 10M), and results in generation of appropriate mirror driving signals XDRIVE and YDRIVE so as to cause scanning in accordance with the pattern selected by the processor 34.

Finally, where the test stimuli is generated by an optokinetic device, it may be determined by the processor 34 that adjustment of the rotational speed of the device (block 1614) or change in the direction of rotation of the device (block 1615) is needed. If adjustment in the rotational speed is needed, a new speed may be designated by generation, by processor 34, of a digital word DIGSTRPSPD, the latter being provided to circuit 1710 of FIG. 14B (which replaces circuit 472 of FIG. 9C). The digital word DIGSTRPSPD is converted to analog form by DAC 1711, and is then provided via switch 1712 (which, in this mode of operation, is in its uppermost position) as signal STRIPESPD to the circuitry of FIG. 9E. With the switch 1712 in its lower position, the input STRPSPD (an analog input from the control panel 54 of FIG. 2) is provided to the circuitry of FIG. 9E. Thus, with switch 1712 in its uppermost position, the system is provided with the capability of processor-adjustment of the speed of rotation of the optokinetic device in response to analysis of data (block 1603 of FIG. 13A).

If it is determined that a change in the direction of rotation of the optokinetic device is needed (block 1615), this can be accomplished by processor-actuation of the switch 506 (FIG. 9D), so as to set or change the polarity of the voltage applied to the −CGMTR, +CGMTR terminals (connected to the relay panel 20 of FIG. 2). For example, the processor 34 can generate a digital command which, upon conversion to analog form, actuates a relay (not shown) for controlling the switch 506 of FIG. 9D, thus setting or reversing the polarity of the voltage applied, via switch 506, to the −CGMTR, +CGMTR terminals, thus controlling the direction of rotation of the stripe cage 76 of FIG. 2.

To summarize, the following registers and bits, contained in the processor 34, are important elements in connection with the adjustment of the test stimuli in reponse to analysis of the data by processor 34:

Control Word Register:

Bit 13 (DOUT 13), the "Go bit", generating output 5MSSAMP (FIG. 10J);

Bit 12 (DOUT 12-CMPSHTR), by means of which output SHUT (FIG. 10L) is generated to pulse the flasher; and Bit 11 (DOUT 11), by means of which the circuitry of FIG. 10J is actuated to adjust the flashing frequency in an upward direction to a value corresponding to 2.5 milliseconds between pulses.

The Move X Register:

Bit 10 (DOUT 10, the "Go X bit"), which causes scanning in the X direction in accordance with a sine wave pattern generated by the processor 34;

Bit 11 (CMPSINE), by means of which X-deflection of the mirrors is controlled in accordance with the ten least significant bits (bits 0-9) of the Move X Register;

Bit 12 (CMPSHTR), the same as bit 12 in the Control Word Register (above);

Bit 13 (YSCAN, "the Go Y Bit"), by means of which scanning in the Y direction is achieved; and Bits 0–9, by means of which X-deflection of the mirror is controlled.

Move Y Register:

Bits 0–9, by means of which Y-deflection of the mirrors is controlled.

Numerous modifications and adaptations of the system of the invention will be apparent to those skilled in the art and thus it is intended by the appended claims to cover all such modifications and adaptations which fall within the true spirit and scope of the invention.

What is claimed is:

1. An integrated medical testing system for automatically administering test stimuli to a patient, and for automatically varying said test stimuli in accordance with processed test results, comprising:
    stimulation control means for automatically administering said test stimuli to said patient;
    deriving means for connection to said patient for deriving test data from the patient as a result of the reaction of the patient to said test stimuli; and
    processor means connected to said deriving means for processing said derived test data to develop processed test results, and for generating stimulation control signals in accordance therewith wherein said processor means includes a analyzing means which is input with said derived test data and which analyzes said derived test data in accordance with a medical diagnostic testing procedure in order to provide said processed test results;
    said stimulation control means being connected to said processor means for receiving said stimulation control signals, and being responsive thereto for varying said test stimuli administered to said patient in accordance therewith.

2. The system of claim 1 further comprising a patient support means, said stimulation control means comprising a motor and a motor controller means responsive to said stimulation control signals from said processor means for varying the rotation of said patient support means.

3. The system of claim 2, wherein said motor controller means provides for rotation of said patient support means for a given number of turns and then stopping said rotation of said support means in response to said stimulation control signals.

4. The system of claim 2, wherein said motor controller means provides for stopping of said rotation of said support means in response to said stimulation control signals.

5. The system of claim 2, wherein said motor controller rotates said support means in a first direction and wherein said motor controller provides for automatic reversal of the direction of rotation of said support means after a given number of turns by stopping said rotation of said patient support means after said given number of turns, and by rotating said support means in a second direction, opposite to said first direction, for said given number of turns.

6. The system of claim 2, wherein said motor controller means provides for desired variation of a speed of rotation of said support means by varying the rotation of said support means in accordance with said desired variation of said speed of rotation in response to said stimulation control signals.

7. The system of claim 1, further comprising scanning light source means for generating a scanning light, said stimulation control means being responsive to said stimulation control signals from said processor means for controlling said scanning light source means to generate said scanning light.

8. The system of claim 7, wherein said scanning light source means controls movement of said scanning light in at least one direction in response to said stimulation control signals.

9. The system of claim 1, further comprising flasher light means for generating a flashing light, said stimulation control means being responsive to said stimulation control signals from said processor means for controlling said flasher light means to generate said flashing light.

10. The system of claim 9, wherein said flasher light means controls a frequency of flashing of said flashing light in response to said stimulation control signals.

11. The system of claim 1, further comprising optokinetic device means for generating optokinetic test stimuli, said stimulation control means being responsive to said stimulation control signals from said processor means for controlling said optokinetic device means to generate said optokinetic test stimuli.

12. The system of claim 11, wherein said optokinetic test stimuli comprises a rotating pattern of stripes in response to said stimulation control signals for controlling a direction of rotation of said rotating pattern of stripes.

13. The system of claim 11, wherein said optokinetic test stimuli comprises a rotating pattern of stripes in response to said stimulation control signals for controlling a speed of rotation of said rotating pattern of stripes.

* * * * *